US006538177B1

(12) United States Patent
Duvick et al.

(10) Patent No.: US 6,538,177 B1
(45) Date of Patent: Mar. 25, 2003

(54) COMPOSITIONS AND METHODS FOR FUMONISIN DETOXIFICATION

(75) Inventors: Jon Duvick, Des Moines, IA (US); Joyce Maddox, Des Moines, IA (US); Jacob Gilliam, Norwalk, IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/351,150

(22) Filed: Jul. 12, 1999

Related U.S. Application Data

(60) Provisional application No. 60/092,953, filed on Jul. 15, 1998.

(51) Int. Cl.$^7$ .......................... C12N 5/00; C12N 5/02; C12N 5/04; C12N 15/82; C07H 21/04

(52) U.S. Cl. .................... 800/279; 536/23.1; 536/23.6; 435/410; 435/419; 800/295

(58) Field of Search .............................. 536/23.6, 23.1; 800/279, 295; 435/6, 410, 320.1, 183, 419, 71.1

(56) References Cited

U.S. PATENT DOCUMENTS

| | | | |
|---|---|---|---|
| 5,178,863 | A | 1/1993 | Toyoda et al. |
| 5,639,949 | A | 6/1997 | Ligon et al. |
| 5,716,820 | A | 2/1998 | Duvick et al. |
| 5,792,931 | A | 8/1998 | Duvick et al. |
| 5,877,273 | A | 3/1999 | Hance et al. |

FOREIGN PATENT DOCUMENTS

| | | |
|---|---|---|
| EP | 0712932 A2 | 5/1996 |
| WO | 95/06121 | 3/1995 |
| WO | 95/06128 | 3/1995 |
| WO | 96/06175 | 2/1996 |
| WO | 96/12414 | 5/1996 |
| WO | 96/20595 | 7/1996 |
| WO | 99/02703 | 1/1999 |
| WO | 99/10514 | 3/1999 |
| WO | 99/32505 | 7/1999 |

OTHER PUBLICATIONS

James A. Wells, Additivity of Mutational Effects in Proteins, BIOCHEMISTRY, vol. 29, No. 37, Sep. 18, 1990.*

Rakin et al. (1994) "The Pesticin Receptor of *Yersinia enterocolitica*: A Novel Virulence Factor With Dual Function", *Molecular Microbiology 132*):253–263.

Schmidt et al. (1990) "Cloning and Nucleotide Sequence Of The *crtI* Gene Encoding Phytoene Dehydrogenase From The Cyanobacterium *Aphanocapsa* PCC6714", *Gene 91*(*9*):113–117.

Murakami et al. (Jan. 21, 1999) "Cloning And Sequence Analysis Of Two Catechol–Degrading Gene Clusters From The Aniline–Assimilating Bacterium *Frateuria* Species ANA–18", *Gene 226*(*2*):189–198.

Chattopadhyay et al. (1994) "Molecular Cloning And Sequencing Of An Operon, carRS Of *Azospirillum brasilense*, That Codes For A Novel Two–Component Regulatory System: Demonstration Of A Positive Regulatory Role Of carR For Global Control Of Carbohydrate Catabolism", *Journal of Bacteriology 176*(*24*):7484–7490.

Willins et al. (1991) "Characterization Of Lrp, an *Escherichia coli* Regulatory Protein That Mediates A Global Response To Leucine", *The Journal of Biological Chemistry 266*(*17*):10768–10774.

BLAST Searches in SwissProt, GenBank, DBest and Patents Databases.

Chen et al. (Jul. 16, 1988) "Acinetobacter sp. Cyclohexanone monooxygenase gene, completecds", EMBL Accession No.:M19029, XP002133308.

Chen et al. (Oct. 1, 1989) "Cyclohexanone Monooxygenase (EC 1.14.13.22)", SWISSPROT Accession No.:P12015, XP002133309.

Chen et al. (Oct. 1, 1989) "Flavin–binding monooxygenase–like", PFAM Accession No.:PF00743, XP002133310.

Itagaki et al. (Jan. 22, 1998) "Rhodococcus rhodochrous gene for steroidmonooxygenase, complete cds", EMBL Accession No.:AB010439, XP002133311.

Morii et al. (Jun. 1, 1998) "SteroidMonooxygenase", SWISSPROT Accession No.:050641, XP002133312.

Morii et al. Jun. 1, 1998) "Flavin–binding monooxygenase–like" PFAM Accession No.:PF00743, XP002133310.

Armengaud (Sep. 17, 1998) "Sphingomonas sp. ORFs G1, G3 to G8 and EDO2 gene", EMBL Accession No.:AJ223219, XP002133317, seents 3310–4600.

Armengaud (Nov. 1, 1998) "PutativeMonooxygenase", SWISSPROT Accession No.:086908, XP002133318.

Armengaud (Nov. 1, 1998) "Flavin–binding monooxygenase–like", PFRAM Accession No.:PF00743, XP002133310.

Duvick et al. (1998) "Detoxification OfMycotoxins In Planta As A Strategy For Improving Grain Quality And Disease Resistance: Identification Of Fumonisin–Degrading Microbes From Maize",*Molecular Genetics of Host–Specific Toxins In Plant Disease*, Proceedings of the 3$^{rd}$ Tottori International SymposiumDaisen, Tottori, Japan Aug. 24–29, 1997, pp. 369–381, ISBN: 0–7923–4981–4, 1998, XP002121275.

(List continued on next page.)

*Primary Examiner*—Sean McGarry
*Assistant Examiner*—Janet Epps
(74) *Attorney, Agent, or Firm*—Alston & Bird LLP

(57) ABSTRACT

Compositions and methods for the complete detoxification of fumonisin and fumonisin degradation products are provided. Particularly, nucleotide sequences corresponding to the detoxification enzymes are provided. The sequences find use in preparing expression cassettes for the transformation of a broad variety of host cells and organisms.

20 Claims, 4 Drawing Sheets

OTHER PUBLICATIONS

Blackwell et al. (1999) "Oxidative Deamination of Hydrolyzed Fumonisin $B_1$ ($AP_1$) by Cultures of *Exophiala spinifera", Natural Toxins 7*(*1*):31–38, ISSN: 1056–9014, XP002121276.

Anzai et al. (1989) "Transgenic Tobacco Resistant To A Bacterial Disease By The Detoxification Of A Pathogenic Toxin",*Mol Gen Genet 219*:492–494, ISSN: 0026–3924, XP002083624.

Linthorst et al. (1989) "Constitutive Expression of Pathogenesis–Related Proteins PR–1, GRP, and PR–S in Tobacco Has No Effect on Virus Infection", *The Plant Cell 1*:285–291.

Bennetzen et al. (1992) "Approaches and Progress in the Molecular Cloning of Plant Disease Resistance Genes", *Genetic Engineering 14*:99–124.

Ishihara et al. , AB#006450.

Chen et al. (Apr. 2, 1988), "Homo Sapiens P–Glycoprotein (PGY1) mRNA, Complete cds.," EMBL Accession No. M14758, XP002138295 and SWISSPROT Accession No. P08183 (Aug. 1, 1988).

Cox et al. (1996), "Styrene Metabolism in Exophiala Jeanselmei and Involvement of a Cytochrome P–450–Dependent Styrene Monooxygenase," Database Accession No. PREV199698822892, XP002138296, *Applied and Environmental Microbiology 62*(*4*):1471–1474.

Nikawa et al. (Nov. 21, 1990), "Saccharocyces Cerevisiae Choline Transport Protein Gene, Complete cds.,"EMBL Accession No. J05603, XP002138294 and SWISSPROT Accession No. P19807 (Jul. 15, 1998).

Schaap et al. (Jul. 24, 1998), "Agaricus Bisporus aldA and echA Genes," EMBL Accession No. Y17825, XP002138292.

Wang et al. May 15, 1996), "Pseudomonas Putida P–Cymene Catabolism (CYM) and P–Cumate Catabolism (CMT) Operons and ENOL–Coenzyme, A Hydratase Gene, Complete eds.," EMBL Accession No. U24215, XP002138293 and SPTREMBL Accession No. 033455 (Jan. 1, 1995).

Bergeron et al. (Jan. 19, 1998) "Cloning, sequence and expression of a linearplasmid–based and a chromosomal homolog of chloroacetaldehyde dehydrogenase–encoding genes in*Xanthobacter autorophicus* GJ10" *Gene 207*:9–18, XP002121100.

Perret et al. (Aug. 4, 1993) "Rhizobium sp. ORF–1 and ORF–2", EMBL Accession NoX74314, XP002121101, sequence 463–852.

Freiberg et al. (Oct. 1, 1996) "Putative transcriptional regulator Y4SM (ORF–1)", Swissprot Accession No:P50337, XP002121106, the whole document.

Madhusudhan et al. (Jul. 24, 1991) Pseudomonas putida branched–chain keto acid dehydrogenase operon (bkdA1, bkdA1 and bkdA2),transacylase E2 (bkdB), bkdR and lipoamide dehydrogenase (lpdV) genes, complete cds, EMBL Accession No:M57613, XP002121102, see reverse complement of sequence 1405–1010.

Madhusudhan et al. (Nov. 1, 1995) Bkd operon transcriptional regulator, SWISSPROT Accession No:P42179, XP002121107, the whole document.

Van Der Rest (Apr. 4, 1990) "Klebsiella pneumoniae cit(+) gene for citrate carrier protein", EMBL Accession No:X51479, XP002130931, the whole document.

Iimura(May 31, 1995) "Msx–2 homolog [human, dental pulp–derived cells,mRNA, 2065 nt]", EMBL Accession No:S75361, XP002130932, the whole document.

Seeger (Jul. 2, 1998) "Streptomyces coelicolor cosmid 8A6", EMBL Accession NαAL031013, XP002130933, the whole document.

Heller et al. (Nov. 18, 1996) "*E. coli* btuB gene for the vitamin B12 receptor protein BtuB", EMBL Accession No:M10112, XP002130934, the whole document and SWISSPROT Accession No:P06129, (Jan. 1, 1998).

Peng et al. (Jul. 1998) "Cloning of a*Sphingomonas paucimobilis* SYK–6 Gene Encoding a Novel Oxygenase That Cleaves Lignin–Related Biphenyl and Characterization of the Enzyme"*Applied and Environmental Microbiology 64*(*7*):2520–2527, XP002130935.

Cole et al. (Feb. 22, 1998) "Mycobacterium tuberculosis H37Rv complete genome; segment 33/162", EMBL Accession No:AL021943, XP002130936, the whole document.

Plunkett et al. (Dec. 30, 1994) "*Escherichia coli* K–12 chromosomal region from 67.4 to 76.0 minutes", EMBL Accession No:U18997, XP002130937, the whole document.

Murphy et al. (Jan. 26, 1998) "Streptomyces coelicolor cosmid 10A5", EMBL Accession NαAL021529, XP002121096, see reverse complement of 20673–20430.

Du (Dec. 15, 1996) "Mycobacterium tuberculosis sequence from clone Y175", EMBL Accession No:AD000015, XP002121097, see sequence 6027–6064.

Cole et al. (Nov. 9, 1997) "Mycobacterium tuberculosis H37Rv compelete genome; segment 125–162", EMBL Accession No:AL008883, XP002121098, see sequence 1434–1843.

Bergeron et al. (Dec. 4, 1997) "Xanthobacter autotrophicus transcriptional activator AldR (aldR) gene, partial cds; and NAD–dependent chloroacetaldehyde dehydrogenase (aldB) gene, complete cds", EMBL Accession No:AF029734, XP002121099, see reverse complement of sequence 2447–2066.

Oliver et al. (May 27, 1998) "Streptomyces cosmid IC3", EMBL Accession NαAL023702, XP002130938, the whole document.

Martinez–Salazar et al. (Apr. 1996) "Characterization of the Genes Coding for the Putative Sigma FactorAlgU and Its Regulators MucA, MucB, MucC, and MucD in *Azotobacter vinelandii* and Evaluation of Their Roles in Alginate Biosynthesis",*Journal of Bacteriology 178*(*7*):1800–1808, XP002130939.

Cole et al. (Feb 22, 1998) "Mycobacterium tuberculosis H37Rv complete genome; segment 29/162", EMBL Accession No:AL021942, XP002130940, the whole document.

Coulton et al. (Nov. 18, 1996) "*E. coli* fhuA, fhuC and fhuD genes encoding the ferrichrome–iron receptor and two ferric aerobactin and ferric coprogen transport proteins, completecds.", EMBL Accession No:M12486, XP002130941, the whole document.

Coulton et al. (Apr. 1, 1988) "Ferrichrome–Iron Receptor Precursor (Ferric Hydroxamate Uptake)", SWISSPORT Accession No:P06971, XP002130942.

Seebacher et al. (Oct. 17, 1996) "R. norvegicus mRNA for laminin chain, 765bp", EMBL Accession No:Y08882, XP002130943, the whole document.

Cole et al. (Jan. 15, 1998) "Mycobacterium tuberculosis H37Rv complete genome; segment 132/162", EMBL Accession No:AL021287, XP002130944, the whole document and TREMBL Accession No:053294, (Jun. 1, 1998).

Cole et al. (May 10, 1996) "Mycobacterium tuberculosis H37Rv complete genome; segment 41/162", EMBL Accession No:Z73101, XP002130945, the whole document and "ProbableMonooxygenase RV0892 (EC 1.14.13.*)," SWISSPROT Accession No:Q10532 (Oct. 1, 1996).

Peterson et al. (1992) "Cytochrome P–450terp. Isolation and Purification of the Protein and Cloning and Sequencing of Its Operon", *Journal of Biological Chemistry 267* (*20*):14193–14203, XP002130946 figures 4, 8 and EMBL Accession No:M91440 (Apr. 17, 1992), and "Probablealdehyde dehydrogenase (EC 1.2.1.3)" SWISSPROT Accession No:P33008 (Oct. 1, 1993).

Cole et al. (Mar. 12, 1998) "Mycobacterium tuberculosis H37Rv complete genome; segment 155/162", EMBL Accession No:AL022121, XP002130947, the whole document.

Klenk et al. ( Dec. 1, 1997) "Archaeoglobus fulgidus section 144 of 172 of the complete genome", EMBL Accession No:AE000963, XP002130948, the whole document.

Bowen et al. (May 5, 1997) "Cloning and Phylogenetic Analysis of the Genes EncodingAcetohydroxyacid Synthase from the Archaeon *methanococcus aeolicus", Gene 188*:77–84, XP002130949 figure 2 and EMBL Accession No:U35458 (May 5, 1997).

Vlcek et al. (May 13, 1998), "Rhodobacter capsulatus strain SB1003, partial genome", EMBL Accession No:AF010496, XP002130950, the whole document.

Pealing et al. (Nov. 3, 1992) "Shewanella putrefaciens flavocytochrome c gene, complete cds.", EMBL Accession No:L04283, XP002130951, the whole document.

Walczak et al. (Jul. 14, 1998) "Streptomyces griseus subsp. Griseus nonactin biosynthesis gene cluster, partial sequence", EBML Accession No:AF074603, XP002130952, the whole document.

Ishiguro et al. (Apr. 22, 1989) "Transposon Tn4311 (from *E. coli* K–12) citrate utilization protein citA and citB genes, complete cds.", EMBL Accession No:M22041, XP002130953, the whole document.

Chudhary et al. (Jun 6, 1998) "483PLA2Cosmid library of chromosome IIRhodobacter sphaeroides genomic clone 483PLA2, genomic survey sequence", EMBL Accession NoαAQ012082, XP002130954, the whole document.

Molnar et al. (Oct. 29, 1992) "Streptomyces sp. Genes for hypothetic proteins", EMBL Accession No:D13457, XP002130955 the whole document.

Bedzyk et al. (Jun. 15, 1993) "Paracoccus denitrificans electron transfer flavoprotein alpha and beta subunit genes, complete cds's.", EMBL Accession No:L14864, XP002130956 the whole document.

Duvick et al. (1988) "Detoxification ofmycotoxins in planta as a strategy for improving grain quality and disease resistance: identification of fumonisin–degrading enzymes from maize",*Molecular Genetics of Host–Specific Toxins In Plant Disease*, pp. 369–381, Proceedings of the 3[rd]Tottori International Symposium Daisen, Tottori, Japan, Aug. 24–29, 1997, Kluwer Academic Publishers, Dordrecht, ISBN: 0–7923–4981–4, XP002121275.

Anzai et al. (Jan. 1, 1989) "Transgenic tobacco resistant to a bacterial disease by the detoxification of a pathogenic toxin", *Molecular and General Genetics 219*:492–494, XP002083624, ISSN: 0026–3925 the whole document.

Blattner et al. (Jan. 29, 1997) *"Escherichia coli* K–12 MG1655 section 69 of 400 of the complete genome", EMBL Accesion No:AE000179, XP002122134 see complement (4647..5663).

Blattner et al. (Oct. 1, 1996) "Hypotheticaltranscriptional regulator in MODC–BIOA intergenic region", SWISSPROT Accession No:p52696, xp002121103 the whole document.

Kim et al. (Feb. 4, 1998) "Organization and transcriptional characterization of the $cat_1$ gene cluster in Acinetobacter iwoffii K24", *Biochemical and Biophysical Research Communications 243*:289–294, XP002121104 see fig. 2 and fig. 3 ORFR1.

Ghosh et al. (Jan. 30, 1995) "A.brasilense carR gene", EMBL Accession No:X70360, XP002122135 the whole document and Chattophadhyay et al. (Nov. 1, 1996) "CarR Gene", TREMBL Accession NO:Q43901, XP002121105 the whole document.

Willins et al. (Aug. 4, 1990) "*E. coli* leucine–responsive–regulatory protein (Lrp) gene, complete cds.", EMBL Accession No:M35869, XP002122136 see sequence 1..495 and Willins et al. (Feb. 1, 1991) "Leucine–responsive regulatory protein", SWISSPROT Accession No:P19494, XP002121108 the whole document.

PCT Notification of Transmittal of the International Search Report of the Declaration mailed Mar. 20, 2000, International Application No. PCT/US99/15837, International Filing Date Jul. 14, 1999.

Murphy et al. (Jan. 26, 1998) "Streptomyces Coelicolor Cosmid 10A5", EMBL Accession No. AL021529, XP002121096, see reverse complement of 20673–20430.

Du (1996) "Mycobacterium Tuberculosis Sequence From Clone y175", EMBL Accession No. AD000015, XP002121097, see sequence 6027–6064.

Cole et al. (1997) "Mycobacterium Tuberculosis H37Rv Complete Genome; segment 125–162", EMBL Accession No. AL008883, XP002121098, see sequence 1434–1843.

Bergeron et al. (1997) "Xanthobacter Autotrophicus Trnascriptional Activator AldR (aldR) Gene, Partial cds.; and NAD–dependent Chloroacetaldehyde Dehydrogenase (aldB) Gene, Complete cds", EMBL Accession No. AF029734, XP002121099, see reverse complement of sequence 2447–2066.

Bergeron et al. (Jan. 19, 1998) "Cloning, Sequence and Expression of a Linear Plasmid–Based and Chromosomal Homolog of Chloracetaldehyde Dehydrogenase–Encoding Genes in *Xanthobacter autotrophicus* GJ10", *Gene 207*:9–18, XP002121100.

Perret et al. (1993) "Rhizobium sp. ORF–1 and ORF–2", EMBL Accession No. X74314, XP002121101,sequence 463–852.

Freiberg et al. (1996) "Putative Transcriptional Regulator Y4SM (ORF–1)", SWISSPROT Accession No. P50337, XP002121106, the whole document.

Madhusudhan et al. (1991) "Pseudomonas Putida Branched– Chain Keto Acid Dehydrogenase Operon (bkdA1, bkdA1 and bkdA2), Transacylase E2 (bkdB), bkdR and Lipoamide Dehydrogenase (1pdV) Genes, Complete cds", EMBL Accession No. M57613, XP002121102, see reverse complement of sequence 1405–1010.

Madhusudhan et al. (1995) "Bkd Operon Transcriptional Regulator", SWISSPROT Accession No. P42179, XP002121107 the whole document.

Duvick et al. (Aug. 1997) "Detoxification of Mycotoxins In Planta As A Strategy For Improving Grain Quality and Disease Resistance: Identification of Fumonisin–Degrading Microbes From Maize", *Molecular Genetics of Host–Specific Toxins In Plant Disease*, Proceedings of the 3rd Tottori International Symposium Daisen, Tottori, Japan, Kluwer Academic Publishers, Dordrecht, ISBN: 0–7923–4981–4, XP002121275, pp. 369–381.

Anzai et al. (1989) "Transgenic Tobacco Resistant To A Bacterial Disease By The Detoxification Of A Pathogenic Toxin", *Mol. Gen. Genet 219*:492–494, XP–002083624.

Blattner et al. (1997) "*Escherichia coli* K–12, MG1655 Section 69 of 400 of the Complete Genome", EMBL Accession No. AE000179, XP002122134, see complement (4647–5663).

Blattner et al. (1996) "Hypothetical Transcriptional Regulator in MODC–BIOA Intergenic Region", SWISSPROT Accession No. P52696, XP002121103.

Kim et al. (Feb. 4, 1998) "Organization and Transcriptional Characterization of the $cat_1$ Gene Cluster in *Acinetobacter Iwoffii* K24", *Biochemical and Biophysical Research Communications 243*:289–294, XP002121104.

Ghosh et al. (1995) "A. Brasilense carR Gene", EMBL Accession No. X70360, XP002122135.

Chattopadhyay et al. (1996) "CarR Gene", TREMBL Accession No. Q43901, XP002121105.

Willins et al. (1990) "*E. coli* Leucine–Responsive–Regulatory Protein (Lrp) Gene, Complete cds.", EMBL Accession No. M35869, XP002122136, see sequence 1–495.

Willins et al. (1991) "Leucine–Responsive Regulatory Protein", SWISSPROT Accession No P19494, XP002121108.

* cited by examiner

Proposed pathway for fumonisin catabolism by bacterium 2412.1

Map of overlapping fragments used to reconstruct the gene cluster.

COMPOSITIONS AND METHODS FOR FUMONISIN DETOXIFICATION

CROSS-REFERENCE TO RELATED APPLICATIONS

This application claims the benefit of U.S. Provisional Application No. 60/092,953, filed Jul. 15, 1998.

FIELD OF THE INVENTION

The invention relates to compositions and methods for detoxification or degradation of fumonisins and related toxins. The method has broad application in agricultural biotechnology and crop agriculture and in the improvement of food grain quality.

BACKGROUND OF THE INVENTION

Fungal diseases are common problems in crop agriculture. Many strides have been made against plant diseases as exemplified by the use of hybrid plants, pesticides, and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop losses, is interference with the mechanism by which the pathogen causes injury to the host crop plant. In the case of pathogens that produce toxins that are undesirable to mammals or other animals that feed on the crop plants, interference with toxin production, storage, or activity can be beneficial.

Since their discovery and structural elucidation in 1988 (Bezuidenhout et al. (1988) *Journal Chem. Soc., Chem. Commun.* 1988:743–745), fumonisins have been recognized as a potentially serious problem in maize-fed livestock. They are linked to several animal toxicoses including leukoencephalomalacia (Marasas et al. (1988) *Onderstepoort J. Vet. Res.* 55:197–204; Wilson et al. (1990) *American Association of Veterinary Laboratory Diagnosticians: Abstracts 33rd Annual Meeting,* Denver, Colo., Madison, Wis., USA) and porcine pulmonary edema (Colvin et al. (1992) *Mycopathologia* 117:79–82). Fumonisins are also suspected carcinogens (Geary et al. (1971) *Coord. Chem. Rev.* 7:81; Gelderblom et al. (1991) *Carcinogenesis* 12:1247–1251; Gelderblom et al. (1992) *Carcinogenesis* 13:433–437). Fusarium isolates in section Liseola produce fumonisins in culture at levels from 2 to >4000 ppm (Leslie et al. (1992) *Phytopathology* 82:341–345). Isolates from maize (predominantly mating population A) are among the highest producers of fumonisin (Leslie et al., supra). Fumonisin levels detected in field-grown maize have fluctuated widely depending on location and growing season, but both preharvest and post-harvest surveys of field maize have indicated that the potential for high levels of fumonisins exists (Murphy et al. (1993) *J. Agr. Food Chem.* 41:263–266). Surveys of food and feed products have also detected fumonisin (Holcomb et al. (1993) *J. Agr. Food Chem.* 41:764–767; Hopmans et al. (1993) *J. Agr. Food Chem.* 41:1655–1658); Sydenham et al. (1991) *J. Agr. Food Chem.*

39:2014–2018). The etiology of Fusarium ear mold is poorly understood, although physical damage to the ear and certain environmental conditions can contribute to its occurrence (Nelson et al. (1992) *Mycopathologia* 117:29–36). Fusarium can be isolated from most field grown maize, even when no visible mold is present. The relationship between seedling infection and stalk and ear diseases caused by Fusarium is not clear. Genetic resistance to visible kernel mold has been identified (Gendloff et al. (1986) *Phytopathology* 76:684–688; Holley et al. (1989) *Plant Dis.* 73:578–580), but the relationship between visible mold and fumonisin production has yet to be elucidated.

Fumonisins have been shown in in vitro mammalian cell studies to inhibit sphingolipid biosynthesis through inhibition of the enzyme sphingosine N-acetyl transferase, resulting in the accumulation of the precursor sphinganine (Norred et al. (1992) *Mycopathologia* 117:73–78; Wang et al. (1991) *Biol. Chem.* 266:14486; Yoo et al. (1992) *Toxicol. Appl. Pharmacol.* 114:9–15; Nelson et al. (1993) *Annu. Rev. Phytpathol.* 31:233–252). It is likely that inhibition of this pathway accounts for at least some of fumonisin's toxicity, and support for this comes from measures of sphinganine:sphingosine ratios in animals fed purified fumonisin (Wang et al. (1992) *J. Nutr.* 122:1706–1716). Fumonisins also affect plant cell growth (Abbas et al. (1992) *Weed Technol.* 6:548–552; Van Asch et al. (1992) *Phytopathology* 82:1330–1332; Vesonder et al. (1992) *Arch. Environ. Contam. Toxicol.* 23:464–467). Kuti et al. (1993) (Abstract, Annual Meeting American Phytopathological Society, Memphis, Tenn.: APS Press) reported on the ability of exogenously added fumonisins to accelerate disease development and increase sporulation of *Fusarium moniliform* and *F. oxysporum* on tomato.

Enzymes that degrade the fungal toxin fumonisin to the compound AP1 have been identified in U.S. Pat. No. 5,716,820 and pending U.S. patent application Ser. Nos. 08/888,949 and 08/888,950, both filed Jul. 7, 1997, and hereby incorporated by reference. Plants expressing a fumonisin esterase enzyme, infected by fumonisin producing fungus, and tested for fumonisin and AP1 were found to have low levels of fumonisin but high levels of AP1. AP1 is less toxic than fumonisin to plants and probably also animals, but contamination with AP1 is still a concern. The best result would be complete detoxification of fumonisin to a non-toxic form. Therefore additional enzymes capable of degrading fumonisin and fumonisin catabolic products are necessary for the complete detoxification of fumonisin.

SUMMARY OF THE INVENTION

A fumonisin detoxification gene cluster is provided. Particularly, the nucleotide sequence for the cluster from Bacterium 2412.1 (American Type Culture Collection Deposit Number 55552) is provided. At least twelve structural genes and three regulatory gene are provided. The sequences represent a catabolic pathway for fumonisins and fumonisin-like compounds.

Compositions and methods for catabolism and detoxification of fumonisin, fumonisin-related toxins, and fumonisin-degradation products are provided. In particular, proteins involved in catabolism and transmembrane transport of fumonisin and fumonisin catabolic products are provided. Nucleotide sequences corresponding to the proteins are also included. The compositions are useful in the complete detoxification and degradation of fumonisin. The nucleotide sequences can be used in expression cassettes for transformation of host cells of interest. The compositions and methods of the invention provide a catabolic pathway for fumonisin. Thus, organisms can be genetically modified to provide for the complete catabolism and detoxification of fumonisin and fumonisin-related toxins.

In particular, expression cassettes for expression of the sequences in plants and other organisms are provided as well as transformed plants and other host cells.

DETAILED DESCRIPTION OF THE INVENTION

A catabolic pathway for detoxification and degradation of fumonisin is provided. Particularly, enzymes involved in the degradation of fumonisin from Bacterium 2412.1 and nucleotide sequences encoding such enzymes are disclosed. Such enzymes and nucleotide sequences find use in the breakdown of fumonisin as well as fumonisin-degradation products. In this regard, enzymes can be synthesized and utilized or, alternatively, organisms can be transformed with the DNA sequences of the invention and used to detoxify fumonisin.

Figure 1:
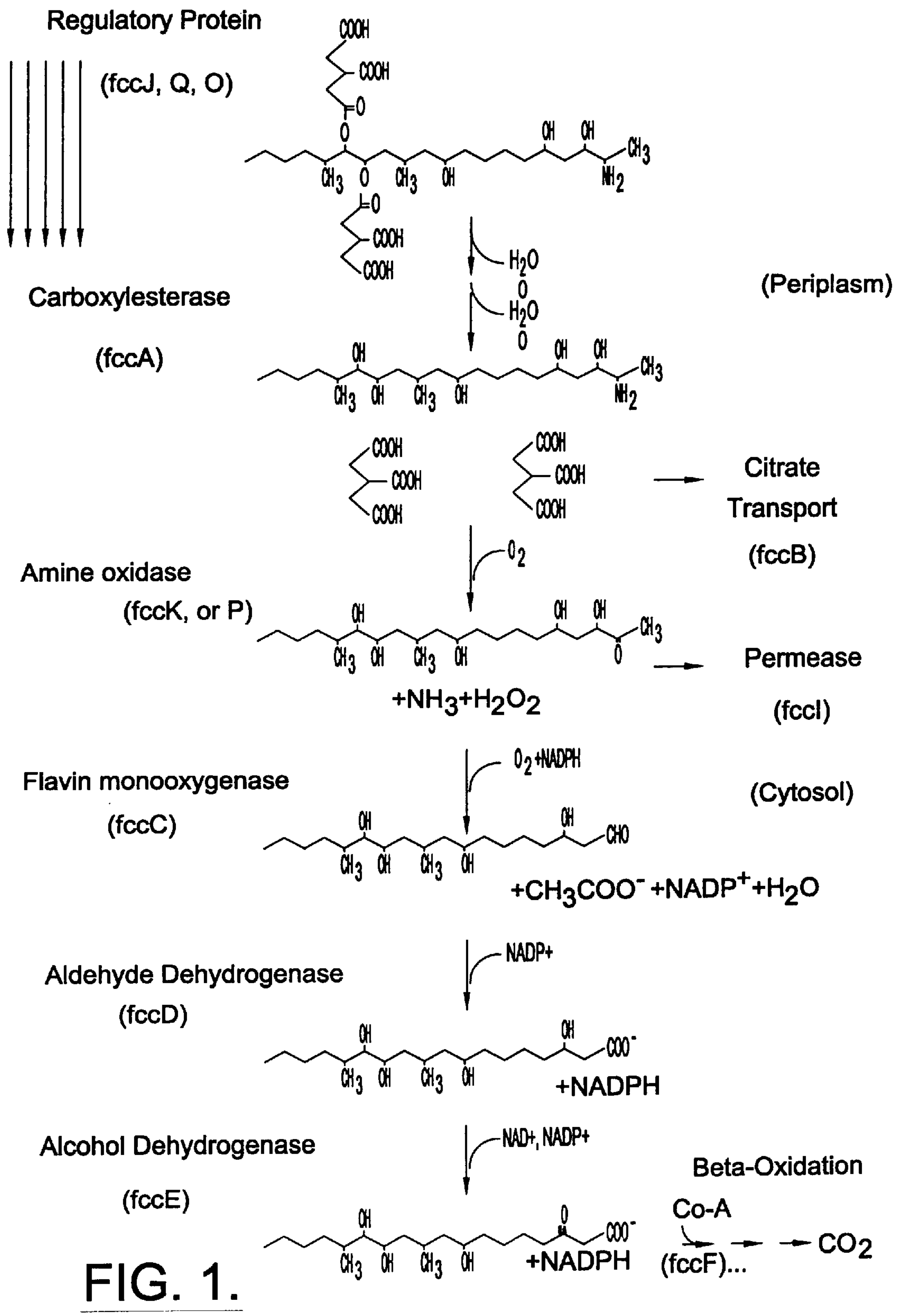
FIG. 1 sets forth the proposed pathway for fumonisin degradation by Bacterium 2412.1.

A proposed pathway for the degradation of fumonisin by Bacterium 2412.1 is provided in FIG. 1. The present invention provides enzymes and nucleotide sequences encoding the enzymes involved in this degradation pathway for fumonisin. In particular, the present invention provides for isolated nucleic acid molecules comprising the fumonisin catabolic gene cluster for Bacterium 2412.1 set forth in SEQ ID NO: 1, or the DNA sequences obtained from the overlapping clones deposited with the American Type Culture Collection and assigned Accession Numbers PTA-296, PTA-297, and PTA-298. By "DNA sequence obtained from the overlapping clones" is intended that the DNA sequence of the catabolic gene cluster can be obtained by sequencing 18 individual clones which together comprise the entire fumonisin catabolic cluster.

Further provided are polypeptides having an amino acid sequence encoded by a nucleic acid molecule set forth in SEQ ID NO:1, the nucleic acid molecule deposited as overlapping clones with the American Type Culture Collection and assigned Accession Numbers PTA-296, PTA-297, and PTA-298, and fragments and variants thereof.

Eighteen plasmids containing overlapping clones were deposited with the American Type Culture Collection, Manassas, Va., and assigned Accession Numbers PTA-298, PTA-296, and PTA-297 (strain designations SuperCos_8.5_1, BAM_PL1, and BAM_PL2, respectively). It is noted, however, that the 18 clones contain common sequences at the regions where they overlap. One of skill in the art by sequencing the clones and aligning the overlap may obtain the entire sequence of the fumonisin catabolic gene cluster. These deposits will be maintained under the terms of the Budapest Treaty on the International Recognition of the Deposit of Microorganisms for the Purposes of Patent Procedure. These deposits were made merely as a convenience for those of skill in the art and are not an admission that a deposit is required under 35 U.S.C. § 112.

In addition, the present invention provides for isolated nucleic acid molecules comprising nucleotide sequences encoding the amino acid sequences of a regulatory protein (fccJ) (SEQ ID NO: 21); a carboxylesterase (fccA) (SEQ ID NO: 3), a flavin monooxygenase (fccC) (SEQ ID NO: 7); an aldehyde dehydrogenase (fccD) (SEQ ID NO: 9); an alcohol dehydrogenase (fccE) (SEQ ID NO: 11); a permease (fccI) (SEQ ID NO: 19); a CoA Ligase (fccF) (SEQ ID NO: 13); an acetohydroxyacid synthase (fccG) (SEQ ID NO: 15); a vitamin B12 transporter (fccH) (SEQ ID NO: 17); a citrate transport homolog (fccB) (SEQ ID NO: 5); a fumarate reductase (fccK) (SEQ ID NO: 23), a TonB dependent receptor (fccL) (SEQ ID NO: 25); a carbohydrate regulatory gene (fccO) (SEQ ID NO: 31); a citrate utilization B protein (fccN) (SEQ ID NO: 29); a possible flavoenzyme (fccP) (SEQ ID NO: 33); a leucine responsive regulatory protein (fccQ) (SEQ ID NO: 35); a possible N-methyl transferase (fccM) (SEQ ID NO: 27); fccR (SEQ ID NO: 37); fccS (SEQ ID NO: 39); and fccT (SEQ ID NO: 41).

Further provided are polypeptides having an amino acid sequence encoded by a nucleic acid molecule described herein, for example those set forth in SEQ ID NOS: 2, 4, 6, 8, 10, 12, 14, 16, 18, 20, 22, 24, 26, 28, 30, 32, 34, 36, 38, and 40. The nucleotide sequences of the invention can be used to isolate related sequences that are also encompassed by the present invention.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, preferably culture medium represents less than about 30%, 20%, 10%, or 5% (by dry weight) of chemical precursors or non-protein-of-interest chemicals.

The isolated material optionally comprises material not found with the material in its natural environment or, if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA that has been altered, by non-natural, synthetic (i.e., "man-made") methods performed within the cell from which it originates.

See, e.g., Compounds and Methods for Site Directed Mutagenesis in Eukaryotic Cells, Kmiec, U.S. Pat. No. 5,565,350; In vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids that are "isolated" as defined herein are also referred to as "heterologous" nucleic acids.

A carboxylesterase and amine oxidase from *Exophiala spinifera* have been previously described in U.S. Pat. No. 5,716,820 and pending U.S. patent application Ser. Nos. 08/888,949 and 08/888,950. Such disclosures are herein incorporated by reference.

The sequences of the invention can be used in combination with those previously disclosed in U.S. provisional application numbers 60/092,936 and 60/135,391 herein incorporated by reference. The enzymes and nucleotide sequences of the present invention provide a means for catabolism of fumonisin and of the fumonisin-degradation products.

The practice of the present invention will employ, unless otherwise indicated, conventional techniques of botany, microbiology, tissue culture, molecular biology, chemistry, biochemistry, and recombinant DNA technology, which are within the skill of the art. Such techniques are explained fully in the literature. See, e.g., Langenheim and Thimann (1982) *Botany: Plant Biology and Its Relation to Human Affairs* (John Wiley); Vasil, ed. (1984) *Cell Culture and Somatic Cell Genetics of Plants,* Vol. 1; Stanier et al. (1986) *The Microbial World* (5th ed., Prentice-Hall); Dhringra and Sinclair (1985) *Basic Plant Pathology Methods* (CRC Press); Maniatis et al. (1982) *Molecular Cloning: A Laboratory Manual* (Cold Spring Harbor Laboratory Press, Cold Spring Harbor, New York); Glover, ed. (1985) *DNA Cloning, Vols. I and II;* Gait, ed. (1984) *Oligonucleotide Synthesis;* Hames and Higgins, eds. (1984) *Nucleic Acid Hybridization;* and the series *Methods in Enzymology* (Colowick and Kaplan, eds., Academic Press, Inc.).

In describing the present invention, the following terms will be employed, and are intended to be defined as indicated below.

By "microbe" is meant any microorganism (including both eukaryotic and prokaryotic microorganisms), such as fungi, yeast, bacteria, actinomycetes, algae, and protozoa, as well as other unicellular structures.

A "fumonisin-producing microbe" is any microbe capable of producing the mycotoxin fumonisin or analogues thereof. Such microbes are generally members of the fungal genus Fusarium, as well as recombinantly derived organisms that have been genetically altered to enable them to produce fumonisin or analogues thereof.

By "degrading or catabolizing fumonisin" is meant any modification to the fumonisin or AP1 molecule that causes a decrease or loss in its toxic activity. Such a change can comprise cleavage of any of the various bonds, oxidation, reduction, the addition or deletion of a chemical moiety, or any other change that affects the activity of the molecule. In a preferred embodiment, the modification includes hydrolysis of the two ester linkages in the molecule as a first step and then oxidative deamination. Furthermore, chemically altered fumonisin can be isolated from cultures of microbes that produce an enzyme of this invention, such as by growing the organisms in media containing radioactively-labeled fumonisin, tracing the label, and isolating the degraded toxin for further study. The degraded fumonisin can be compared to the active compound for its phytotoxicity or mammalian toxicity in known sensitive species, such as porcines and equines. Such toxicity assays are known in the art. For example, in plants a whole leaf bioassay can be used in which solutions of the active and inactive compound are applied to the leaves of sensitive plants. The leaves may be treated in situ or, alternatively, excised leaves may be used. The relative toxicity of the compounds can be estimated by grading the ensuing damage to the plant tissues and by measuring the size of lesions formed within a given time period. Other known assays can be performed at the cellular level, employing standard tissue culture methodologies e.g., using cell suspension cultures. For purposes of the invention, the fumonisin or fumonisin degradation products will be degraded to at least about 50% to about 10% or less of the original toxicity, preferably about 30% to about 5% or less, more preferably about 20% to about 1% or less.

By "fumonisin esterase" is meant any enzyme capable of hydrolysis of the ester linkages in fumonisin. Two examples of such enzymes are ESP1 and BEST1 found in U.S. Pat. No. 5,716,820 and pending U.S. application Ser. Nos. 08/888,949 and 08/888,950, both filed Jul. 7, 1997.

By "structurally related mycotoxin" is meant any mycotoxin having a chemical structure related to a fumonisin such as fumonisin B1, for example AAL toxin, fumonisin B2, fumonisin B3, fumonisin B4, fumonisin C1, fumonisin A1 and A2, and their analogues, as well as other mycotoxins having similar chemical structures that would be expected to be detoxified by activity of the fumonisin degradative enzymes elaborated by *Exophiala spinifera,* American Type Culture Collection Accession No. 74269, *Rhinocladiella atrovirens,* American Type Culture Collection Accession No. 74270, or the bacterium of American Type Culture Collection Accession No. 55552.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Persing et al., ed. (1993) *Diagnostic Molecular Microbiology: Principles and Applications,* (American Society for Microbiology, Washington, D.C.). The product of amplification is termed an amplicon.

Fragments and variants of the disclosed nucleotide sequences and proteins encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence degrade or catabolize fumonisin. Alternatively, fragments of a nucleotide sequence that are useful as hybridization probes generally do not encode protein fragments retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a fumonisin-degrading nucleotide sequence that encodes a biologically active portion of a fumonisin-degrading protein of the invention will encode at least 15, 20, 25, 30, 50, 100, 150, 200, 250, 300, 350, 400, 450, 500, 550, 600, 650, 700, 750, 800, 850, 900, or 950 contiguous amino acids, or up to the total number of amino acids present in a full-length fumonisin-degrading protein of the invention. By fragment it is also intended any nucleotide sequence of the fumonisin-catabolic gene cluster that encodes a biologically active portion of a fumonisin-degrading protein. Fragments of a fumonisin-degrading nucleotide sequence that are useful as hybridization probes for PCR primers generally need not encode a biologically active portion of a fumonisin-degrading protein.

Thus, a fragment of a fumonisin-degrading nucleotide sequence or a fragment of the fumonisin-catabolic gene cluster may encode a biologically active portion of a fumonisin-degrading protein or it may be a fragment that can be used as a hybridization probe or PCR primer using methods disclosed below. A biologically active portion of a fumonisin-degrading protein can be prepared by isolating a portion of one of the fumonisin-degrading nucleotide sequences or a portion of the fumonisin-catabolic gene cluster of the invention, expressing the encoded portion of the fumonisin-degrading protein (e.g., by recombinant expression in vitro), and assessing the activity of the encoded portion of the fumonisin-degrading protein. Nucleic acid molecules that are fragments of a fumonisin-degrading nucleotide sequence comprise at least 15, 20, 50, 75, 100, 150, 200, 250, 300, 350, 400, 450, 500, 550, 600, 650, 700, 750, 800, 850, 900, 950, 1,000, 1,100, 1,200, 1,300, 1,400, 1,500, 1,600, 1,700, 1,800, 1,900, 2,000, 2,100, 2,200, 2,300, 2,400, 2,500, 2,600, 2,700, 2,800 nucleotides, or up to the number of nucleotides present in a fumonisin-degrading nucleotide sequence or up to the number of nucleotides present in the full-length fumonisin catabolic gene cluster disclosed herein.

By "variants" is intended substantially similar sequences. For nucleotide sequences conservative variants include those sequences that, because of the degeneracy of the genetic code, encode the amino acid sequence of one of the fumonisin-degrading polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a fumonisin-degrading protein of the invention. Generally, nucleotide sequence variants of the invention will have at least 40%, 50%, 60%, 70%, generally, 80%, preferably 85%, 90%, up to 95%, 98% sequence identity to its respective native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation.

The proteins of the invention may be altered in various ways including amino acid substitutions, deletions, truncations, and insertions. Methods for such manipulations are generally known in the art. For example, amino acid sequence variants of the fumonisin-degrading proteins can be prepared by mutations in the DNA. Methods for mutagenesis and nucleotide sequence alterations are well known in the art. See, for example, Kunkel (1985) Proc. Natl. Acad. Sci. USA 82:488–492; Kunkel et al. (1987) Methods in Enzymol. 154:367–382; U.S. Pat. No. 4,873,192; Walker and Gaastra, eds. (1 983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferred.

Thus, the genes and nucleotide sequences of the invention include both the naturally occurring sequences as well as mutant forms. Likewise, the proteins of the invention encompass both naturally occurring proteins as well as variations and modified forms thereof. Such variants will continue to possess the desired ability to degrade fumonisin and fumonisin-like compounds. Obviously, the mutations that will be made in the DNA encoding the variant must not place the sequence out of the reading frame and preferably will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by a decrease or loss in the toxic activity of fumonisin or AP1.

Variant nucleotide sequences and proteins also encompass sequences and proteins derived from a mutagenic and recombinogenic procedure such as DNA shuffling. With such a procedure, one or more different fumonisin-degrading protein coding sequences can be manipulated to create a new fumonisin-degrading protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the fumonisin-degrading genes of the invention and other known fumonisin-degrading genes to obtain a new gene coding for a protein with an improved property of interest, such as an increased $K_m$ in the case of an enzyme. Strategies for such DNA shuffling are known in the art. See, for example, Stemmer (1994) Proc. Natl. Acad. Sci. USA 91:10747–10751; Stemmer (1994) Nature 370:389–391; Crameri et al. (1997) Nature Biotech. 15:436–438; Moore et al. (1997) J. Mol. Biol. 272:336–347; Zhang et al. (1997) Proc. Natl. Acad. Sci. USA 94:4504–4509; Crameri et al. (1998) Nature 391:288–291; and U.S. Pat. Nos. 5,605,793 and 5,837,458.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledonous plants or dicotyledonous plants as these preferences have been shown to differ (Murray et al. (1989) *Nucl. Acids Res.* 17:477–498). Thus, the maize preferred codon for a particular amino acid may be derived from known gene sequences from maize. Maize codon usage for 28 genes from maize plants are listed in Table 4 of Murray et al., supra.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell that contains a vector and supports the replication and/or expression of the expression vector. Host cells may be prokaryotic cells such as *E. coli,* or eukaryotic cells such as yeast, insect, amphibian, or mammalian cells. Preferably, host cells are monocotyledonous or dicotyledonous plant cells, including but not limited to maize, sorghum, sunflower, soybean, wheat, alfalfa, rice, cotton, and tomato. A particularly preferred monocotyledonous host cell is a maize host cell.

The term "hybridization complex" includes reference to a duplex nucleic acid structure formed by two single-stranded nucleic acid sequences selectively hybridized with each other.

As used herein, "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, "polynucleotide" includes reference to a deoxyribopolynucleotide, ribopolynucleotide, or analogues thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically, or metabolically modified forms of polynucleotides, as well as the chemical forms of DNA and RNA characteristic of viruses and cells, including inter alia, simple and complex cells.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria that comprise genes expressed in plant cells, such as Agrobacterium or Rhizobium. Examples are promoters that preferentially initiate transcription in certain tissues, such as leaves, roots, seeds, fibers, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Another type of promoter is a developmentally regulated promoter. For example, a promoter that drives expression during pollen development. Tissue-preferred, cell type specific, developmentally regulated, and inducible promoters constitute the class of "non-constitutive" promoters. A "constitutive" promoter is a promoter that is active under most environmental conditions. Constitutive promoters are known in the art and include, for example, 35S promoter (Meyer et al. (1997) *J. Gen. Virol.* 78:3147–3151); ubiquitin; as well as those disclosed in U.S. Pat. Nos. 5,608,149; 5,608,144; 5,604,121; 5,569,597; 5,466,785; 5,399,680; 5,268,463; 5,608,142.

As used herein, "recombinant" includes reference to a cell or vector that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, underexpressed, or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40 to 80% sequence identity, preferably 90% sequence identity, and most preferably 100% sequence identity (i.e., complementary) with each other.

The nucleotide sequences of the invention can be used to isolate corresponding sequences from other organisms. In this manner, methods such as PCR, hybridization, and the like can be used to identify such sequences based on their sequence homology to the sequences set forth herein. Sequences isolated based on their sequence identity to the entire fumonisin-degrading coding sequences or to the catabolic gene cluster sequence set forth herein or to fragments thereof are encompassed by the present invention.

In a PCR approach, oligonucleotide primers can be designed for use in PCR reactions to amplify corresponding DNA sequences from cDNA or genomic DNA extracted from any organism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the fumonisin-degrading coding sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire fumonisin-degrading nucleotide sequence or the entire fumonisin catabolic gene cluster sequence disclosed herein, or one or more portions thereof, may be used as a probe capable of specifically hybridizing to corresponding fumonisin-degrading sequences and messenger RNAs. To achieve specific hybridization under a variety of conditions, such probes include sequences that are unique among fumonisin-degrading sequences and are preferably at least about 10 nucleotides in length, and most preferably at least about 20 nucleotides in length. Such probes may be used to amplify corresponding fumonisin-degrading sequences from a chosen organism by PCR. This technique may be used to isolate additional coding sequences from a desired plant organism or as a diagnostic assay to determine the presence of coding sequences in a plant an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2× SSC (20× SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1× SSC at 55 to 60° C. Exemplary high stringency conditions include hybridization in 50% formamide, 1 M NaCl, 1% SDS at 37° C., and a wash in 0.1× SSC at 60 to 65° C.

Specificity is typically the function of post-hybridization washes, the critical factors being the ionic strength and temperature of the final wash solution. For DNA—DNA hybrids, the $T_m$ can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology— Hybridization with Nucleic Acid Probes,* Part I, Chapter 2 (Elsevier, N.Y.); and Ausubel et al., eds. (1995) *Current Protocols in Molecular Biology,* Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

In general, sequences that encode for a fumonisin-degrading protein and hybridize to the fumonisin-degrading sequences or the sequences of the fumonisin catabolic gene cluster disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Optimal alignment of sequences for comparison may be conducted by the local homology algorithm of Smith et al. (1981) *Adv. Appl. Math.* 2:482; by the homology alignment algorithm of Needleman et al. ( 1970) *J. Mol. Biol.* 48:443; by the search for similarity method of Pearson et al. (1988) *Proc. Natl. Acad. Sci.* 85:2444; by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Drive, Madison, Wis., USA; the CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *Computer Applications in the Biosciences* 8:155–65, and Person et al. (1994) *Meth. Mol. Biol.* 24:307–331; preferred computer alignment methods also include the BLASTP, BLASTN, and BLASTX algorithms (see Altschul et al. (1990) *J. Mol. Biol.* 215:403–410). Alignment is also often performed by inspection and manual alignment.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman et al. (1970) *J. Mol. Biol.* 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

As indicated, the enzymes and nucleotide sequences encoding such enzymes are involved in the degradation of fumonisin and fumonisin-like compounds. Such enzymes and nucleotide sequences can be utilized alone or in combination to engineer microbes or other organisms to completely metabolize fumonisin and resist its toxic effects. That is, at least one of the genes of the invention can be used to transform a host cell of interest. Alternatively, the entire fumonisin catabolic cluster can be cloned into the host cell. Methods for cloning gene clusters into a plasmid, a cosmid or a Bac are known in the art. The cloned cluster can then be moved to the host cell of interest, generally another microorganism or yeast cell. Under suitable induction conditions, the pathway will be activated and fumonisin degraded. See, for example, Prieto et al. (1996) *J. Bacteriol.* 178(1):111–120, herein incorporated by reference.

Fumonisin is produced in the intercellular spaces (apoplast) of Fusarium-infected maize cells. Thus, the apoplast is the preferred location for esterase and possibly other catabolic enzymes. It is possible that some fumonisin could diffuse or be transported into the maize cells before it is broken down by the apoplastic enzymes and may escape catabolism. Thus, it may be beneficial to express a fumonisin pump in such cells. In this manner, any fumonisin entering the cell will be pumped out and reexposed to catabolic enzymes. Similar toxin pumps exist in other toxin-producing fungi that show resistance to toxins or antibiotics.

The enzymes from Bacterium 2412.1 involved in the degradation of fumonisin are provided in Table 1. Additionally, they are discussed briefly below.

fccA Esterase:

This esterase, also known as BacEst, was previously shown to hydrolyze the tricarballylate esters of fumonisins. This enzyme is the bacterial homolog of the *Exophiala spinifera* esterase, ESP1.

fccB Citrate/Tricarballylate Transport Protein:

This protein may be necessary to break down the tricarballylic acid resulting from hydrolysis of fumonisin by the esterase. The citrate/tricarballylate transporter can be used to transport the tricarballylic acid into the cell where it may be able to be broken down by endogenous enzymes. Additional enzymes that may be discovered could be used as well to effect the removal of tricarballylate once it is in the cell.

fccC Flavin Monooxygenase:

This enzyme has homology to monooxygnease that act on keto or quinone groups, oxidizing them to a carboxylate with carbon chain breakage. In our detoxification strategy, it may be necessary to provide more complete catabolism of fumonisin in transgenic maize or other transgenic organisms than can be provided by esterase and deaminase enzymes. If so, the monooxygenase activity of this clone is predicted to result in the oxidation of 2-OP to a compound that would lack a keto group, having instead a terminal aldehyde group, or possibly a carboxylate group. This is due to a type of enzymatic oxidation referred to as Baeyer-Villiger oxidation, in which monooxygen is inserted adjacent to a keto function, resulting in a lactone or ester linkage (Walsch & Chen, Angew. Chem. Int Ed. Engl 27 (1988) 333–343). The metabolism of trans-cyclohexane-1,2 diol by Acinetobacter provides a model for the activity of a Baeyer-Villiger monooxygenase on 2-OP (Davey & Trudgill, 1977, Eur. J. Biochem 74:115–127). This diol is first oxidized to ortho hydroxy cyclohexanone by a different enzyme, and then a monooxygen is inserted between the quione and hydroxy functions by the Baeyer-Villiger enzyme, cyclohexanone monooxygenase. This intermediate spontaneously rearranges to a linear aldehyde carboxylic acid. By analogy, for 2-OP we would predict insertion of oxygen between carbons 2 and 3 and then spontaneous cleavage to a C22 aldehyde and acetic acid. Further oxidation by an aldehyde dehydrogenase would convert this compound to a carboxylic acid; other transformations would also be possible given the high reactivity of the aldehyde group.

TABLE 1

| Gene | Nucleotides | Frame | Predicted ORF Size | BLASTP Homology | Functional Class |
|---|---|---|---|---|---|
| fccA | 13803 to 15389 | +3 | 529 aa | Esterase | Metabolism |
| fccB | 15627 to 16913 | +3 | 429 aa | Citrate Transport | Transport |
| fccC | 19074 to 20747 | +3 | 558 aa | Flavin monoox | Metabolism |
| fccD | 11698 to 10295 | −3 | 468 aa | Aldehyde dehydrogenase | Metabolism |
| fccE | 6435 to 7370 | +3 | 312 aa | Alcohol dehydrogenase | Metabolism |
| fccF | 7814 to 9187 | +2 | 458 aa | Co-A Ligase | Metabolism |
| fccG | 13474 to 11774 | −2 | 567 aa | Acetohydroxy acid synthase | Metabolism |
| fccH | 24222 to 21361 | −3 | 954 aa | B12 Transport | Transport |
| fccI | 17189 to 18487 | −2 | 433 aa | Permease | Transport |
| fccJ | 9317 to 10225 | +2 | 303 aa | Cat Transcription Factor | Regulatory |
| fccK | 3723 to 5111 | +3 | 463 aa | Aspartae Oxidase (Fumarate Reductase) | Metabolism |
| fccL | 979 to 3381 | +1 | 801 aa | TonB Dependent Receptor | Transport |
| fccM | 15557 to 14394 | −1 | 391 aa | N-methyl transferase | Metabolism |
| fccN | 5104 to 6282 | +1 | 393 aa | Cit-B homolog | Metabolism |
| fccO | 10892 to 11368 | +2 | 159 aa | Car 2 comp Regulatory Protein | Regulatory |
| fccE | 3408 to 2353 | −3 | 352 aa | Possible Flavoenzyme | Metabolism |
| fccQ | 229 to 705 | +1 | 159 aa | LRP Regulatory Protein | Regulatory |
| fccR | 8926 to 7854 | −2 | 358 aa | Unknown | ? |
| fccS | 2221 to 1660 | −1 | 183 aa | Unknown | ? |
| fccT | 1590 to 1060 | −1 | 177 aa | Unknown | ? |

fccD Aldehyde Dehydrogenase:

One likely product of flavin monooxygenase oxidation of 2-OP is a C-20 aldehyde (see above); if so, we would predict that an aldehyde dehyrogenase would be available to oxidize the aldehyde to a carboxylate group, as a prerequisite to insertion into the beta-oxidation pathway for catabolism to acetyl co-A.

fccE Alcohol Dehydrogenase:

This gene shows homology to members of the short-chain dehydrogenase (SD) class of oxidoreductases, designated in Prosite as group PSO-00060. This class contains many NADP or NAD+ requiring alcohol dehydrogenases as well as anabolic enzymes that convert 2-keto Co-A acid esters to -corresponding alcohols. This enzyme may be responsible for oxidation of the C-5, alcohol of the carboxylate to a keto group, which would result in an alpha keto acid that could be further degraded by beta-oxidation. The enzyme could also oxidize hydroxyls at C13 and C14 to ketones, allowing a monooxygenase such as that described above to further oxidize and fragment the carbon chain. It is also possible that this enzyme attacks the C5 hydroxyl of AP1. Since the C-5 hydroxyl group of AP1 is considered important for toxicity, this enzyme may be useful in detoxification of AP1.

fccF CoA Ligase:

This enzyme may provide conjugation of a fumonisin-derived carboxylic acid with coenzyme A, prior to beta-oxidation.

fccG Acetohydroxyacid Synthase:

This gene may code for a protein that provides a pH stat when fumonisin metabolites are being metabolized.

fccH Vitamin B12 Receptor:

This receptor possibly plays a role in membrane transport of breakdown products or import of cofactors needed for enzymes in the pathway.

fccI Permease:

This protein is expected to have a role in the transport of metabolites into the cells, or exclusion of fumonisin.

fccJ Regulatory Protein:

Similar to LysR regulatory protein from *E. coli*, this protein probably functions to suppress transcription of pathway genes until the appropriate stimulus (i.e., fumonisin or AP1 or TCA) is present.

fccK Fumarte Reductase (Aspartate Oxidase):

This gene encodes a redox enzyme homolog that may oxidize the C-2 amine of AP1 and/or fumonisin.

fccL TonB Dependent Receptor:

This protein is involved in iron uptake.

FccM:

This protein has homology to an N-methyl transferase and may be involved in antibiotic resistance. In addition, it may also function in methylating FB1 or AP1 to reduce toxicity.

FccN:

The fccN gene encodes a citrate utilization B protein.

FccO Carbohydrate Regulatory Protein:

This protein may be involved in the regulation of carbohydrate pathways. It may also down-regulate genes for non-fumonisin catabolysis or may be involved in regulating gene expression in the fumonisin cluster.

FccP:

This gene is contained within the antisense strand of fccl and may encode a flavoenzyme. The protein may be an AP1/FB1 deaminating enzyme based on similarity to flavoenzymes which include amine oxidases.

FccQ Leucine Responsive Regulatory Protein:

This protein may be involved in regulation of catabolic gene expression.

FccR, FccS, FccT:

These proteins show no significant homology to other known proteins.

Compositions of the invention include the native nucleotide sequences for the catabolic genes, as well as variants and modifications thereof. It is recognized that having elucidated the pathway for fumonisin catabolism in Bacterium 2412.1, such DNA sequences can be inserted into expression cassettes and used to transform a variety of organisms. Enzymes produced recombinantly may be tested for their ability to modify fumonisin, fumonisin-related toxins, or a fumonisin byproduct using labeled starting material and appropriate buffer and cofactor conditions. For example, to test aldehyde dehydrogenase activity, the aldehyde dehydrogenase produced in a recombinant manner would be incubated with cofactors, NAD+ or NADP+, and $^{14}C$-labeled 2-OP for various times and then an aliquot of the reaction mix spotted on TLC. Enzyme activity would be indicated by the appearance of a new radiolabeled spot at a different Rf on the TLC plate. Compositions of the invention include the native nucleotide sequences for the catabolic genes and the fumonisin gene cluster, as well as variants and modifications thereof. Particularly, the nucleotide sequences, or fragments thereof, of SEQ ID NOS: 1, 2, 4, 6, 8, 10, 12, 14, 16, 18, 20, 22, 24, 26, 28, 30, 32, 34, 36, 38 and 40 can be utilized to isolate and/or synthesize full-length DNA sequences. Methods are known in the art for cloning of full-length cDNAs. Such techniques include, for example, RACE-PCR using oligonucleotide primers based on the known sequence, or cDNA library screening with labeled cDNA as probe, or by means of PCR of genomic DNA using a gene-specific probe and end-ligated primers (e.g., Genome Walker™ Clontech). It is recognized that having elucidated the pathway for fumonisin catabolism in Exophiala, such DNA sequences can be inserted into expression cassettes and used to transform a variety of organisms. Enzymes produced recombinantly may be tested for their ability to modify fumonisin or a fumonisin byproduct using labeled starting material and appropriate buffer and cofactor conditions. For example, to test aldehyde dehydrogenase activity, the aldehyde dehydrogenase produced in a recombinant manner would be incubated with cofactors, NAD+ or NADP, and $^{14}C$ -labeled 2-OP for various times and then an aliquot of the reaction mix spotted on TLC. Enzyme activity would be indicated by the appearance of a new radiolabeled spot at a different Rf on the TLC plate.

The sequences of the invention can be introduced into any host organism. The sequences to be introduced may be used in expression cassettes for expression in the host of interest where expression in the host is necessary for transcription.

One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The marker gene confers a selectable phenotype on the transformed cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance; the hygromycin phosphotransferase (HPT) gene coding for hygromycin resistance, genes coding for resistance to herbicides which act to inhibit the action of acetolactate synthase (ALS), in particular the sulfonylurea-type herbicides (e.g, the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, and the ALS gene encodes resistance to the herbicide chlorsulfuron.

The transcriptional initiation region, the promoter, may be native or analogous or foreign or heterologous to the host as well as to the coding sequence. Additionally, the promoter may be the natural sequence or alternatively a synthetic sequence. By foreign it is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in the host. The termination region may be native with the transcriptional initiation region, may be native with the DNA sequence of interest, or may be derived from another source. For use in plants or plant cells, convenient termination regions are available from the Ti-plasmid of *A. tumefaciens,* such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell.* 2:1261–1272; Munroe et al. (1990) *Gene* 91:151–158; Ballas et al. (1989) *Nucleic Acids Res.* 17:7891–7903; Joshi et al. (1987) *Nucleic Acids Res.* 15:9627–9639.

Nucleotide sequences of the invention are provided in expression cassettes for expression in the host cell of interest. The cassette will include 5' and 3' regulatory sequences operably linked to the sequence of interest. The cassette may additionally contain at least one additional sequence to be cotransformed into the organism. Alternatively, the additional sequence(s) can be provided on another expression cassette.

Where appropriate, the gene(s) may be optimized for increased expression in the transformed plant. That is, the genes can be synthesized using plant-preferred codons for improved expression. Methods are available in the art for synthesizing plant-preferred genes. See, for example, U.S. Pat. Nos. 5,380,831, 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) *PNAS USA* 86:6126–6130); potyvirus leaders, for example, TEV leader (Tobacco Etch Virus) (Allison et al. (1986); MDMV leader (Maize Dwarf Mosaic Virus); *Virology* 154:9–20), and human immunoglobulin heavy-chain binding protein (BiP), (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA,* ed. Cech (Liss, New York), pp. 237–256); and maize chlorotic mottle virus leader (MCMV) (Lommel et al. (1991) *Virology* 81:382–385). See also, Della-Cioppa et al. (1987) *Plant Physiol.* 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

In the same manner, a plant can be transformed with the nucleotide sequences of the invention to provide complete detoxification of fumonisin in the transformed plant and plant products. Such plants include, for example, species from the genera Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea, Caco, and Populus.

As used herein, “transgenic plant” includes reference to a plant that comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, nonrecombinant viral infection, nonrecombinant bacterial transformation, nonrecombinant transposition, or spontaneous mutation.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055), direct gene transfer (Paszkowski et al. (1984) *EMBO J.* 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in *Plant Cell, Tissue, and Organ Culture: Fundamental Methods,* ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods,* ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (*London*) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues,* ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75 :407–413 (rice); Osjoda et al. (1996) *Nature Biotechnology* 14:745–750 (maize via *Agrobacterium tumefaciens*); all of which are herein incorporated by reference.

The modified plant may be grown into plants in accordance with conventional ways. See, for example, McCormick et al. (1986) *Plant Cell. Reports* 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

The degradative enzymes can be fermented in a bacterial host and the resulting bacteria processed and used as a microbial spray. Any suitable microorganism can be used for this purpose. See, for example, Gaertner et al. (1993) in *Advanced Engineered Pesticides,* Kim (Ed.).

The genes of the invention can be introduced into microorganisms that multiply in plants (epiphytes) to deliver enzymes to potential target crops. Epiphytes can be gram-positive or gram-negative bacteria, or fungi, for example.

The microorganisms that have been genetically altered to contain at least one degradative gene and protein may be used for protecting agricultural crops and products. In one aspect of the invention, whole, i.e., unlysed, cells of the transformed organism are treated with reagents that prolong the activity of the enzyme produced in the cell when the cell is applied to the environment of a target plant. A secretion signal sequence may be used in combination with the gene of interest such that the resulting enzyme is secreted outside the host cell for presentation to the target plant.

It may be preferable to provide for secretion of certain of the enzymes while providing for others to remain in the cytoplasm or targeted to organelles such as, for example, the chloroplast. Generally, the first two gene products, the carboxylesterase and the flavin amine oxidase will be secreted. Secretion leaders are known in the art. Plant signal sequences, including, but not limited to, signal-peptide encoding DNA/RNA sequences which target proteins to the extracellular matrix of the plant cell (Dratewka-Kos et al., (1989) *J. Biol. Chem.* 264:4896–4900), the *Nicotiana plumbaginifolia* extension gene (DeLoose, et al. (1991) *Gene* 99:95–100), signal peptides which target proteins to the vacuole like the sweet potato sporamin gene (Matsuka et al. (1991) *PNAS* 88:834) and the barley lectin gene (Wilkins et al. (1990) *Plant Cell* 2:301–313), signal peptides which cause proteins to be secreted such as that of PRIb (Lind et al. (1992) *Plant Mol. Biol.* 18:47–53), or the barley alpha amylase (BAA) (Rahmatullah et al. (1989) *Plant Mol. Biol.* 12:119) and hereby incorporated by reference, or from the present invention the signal peptide from the ESP1 or BEST1 gene, or signal peptides which target proteins to the plastids such as that of rapeseed enoyl-Acp reductase (Verwaert et al. (1994) *Plant Mol. Biol.* 26:189–202) are useful in the invention. Such secretion signal sequences can be used in expression cassettes to provide for secretion of the protein of interest outside the cell.

The remaining gene products are provided in the cell. These enzymes include a flavin monooxygenase, an aldehyde dehydrogenase and an alcohol dehydrogenase. The expression cassettes for the corresponding genes may contain an organellar targeting sequence. In plants, for example, a chloroplast targeting sequence may be used.

In this manner, at least one of the genes encoding a fumonisin-degradation enzyme of the invention may be introduced via a suitable vector into a microbial host, and said transformed host applied to the environment or plants or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the polypeptide, and, desirably, to provide for improved protection of the enzymes of the invention from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Pichia, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli,* and *Azotobacter vinlandii;* and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pullulans.*

Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spiritlum; Lactobacillaceae; Pseudomonadaceae, such as Pseudomonas and Acetobacter; Azotobacteraceae; and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, Pichia and the like.

Characteristics of particular interest in selecting a host cell for purposes of production include ease of introducing the protein gene into the host, availability of expression systems, efficiency of expression, stability of the protein in the host, and the presence of auxiliary genetic capabilities. Other considerations include ease of formulation and handling, economics, storage stability, fermentation suitability, and the like.

A number of ways are available for introducing a gene expressing the degradation enzyme into the microorganism host under conditions that allow for stable maintenance and expression of the gene. For example, expression cassettes can be constructed that include the DNA constructs of interest operably linked with the transcriptional and translational regulatory signals for expression of the DNA constructs, and a DNA sequence homologous with a sequence in the host organism, whereby integration will occur, and/or a replication system that is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. supra; Maniatis et al., eds. (1982) *Molecular Cloning: A Laboratory Manual* (Cold Spring Harbor Laboratory, Cold Spring Harbor, N.Y.); Davis et al., eds. (1980) *Advanced Bacterial Genetics* (Cold Spring Harbor Laboratory, Cold Spring Harbor, N.Y.); and the references cited therein.

It is recognized that the construction of a catabolic pathway in a transformed organism is a complicated feat. Therefore, any means for assembling the enzymes of interest into an organism of interest is encompassed. For example, a single polynucleotide sequence encoding all of the desired enzymes or multiples thereof may be transformed into the host organism. When microorganisms are to be applied to the environment or to a plant, several microorganisms, each transformed with one, two, three, or more nucleotide sequences of the invention, may be utilized. In this manner, all of the enzymes necessary to bring about detoxification of fumonisin and related products may be presented to the environment or to the plant by applying a mixture of transformed organisms or a single organism capable of expressing the entire pathway or at least expressing enough of the pathway to detoxify fumonisin.

In plants, nucleotide sequences for an enzyme may be transformed into a plant and crossed with plants expressing a different enzyme. In this manner, progeny can be obtained having the entire sequence or enough of the sequence to detoxify fumonisin. Alternatively, a plant can be transformed with nucleotides encoding several enzymes at the same time. In some tissue culture systems it is possible to transform callus with one nucleotide sequence, establish a stable culture line, and then transform the callus a second time with a second nucleotide sequence. The process may be repeated to introduce additional sequences.

To facilitate the expression of more than one enzyme in a cell, e.g. a plant cell, fusion proteins may be created. Generally, a spacer region is included between the proteins. The spacer region may comprise a cleavage site for cleavage by an endogenous or introduced protease.

The present invention also relates to a method of detoxifying a fumonisin or a structurally related mycotoxin with the enzymes from Bacterium 2412.1 during the processing of grain for animal or human food consumption, during the processing of plant material for silage, or food crops contaminated with a toxin-producing microbe, such as but not limited to, tomato. Since the atmospheric ammoniation of corn has proven to be an ineffective method of detoxification (see Haumann (1995) *INFORM* 6:248–257), such a methodology during processing is particularly critical where transgenic detoxification is not applicable.

In this embodiment, the fumonisin degradative enzymes found in Bacterium 2412.1, are presented to grain, plant material for silage, or a contaminated food crop, or during the processing procedure, at the appropriate stages of the procedure and in amounts effective for detoxification of fumonisins and structurally related mycotoxins. Detoxification by this method can occur not only during the processing, but also any time prior to or during the feeding of the grain or plant material to an animal or incorporation of the grain or food crop into a human food product, or before or during ingestion of the food crop.

The active ingredients of the present invention are normally applied in the form of compositions and can be applied to the crop area or plant to be treated, simultaneously or in succession, with other compounds. These compounds can be both fertilizers or micronutrient donors or other preparations that influence plant growth. They can also be selective herbicides, insecticides, fungicides, bactericides, nematicides, mollusicides, or mixtures of several of these preparations, if desired, together with further agriculturally acceptable carriers, surfactants, or application-promoting adjuvants customarily employed in the art of formulation. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers.

The enzymes can be introduced during processing in appropriate manners, for example as a wash or spray, or in dried or lyophilized form or powered form, depending upon the nature of the milling process and/or the stage of processing at which the enzymatic treatment is carried out. See generally, Hoseney (1990) *Principles of Cereal Science and Technology* (American Association of Cereal Chemists, Inc.) especially Chapters 5, 6, and 7; Jones (1992) *Food Safety* (Eagan Press, St. Paul, Minn.) especially Chapters 7 and 9; and Jelen (1985) *Introduction to Food Processing* (Restan Publishing Company, Reston, Va.). Processed grain or silage to be used for animal feed can be treated with an effective amount of the enzymes in the form of an inoculant or probiotic additive, for example, or in any form recognized by those skilled in the art for use in animal feed. The enzymes of the present invention are expected to be particularly useful in detoxification during processing and/or in animal feed prior to its use, since the enzymes display relatively broad ranges of pH activity. The esterase enzymes from *Exophiala spinifera,* American Type Culture Collection Accession No. 74269, showed a range of activity from about pH 3 to about pH 7 (U.S. Pat. No. 5,716,820, supra). The APAO enzyme from *Exophiala spinifera,* American Type Culture Collection Accession No. 74269 has a pH range of activity from pH 5 to pH 10. While not limited thereto, it is expected that the enzymes of the present invention will exhibit similar activity.

In another embodiment, ruminal microorganisms can be genetically engineered to contain and express at least one of the fumonisin degradation enzymes of the invention. The genetic engineering of microorganisms is now an art-recognized technique, and ruminant microorganisms so engineered can be added to feed in any art recognized manner, for example as a probiotic or inoculant. In addition, microorganisms, plants, or other organisms or their cultured cells in vitro capable of functioning as bioreactors can be engineered so as to be capable of mass producing the fumonisin degrading enzymes of the invention. Cite use of Bacterium 2412.1 itself, engineered to express these enzymes constitutively by manipulating regulatory factors, e.g. fccJ (LysR homolog).

Another embodiment of the present invention is the use of the enzymes of the present invention as detection reagents for fumonisins and related compounds. The enzymes of the present invention can be used as detection reagents because of the high specificity of the esterase and deaminase enzymes, and the fact that hydrolysis followed by amine oxidation can be monitored by detection of hydrogen peroxide or ammonia using standard reagents (analogous to a glucose detection assay using glucose oxidase). Hydrogen peroxide is often measured by linking a hydrogen peroxide-dependent peroxidase reaction to a colored or otherwise detectable peroxidase product (e.g., Demmano et al. (1996) *European Journal of Biochemistry* 238(3):785–789). Ammonia can be measured using ion-specific electrodes: Fritsche et al. (1991) *Analytica Chimica Acta* 244(2):179–182; West et al. (1992) *Analytical Chemistry* 64(5):533–540, and all herein incorporated by reference) or by GC or other chromatographic method.

For example, recombinant or non-recombinant, active fumonisin esterase, APAO, and proteins of the invention are added in catalytic amounts to a sample tube containing an unknown amount of fumonisins (FB1, FB2, FB3, FB4, or partial or complete hydrolysis products of these). The tube is incubated under pH and temperature conditions sufficient to convert any fumonisin in the sample to AP1, the AP1 to 2-OP, ammonia, and hydrogen peroxide, and to further degradation products. Then suitable reagents are added for quantification of the hydrogen peroxide or ammonia that were generated stoichiometrically from fumonisins. By comparison with control tubes that received no esterase or APAO enzyme, the amount of fumonisin present can be calculated in direct molar proportion to the hydrogen peroxide or ammonia detected, relative to a standard curve.

This invention can be better understood by reference to the following nonlimiting examples. It will be appreciated by those skilled in the art that other embodiments of the invention may be practiced without departing from the spirit and the scope of the invention as herein disclosed and claimed.

EXPERIMENTAL

EXAMPLE 1

Bacterial isolates

Bacterium 2412.1 isolates from maize were isolated as described in U.S. Pat. No. 5,716,820 and pending U.S. application Ser. Nos. 08/888,949 and 08/888,950, both filed Jul. 7, 1997, and herein incorporated by reference.

Alkaline hydrolysis of FB1 to AP1

FB1 or crude fumonisin $C_8$ material was suspended in water at 10–100 mg/ml and added to an equal volume of 4 N NaOH in a screw-cap tube. The tube was sealed and incubated at 60° C. for 1 hr. The hydrolysate was cooled to room temperature and mixed with an equal volume of ethyl acetate, centrifuged at 1000 RCF for 5 minute and the organic (upper) layer recovered. The pooled ethyl acetate layers from two successive extractions were dried under $N_2$ and resuspended in distilled $H_2O$. The resulting material (the aminopentol of FB1 or "AP1" was analyzed by TLC.

Analysis of Fumonisins and Metabolism Products

Analytical thin-layer chromatography was carried out on 100% silanized $C_{18}$ silica plates (Sigma #T-7020; 10×10 cm; 0.1 mm thick) by a modification of the published method of Rottinghaus (Rottinghaus et al. (1992) *J. Vet. Diagn. Invest.* 4:326, and herein incorporated by reference).

To analyze fumonisin esterase activity, sample lanes were pre-wet with methanol to facilitate sample application. After application of from 0.1 to 2 $\mu$l of aqueous sample, the plates were air-dried and developed in MeOH:4% KCl (3:2) or MeOH;0.2 M KOH (3:2) and then sprayed successively with 0.1 M sodium borate (pH 9.5) and fluorescamine (0.4 mg/ml in acetonitrile). Plates were air-dried and viewed under long-wave UV.

For analysis of APAO activity, an alternative method was used. Equal volumes of sample and $^{14}$C-AP1 (1 mg/ml, 50 mM Na-phosphate pH 8) substrate were incubated at room temperature for six days. Analytical thin-layer chromatography was then carried out on C60 HPK silica gel plates (Whatman #4807-700; 10×10 cm; 0.2 mm thick). After application of from 0.1 to 2 μl of aqueous sample, the plates were air dried and developed in $CHCl_3$:MeOH:$CH_3COOH$:$H_2O$ (55:36:8:1). Plates were then air dried, and exposed to PhosphorImager screen or autoradiographic film. A Storm PhosphorImager was used to scan the image produced on the screen.

EXAMPLE 2

Isolation of Fumonisin-Catabolizing Gene Cluster

A FB1 catabolizing esterase was identified in the culture supernatant of Bacterium 2412.1, and a gene (BacEst) was cloned from this bacterium. The gene exhibited fumonisin esterase activity similar to that of the black yeast esterase ESP1. Since FB1 is catabolized to $CO_2$ in this bacterium, other proteins involved in the breakdown and transport of fumonisin would also be present in induced cells of Bacterium 2412.1.

The identification and isolation of a fumonisin detoxification cluster in Bacterium 2412.1 has been accomplished. The BacEst and CTP genes as well as other structural genes and at least 3 regulatory genes have been cloned. Sequence analysis indicates that these genes code for a set of proteins that are involved in the further catabolism and transmembrane transport of fumonisin and its catabolic products (see Table 1 and FIG. 1). These proteins provide a catabolic pathway for the degradation of fumonisins, and could also be used to engineer a fumonisin-regulated gene transcription system.

In order to identify fumonisin catabolic genes other than bacterial esterase, it was noted that many bacterial pathway genes are clustered together on the bacterial chromosome often containing one or more operons. Both structural and regulatory genes that regulate transcription of individual pathway genes often are found in such clusters. A 4.3 kb genomic fragment from a lambda Zap II phage library, which contained a complete, functional fumonisin esterase gene (BacEst) and in addition a complete open reading frame coding for a citrate transport protein (CTP), predicted to be involved in transport of tricarballylate into the bacterium was cloned. Therefore, approximately 500 bp DNA subclones from the distal ends of this 4.3 kb fragment was used as $^{32}P$-radiolabeled probes to identify additional lambda clones from this portion of the bacterial chromosome (i.e. chromosome "walking"). The probes were designated as P-BacEst (SEQ ID NO: 54) (at the 5' end relative to BacEst direction of transcription), and P-CTP (SEQ ID NO: 55) (at the 3' end). A genomic library used earlier to clone BacEst (Sau3A partially digested DNA from 2412.1, size selected for 4 to 10 kb insert size, cloned into lambda Zap II from Strategene) was used. A series of overlapping clones was identified by plaque hybridization using both P-BacEST and P-CTP probes together, and these clones were characterized by PCR using combinations of primers from probes and from the vector flanking regions. An overlapping series of clones representing various amounts of sequence extending out from the original 4.3 kb fragment was chosen based on a novel PCR screening method in which phage lysates were subjected to PCR with vector primers and probe-specific primers, in order to gauge the degree of overlap and extension. Phagemids chosen in this way were excised from lambda phage, plasmid DNA prepared from standard plasmid mini-preps and sequenced. For a second round of walking, distal probes (SEQ ID NOS: 56 and 57) were prepared from both ends of the longest 5' and 3' sequence obtained in the first round and library screening was repeated.

A 100 mL culture of bacterium 2412.1 was grown to saturation in LB broth and high molecular weight genomic DNA was isolated using standard methods (Short Protocols in Molecular Biology, $2^{nd}$ Ed., pp.2–11). The genomic DNA was digested with BamHI and dephosphorylated with Shrimp Alkaline Phosphatase.

The SuperCos I Cosmid Vector Kit (Stratagene) was used for library construction. The SCosI vector was digested with XbaI, dephosphorylated with Shrimp Alkaline Phosphatase, then digested with BamHI. The genomic DNA was ligated into the SCosI vector then packaged into XLI-Blue MR *E. coli* cells. The primary cosmid library was titered at 50 cfu/uL with a total of 30,000 cfu's. Cosmid DNA was prepared from eight colonies and digested with NotI to excise the inserts to estimate insert size. Average insert size was 27 kb with a range of 17.5–35kb. The primary library was amplified and titered at $2\times10^8$ cfu/mL.

Probes were made from the ends of the current BAM gene cluster and designated SCos_5' (SEQ ID NO: 58) and SCos_3' (SEQ ID NO: 59). The library was screened with 50,000 cfu's/plate using the SCos_5' probe and yielded 35 clones which hybridized to the SCos_5' probe. Inserts from these clones were excised using NotI which also produced smaller fragments of DNA from each clone. The fragments were then subcloned into the pSPORTI vector (GibcoBRL) that was previously digested with NotI and dephosphorylated.

The pSPORTI fragments were transformed into *E. coli* DH5a cells, DNA was miniprepped and digested with NotI to verify subclones with the correct inserts. The subclones were then sequenced with M13F and M13R primers to obtain DNA sequence from the ends of each subclone. Primer-walking was then used to fully sequence each subclone. The 8.5 kb subclone contigged with the 5'end of the BAM gene cluster.

Figure 2:
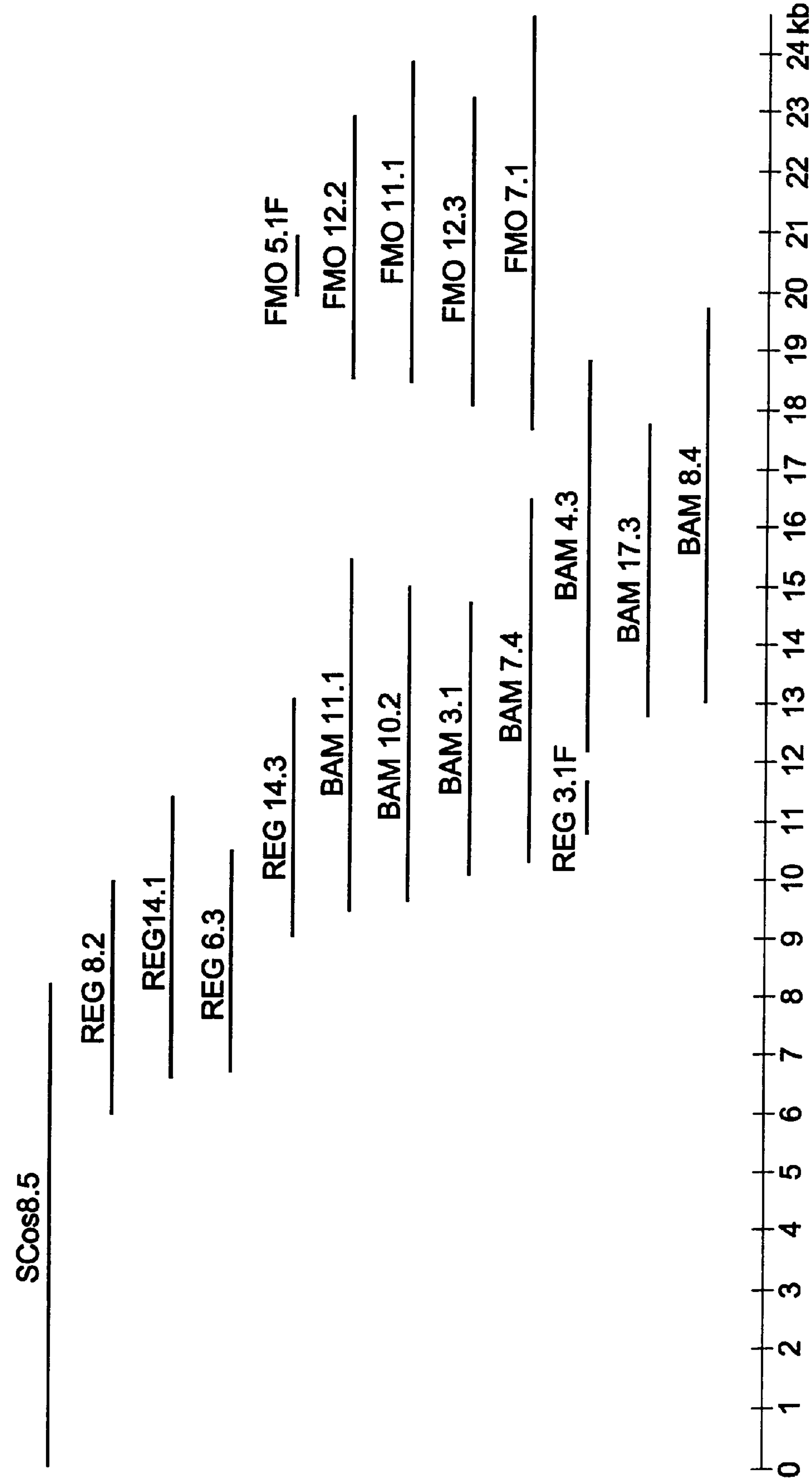
FIG. 2 illustrates the overlap of the individual lambda clones and cosmids which were sequenced to reconstruct the fumonisin catabolic gene cluster.

The individual lambda clones and cosmids were sequenced to the point of overlap, and a single large contig assembled from the various clones (FIG. 2). Table II summarizes the American Type Culture Collection deposits made containing the overlapping clones of the fumonisin catabolic gene cluster. The strain designation and their corresponding plasmids are provided.

TABLE 2

| STRAIN DESIGNATION | FRAGMENT | PLASMID |
|---|---|---|
| SuperCos_8.5_1 | SCos 8.5 | PSPORT1: SuperCos_8.5_1 |
| BAM_PL1 | BAM 4.3 | PBK-CMV:BAM 4.3 |
| | BAM 7.4 | PBK-CMV:BAM 7.4 |
| | BAM 8.4 | PBK-CMV:BAM 8.4 |
| | BAM 10.2 | PBK-CMV:BAM 10.2 |
| | BAM 11.1 | PBK-CMV:BAM 11.1 |
| | BAM 17.3 | PBK-CMV:BAM 17.3 |
| | BAM 3.1 | PBK-CMV:BAM 3.1.1 |
| BAM_PL2 | REG 6.3 | PBK-CMV:REG 6.3.1 |
| | REG 14.3 | PBK-CMV:REG 14.3.1 |
| | REG 14.1 | PBK-CMV:REG 14.1.1 |
| | REG 8.2 | PBK-CMV:REG 8.2.1 |
| | REG 3.1 | PBK-CMV:REG 3.1.1 |
| | FMO 12.3 | PBK-CMV:FMO 12.3.1 |
| | FMO 12.2 | PBK-CMV:FMO 12.2.1 |
| | FMO 7.1 | PBK-CMV:FMO 7.1.1 |
| | FMO 5.1 | PBK-CMV:FMO 5.1.1 |
| | FMO 11.1 | PBK-CMV:FMO 11.1.1 |

Figure 3:
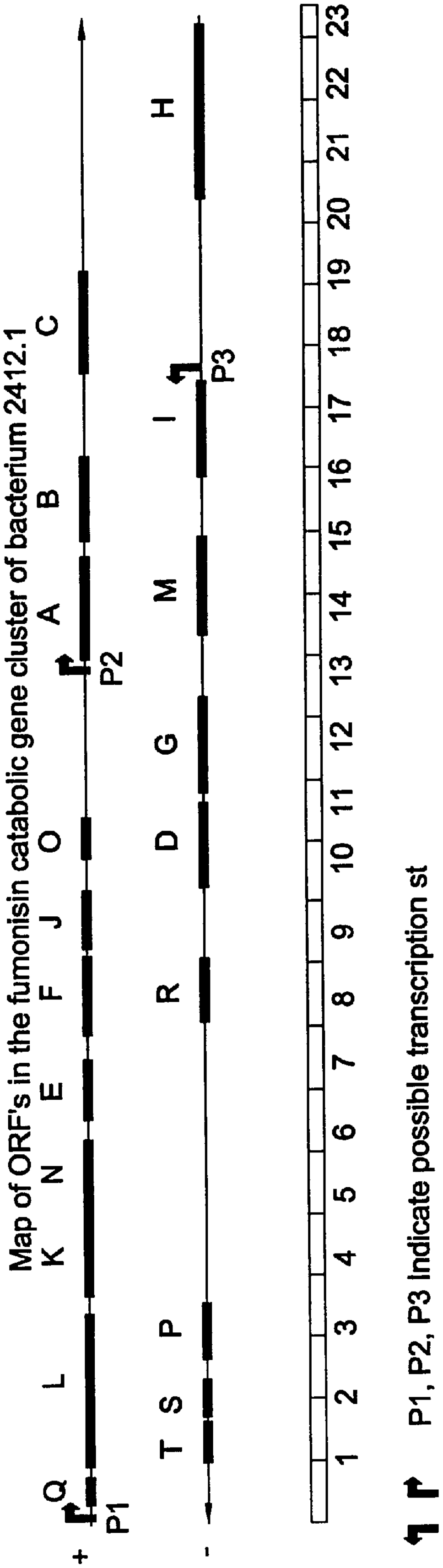
FIG. 3 provides a map of the open reading frames in the fumonisin catabolic gene cluster of bacterium 2412.1

The contig represents 24.5 kb of chromosomal DNA, and contains twenty open reading frames including the fumonisin esterase and citrate transport homolog. Most of the genes in this region have homology to genes known to function in carbon catabolic pathways that involve functional groups that would be expected to be utilized for fumonisin. These have been given appropriate designations as fccA through fccT (fumonisin catabolic cluster) (Table 1). One open reading frame, fccJ, has homology to negative regulatory genes controlling lysine degradation pathway (LysR) and could be the regulator that prevents transcription of genes in this cluster in the absence of substrate. Other open reading frames in this region may be involved in other cellular functions needed for effective catabolism of fumonisin. A map of the open reading frames in the fumonisin catabolic gene cluster of Bacterium 2412.1 is shown in FIG. 3.

Many of the gene functions deduced from ORFs in this cluster have also been identified among AP1-induced transcripts from *Exophiala spinifera* (see U.S. application Ser. Nos. 08/888,949; 08/888,950; and Table 2). These are, aside from the fumonisin esterase: flavin monooxygenase, aldehyde dehydrogenase, alcohol dehydrogenase, and transmembrane permease. A possible degradation pathway for fumonisins based on these enzyme activities is presented in FIG. 1. The functional similarity of bacterial fcc cluster genes and AP1-induced Exophiala cDNAs increases the likelihood that these genes are involved in fumonisin breakdown in the respective organisms.

To identify an open reading frame corresponding to a deaminating enzyme such as the AP1-specific amine oxidase identified as an induced transcript in *E. spinifera* (APAO) cosmid clones corresponding to flanking regions of the fcc cluster have been obtained. It is anticipated such a gene will be found in this flanking DNA. However, identification of this gene is not crucial to this invention, as we have demonstrated AP1 deaminating activity of the *Exophiala spinifera* cDNA for APAO in a bacterial expression system, so it is possible to engineer the fungal gene along with bacterial genes in this cluster to engineer a complete pathway.

cDNA sequences for a citrate/tricarballylate transport protein (fccB) (SEQ ID NO: 4); a flavin monooxygenase (fccC) (SEQ ID NO: 6); an aldehyde dehydrogenase (fccD) (SEQ ID NO: 8); an alcohol dehydrogenase (fccE) (SEQ ID NO: 10); a CoA ligase (fccF) (SEQ ID NO: 12); an acetohydroxyacid synthase (fccG) (SEQ ID NO: 14); a vitamin B12 receptor (fccH) (SEQ ID NO: 16); a permease (fccI) (SEQ ID NO: 18); and a regulatory protein (fccJ) (SEQ ID NO: 20); a fumarate reductase/aspartate oxidase (fccK) (SEQ ID NO: 22); a TonB dependent receptor (fccL) (SEQ ID NO: 24); a protein with homology to N-methyl transferase (fccM) (SEQ ID NO: 26); a citrate utilization B (fccN) (SEQ ID NO: 28); a carbohydrate regulatory gene (fccO) (SEQ ID NO: 30); a possible flavoenzyme (fccP) (SEQ ID NO: 32); a leucine regulatory protein homolog (fccQ) (SEQ ID NO: 34); fccR (SEQ ID NO:36); fccS (SEQ ID NO: 38); fccT (SEQ ID NO: 40) have been isolated. Such sequences are provided. An esterase (fccA) also known as BacEst has previously been described.

The complete 24.5 kb contig of SEQ ID NO: 1 is likely to code for all the regulatory, transport, and catabolic machinery needed to catabolize FB1 to nontoxic metabolites. A single full-length cosmid clone that contains all of these genes together in order to test this hypothesis. This can readily be done by screening a cosmid library with probes generated from sequence on both ends of the contig, and selecting clones that hybridized under stringent conditions to both probes. The cosmid-containing *E. coli* strain would then be evaluated for its ability to break down fumonisin or AP1 added to the culture medium.

EXAMPLE 3

Pichia Expression of Degradative Enzymes

For cloning into *Pichia pastoris* expression vector, pPicZalphaA, oligonucleotide primers can be designed that contain a 22 bp overlap of the 5' end (sense strand) and 3' end (antisense strand), respectively of the open reading frame from Bacterium 2412.1, including the stop codon. In addition, each oligo has a 5' extension with digestible restriction sites that allows cloning of the amplified insert in-frame both into EcoRI/NotI digested pPicZalphaA. pPicZalphaA is an *E. coli* compatible Pichia expression vector containing a functional yeast alpha factor secretion signal and peptide processing sites, allowing high efficiency, inducible secretion into the culture medium of Pichia.

Pichia can be transformed as described in Invitrogen Manual, Easy Select™ Pichia Expression Kit, Version B, #161219, with the enzyme polynucleotide of interest with either an intron added (negative control, no expression) or an intron not added (capable of making an active protein). The Pichia culture fluids and pellets are assayed for enzyme activity as described earlier.

The sample 50 UL cell pellets are resuspended in 150 UL cold 50 mM Na-phosphate, pH8.0 and divided into two fresh 500 UL tubes. One tube is kept on ice with no treatment, the pellet suspension, and one tube is used for lysis. An equal volume of 0.1 mm zirconia-silica beads is added to each tube. The tubes are BeadBeat™ for 15 seconds then cooled on ice 5 minutes. This is repeated three times. The crude lysate is then transferred to another tube for assay or lysate suspension.

The TLC assays are performed as follows:

samples:

1.) pellet suspensions ("PELL"); 10 uL
2.) lysate suspensions ("LYS"); 10 uL
3.) media controls-mixed 5 uL media with 5 uL crude bacterial enzyme (if available); 10 uL
4.) positive control-used crude bacterial enzyme (if available) undiluted; 10 uL
5.) substrate control-used 50 mM Na-phosphate, pH8.0; 10 uL a cofactor (if required) is added to each reaction mixture incubate 10 uL each sample+10 uL $^{14}C$-substrate (fumonisin, metabolite, or other potential substrate) (1 mg/mL, pH8) at room temperature spot 1.0 uL onto C18 and C60 TLC plates develop C18 plates in MeOH:4% KCl (3:2)

develop C60 plates in $CHCl_3$:MeOH:$CH_3COOH$:$H_2O$ (55:36:8:1)

air-dry plates expose plates to PhosphorScreen 2–3 days use Storm PhosphorImager (Molecular Dynamics) to develop images

EXAMPLE 4

Expression of Enzymes in *E. coli*

The vector for expressing the enzyme of interest is a prokaryotic glutathione S-transferase (GST) fusion vector for inducible, high-level intracellular expression of genes or gene fragments as fusions with *Schistosoma japonicum* GST. GST gene fusion vectors include the following features: a lac promoter for inducible, high-level expression; an internal lac $I_q$ gene for use in any *E. coli* host; and the thrombin factor Xa or PreScission Protease recognition sites for cleaving the desired protein from the fusion product. The insert of interest may be cloned into the 5' EcoRI site and a 3' NotI site allowing in-frame expression of the fusion peptide. Generation of such an insert is described in the previous example.

*E. coli* was transformed with the vector containing the coding sequence for the enzyme as described in BRL catalogue, Life Technologies, Inc., catalogue; Hanahan (1983) *J. Mol. Biol.* 166:557; Jessee et al. (1984) *J. Focus* 6:4; King et al. (1986) *Focus* 8:1, and hereby incorporated by reference. The transformed *E. coli* may be induced by addition of IPTG (isopropyl b-D-thiogalactopyranoside) for expression of the polypeptide of interest.

EXAMPLE 5

Transformation and Regeneration of Transgenic Plants

Figure 4:
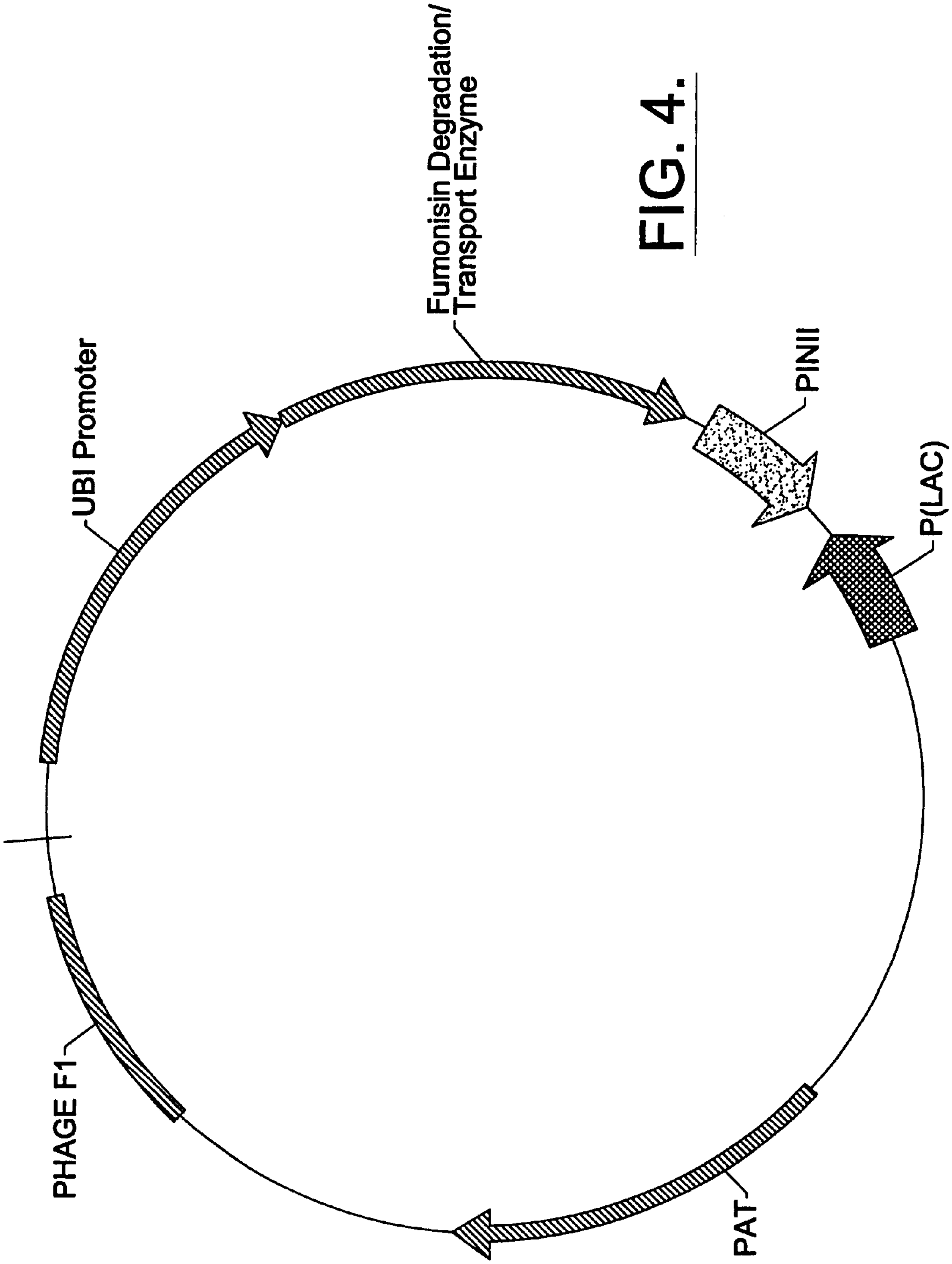
FIG. 4 schematically illustrates a plasmid vector comprising the gene for one of the fumonisin degradative enzymes of the invention operably linked to the ubiquitin promoter.

Immature maize embryos from greenhouse donor plants are bombarded with a plasmid containing the fumonisin-degradation/transporter enzyme nucleotide sequences operably linked to a ubiquitin promoter (FIG. 4). This plasmid also contains the selectable marker gene PAT (Wohlleben et al. (1988) *Gene* 70:25–37) that confers resistance to the herbicide Bialaphos. The preferred construct for expression in maize is the nucleotide sequence of the degradative enzyme either fused to the barley alpha amylase signal sequence or organellar targeting sequence, or left intact for expression in the cytoplasm. Transformation is performed as follows. All media recipes are in the Appendix.

Preparation of Target Tissue

The ears are surface sterilized in 30% Chlorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the fumonisin-degradation/transporter enzyme operably linked to the ubiquitin promoter is made. This plasmid DNA also contains a PAT selectable marker. The plasmid is precipitated onto 1.1 μm (average diameter) tungsten pellets using a $CaCl_2$ precipitation procedure as follows:

100 μl prepared tungsten particles in water
10 μl (1 μg) DNA in TrisEDTA buffer (1 μg total)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored for the expression of a fumonisin-degrading/transporter protein.

APPENDIX

APPENDIX

272 V

| Ingredient | Amount | Unit |
|---|---|---|
| D-I $H_2O$ | 950.000 | Ml |
| MS Salts (GIBCO 11117-074) | 4.300 | G |
| Myo-Inositol | 0.100 | G |
| MS Vitamins Stock Solution ## | 5.000 | Ml |
| Sucrose | 40.000 | G |
| Bacto-Agar @ | 6.000 | G |

Directions:
@=Add after bringing up to volume
Dissolve ingredients in polished D-I $H_2O$ in sequence
Adjust to pH 5.6
Bring up to volume with polished D-I $H_2O$ after adjusting pH
Sterilize and cool to 60° C.
=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.
Total Volume (L)=1.00

288 J

| Ingredient | Amount | Unit |
|---|---|---|
| D-I $H_2O$ | 950.000 | Ml |
| MS Salts | 4.300 | g |
| Myo-Inositol | 0.100 | g |
| MS Vitamins Stock Solution ## | 5.000 | ml |
| Zeatin .5 mg/ml | 1.000 | ml |
| Sucrose | 60.000 | g |
| Gelrite @ | 3.000 | g |
| Indoleacetic Acid 0.5 mg/ml # | 2.000 | ml |
| 0.1 mM Abscisic Acid | 1.000 | ml |
| Bialaphos 1 mg/ml # | 3.000 | ml |

Directions:
@=Add after bringing up to volume
Dissolve ingredients in polished D-I $H_2O$ in sequence
Adjust to pH 5.6

Bring up to volume with polished D-I $H_2O$ after adjusting pH

Sterilize and cool to 60° C.

Add 3.5g/L of Gelrite for cell biology.

=Dissolve 0.100 g of Nicotinic Acid; 0.020 g of Thiamine.HCL; 0.100 g of Pyridoxine.HCL; and 0.400 g of Glycine in 875.00 ml of polished D-I $H_2O$ in sequence. Bring up to volume with polished D-I $H_2O$. Make in 400 ml portions. Thiamine.HCL & Pyridoxine.HCL are in Dark Desiccator. Store for one month, unless contamination or precipitation occurs, then make fresh stock.

Total Volume (L)=1.00

560 R

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 30.000 | g |
| 2,4-D 0.5 mg/ml | 4.000 | ml |
| Gelrite @ | 3.000 | g |
| Silver Nitrate 2 mg/ml # | 0.425 | ml |
| Bialaphos 1 mg/ml # | 3.000 | ml |

Directions:

@=Add after bringing up to volume

#=Add after sterilizing and cooling to temp.

Dissolve ingredients in D-I $H_2O$ in sequence

Adjust to pH 5.8 with KOH

Bring up to volume with D-I $H_2O$

Sterilize and cool to room temp.

Total Volume (L)=1.00

560 Y

| Ingredient | Amount | Unit |
|---|---|---|
| D-I Water, Filtered | 950.000 | ml |
| CHU (N6) Basal Salts (SIGMA C-1416) | 4.000 | g |
| Eriksson's Vitamin Mix (1000X SIGMA-1511) | 1.000 | ml |
| Thiamine.HCL 0.4 mg/ml | 1.250 | ml |
| Sucrose | 120.000 | g |
| 2,4-D 0.5 mg/ml | 2.000 | ml |
| L-Proline | 2.880 | g |
| Gelrite @ | 2.000 | g |
| Silver Nitrate 2 mg/ml # | 4.250 | ml |

Directions:

@=Add after bringing up to volume

#=Add after sterilizing and cooling to temp.

Dissolve ingredients in D-I $H_2O$ in sequence

Adjust to pH 5.8 with KOH

Bring up to volume with D-I $H_2O$

Sterilize and cool to room temp.

Autoclave less time because of increased sucrose

Total Volume (L)=1.00

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule comprising a nucleotide sequence that encodes a fumonisin degradative enzyme, wherein said nucleotide sequence is selected from the group consisting of:

a) a nucleotide sequence that encodes a polypeptide having the amino acid sequence set forth in SEQ ID NO: 7; and b) the nucleotide sequence set forth in SEQ ID NO:6.

2. An expression cassette comprising a nucleic acid molecule of claim 1, wherein said nucleic acid molecule is operably linked to a promoter that drives expression in a plant cell.

3. The expression cassette of claim 2, wherein said promoter is a constitutive promoter.

4. An expression cassette comprising a nucleic acid molecule of claim 1, wherein said nucleic acid molecule is operably linked to a promoter that drives expression in a microorganism.

5. The expression cassette of claim 4, wherein said promoter is a constitutive promoter.

6. A vector for delivery of a nucleic acid molecule to a host cell, wherein said vector comprises a nucleic acid molecule of claim 1.

7. A host cell containing the vector of claim 6.

8. A host cell comprising in its genome at least one nucleic acid molecule of claim 1.

9. The host cell of claim 8, wherein said host cell is a cell of a plant selected from the group consisting of maize, sorghum, wheat, tomato, soybean, alfalfa, sunflower, Brassica, cotton, and rice.

10. A transformed plant cell having incorporated into its genome at least one nucleic acid molecule of claim 1.

11. A transformed plant having incorporated into its genome at least one nucleic acid molecule of claim 1.

12. Transformed seed of the plant of claim 11.

13. A plant having stably incorporated within its genome a nucleotide sequence encoding a fumonisin degradative enzyme, wherein said nucleotide sequence is selected from the group consisting of:

a) a nucleotide sequence that encodes a polypeptide having the amino acid sequence set forth in SEQ ID NO: 7; and b) the nucleotide sequence set forth in SEQ ID NO:6.

14. A plant capable of degrading fumonisin, said plant having stably incorporated within its genome at least one nucleotide sequence encoding a fumonisin degradative enzyme from Bacterium 2412.1 operably linked to a plant promoter, wherein said nucleotide sequence is selected from the group consisting of:

a) a nucleotide sequence that encodes a polypeptide having the amino acid sequence set forth in SEQ ID NO: 7; and b) the nucleotide sequence set forth in SEQ ID NO:6.

15. The plant of claim 14, wherein said plant is selected from the group consisting of maize, sorghum, wheat, tomato, soybean, alfalfa, sunflower, Brassica, cotton, and rice.

16. A method of making an enzyme useful in degrading fumonisin, said method comprising:

a) expressing a nucleic acid molecule of claim 1 in a recombinantly engineered cell; and b) purifying said enzyme.

17. A method of making an enzyme useful in degrading fumonisin, said method comprising:

a) expressing a nucleic acid molecule of claim 1 in a plant; and b) purfying said enzyme from the plant seed or other plant parts.

18. A genetically engineered ruminal microorganism comprising at least one nucleic acid molecule of claim 1.

19. A probiotic composition comprising the genetically engineered ruminal microorganism of claim 18.

20. A feed inoculant composition comprising the genetically engineered ruminal microorganism of claim 18.

* * * * *

UNITED STATES PATENT AND TRADEMARK OFFICE

CERTIFICATE OF CORRECTION

PATENT NO. : 6,538,177 B1
DATED : March 25, 2003
INVENTOR(S) : Duvick et al.

It is certified that error appears in the above-identified patent and that said Letters Patent is hereby corrected as shown below:

Title page,
Item [56], OTHER PUBLICATIONS, "Rakin et al.," "132" should read -- 13(2) --; "Schmidt et al.," "91(9)" should read -- 91(1) --; "Armengaud" "PFRAM" should read -- PFAM --; "Coulton et al." reference "SWISSPORT" should read -- SWISSPROT --.

Column 15,
Table 1, under sub-heading "Gene", line 16, "fccE" should read -- fccP --.

Signed and Sealed this

Twelfth Day of August, 2003

JAMES E. ROGAN
*Director of the United States Patent and Trademark Office*

SEQUENCE LISTING

```
<160> NUMBER OF SEQ ID NOS:  59

<210> SEQ ID NO 1
<211> LENGTH: 24494
<212> TYPE: DNA
<213> ORGANISM: Bacterium 2412.1
<220> FEATURE:
<223> OTHER INFORMATION: Fumonisin Catabolic Gene Cluster
<221> NAME/KEY: unsure
<222> LOCATION: (1)..(24494)
<223> OTHER INFORMATION: n = a, g, c or t

<400> SEQUENCE: 1

ggccgcaatt aaccctcact aaagggatct tattggccat acggcgatag ttagcggcga     60

gcgcgcccag gtcgacgcgc aggtggccgc ccgccatgtc cgaagtcgtg tcgttcacca    120

tcgtccagcc cccgcttttc gcgctcgctg aagcctaggt gtgacttgtt cgaatatcag    180

gcctatctat cgcttagtct gcggatttat ccgcactact aaaatataat gctgaggtta    240

cgccacatga tgccagcgct ggacgcgatc gaccgcaaga tcattggcct gcttcgggtc    300

aatggccgca tgcccaacaa tgagttggcg cagaaggtag ggctttcgcc ttccgcctgt    360

ctgcgacgcg tcaagttgct cgagtcgaac ggggtgatcc gagggtattg tgcattggtt    420

gccgagcagt cgttggacgc cagcgtggtg gcgatcgtcc ggataacctt ggacaagcag    480
```

-continued

```
accgaggact atctgaatcg gttcgaggag gccgttcggc ggcatcccga gatcgctgag    540
tgctttctga tgaccggcga cgcagactac atccttcggg ctaccgcgcc gagcacggcc    600
gcctacgagc aaatccacaa ggaagtcctt tctcggcttc ccggggtggc gcgcatccat    660
tcgagcttcg ccatccgcag cgtgctgtcg tcggtcgcaa ggccctagag ctagccgcgt    720
tcggccacgg cggctcgacg agctcgagac ctaatgcacg attaatatcg aatatcccac    780
tctgccgctc gaccgacgcg gcggcgtcgc agctcgcgcg cagcgcaggc ccggctgggt    840
gcacattatt caagcacggg tgcgtcacct gaatggcgtc gcggcacgat tcaagaggtg    900
aactcgataa atattgaata aggcgccggt ctgccggagc atgggagtgc aaagacactg    960
gcagcagggg atctgaccat gcctagggat acgacaccga atttcgctcc ggtcaccacg   1020
gcaaaagagg gccgccgaca ccgaggcagc accgccttac gaaggctcat gctgacggcg   1080
gccggcagcg ccctggtgct gggtcttgcg cccaaggcgc tcgcgcaggt ggcggttccg   1140
ccggctggtc acgaggcgtc gcaggaggtg caggagatcg tcgtcaccgc gcagcgccgc   1200
agcgagaaca ttcagaatgt gccggtctcg gtgcaggcgc tgtcggcagc gcagctcgag   1260
cgcgaaggga tcaaacagac cagcgatatc gcccgagtga cgcccaacgt caccatcgcc   1320
atgcccaacg gcgaaggcaa ccagccggcg gtgacgatcc gcggcatcgg cctcaacgac   1380
ttcaattcca acaacgccgg cccgaacgcg atctatgtcg acgatgtcta tatcagcgcc   1440
ccgtcggccc agaccttcgg aatcttcgac atcaaccaga tccaggttct caaaggaccg   1500
caaggtacgc tctatgggcg caactccagc ggtggggcct tggtgttcac gtccagagcg   1560
ccgagccaag acttcgccgc ggacgcccat ttcgattacg gcagctacaa cacctatcaa   1620
ctgcaagccg gcgtcggcgg ccctctgagc gatcagctaa gcgcccgcct ggccttcgtc   1680
gtcaaccact ccgacgggtt catgcacaac acgctgacgg gcggttcggc gtcgggcacg   1740
gacaatcagg ccgtcaggct gcaactgctc taccgaccta atgacaggct gaaagtactt   1800
ctcagttcgg cctatggtca tgtcaactcg ccgatcgtcc agtaccgaca cttgggcgcc   1860
ttcgcggcag gaacccaatc cagcgccagc ccgactctct gcagccccga gcaggtccgc   1920
gccggaggtt gcgtcaacgt gttcggcgca ggcacgccga gcggcttcta cgacggttcc   1980
agcgatcgcg gtgaacgctt gcgcgtggaa aacttcctgc agcaggcccg cgccgactat   2040
gaggtcggtc cggtgaccct gacatcgatc agcgccttca cgcacagcaa aaagagcggc   2100
cccgacgacg ccgacgggac gtctgacagt ctgctccacg cgacctacgg cgttcgctcc   2160
gacacctgga cccaagagtt ccgcgccgcc tattccggcc agcgcctgca ttgggtggcg   2220
ggcgcctact atctcgacga gaccctcaag caaaatcagc cacttagcat cttctacgat   2280
ggagatcgct tcggcggcct gggcatcccg gccagggcgg gagccttcga cggcatcgcg   2340
caaaagagct taagccaaaa cactcagaaa acacggtcga tagccgcctt cggccaagcc   2400
gactatacct tggaccggtt caccctgacc ttgggcggtc gttacaccca tgaacgcaag   2460
acgttcgatc acttcagcgc gacccaggtc caagcaggag gccttgggaa atacggtcct   2520
ctcggcaaga tcgtctcgct gagcgaagcg ttcaaggctt ccgatccgac ctggcgcgcc   2580
gcgctttcct accgtcccgc cgagcgtgtt atggtctacg gcagcgtcgc caccggcttt   2640
aagggcggcg ccttcaacgg cgggttcctg agcagcaacc ccaacaaagc cctcgccgcg   2700
gtcaaacccg tcgcaccgga gaaggtgacc acctacgaac tgggcttcaa gtcgagcctg   2760
ttcgagcgtc gcctggtggt caacggcgcg gctttctaca acagctacga caacgagcag   2820
```

-continued

```
atcctggcca acacggccgt cgtcgtggat accgtgaccg gccctgttac cgtgacgacg   2880

aacgtcctga ccaacgcccg aaaggcccac tcccagggcg tggaattgga agtaaaggcc   2940

gtcccgatcc cggatctcgt cctcagcctg cagccggcct ggctgcgaac gcggctggac   3000

gaggcgggct tctccggggg aacgtcgctg gaaggcaagc aactggccaa tgcgccgaag   3060

ttctcgctct acgccgcggc ggactacacc ttccatcttg ccgacgacga cagcgtcaac   3120

gtcgccttca cctcggccta caagtcgcac cagttcttcg attcgacgaa cgccccctat   3180

acccagcagg agggctactg ggtgcacaac gccagcctga ccttcaactc cagaaaccac   3240

tgggatgtcg ggttcaatgt ccgaaacctg acgggcacga agtactacaa ctatctgttc   3300

gacgaggggg cgacgttcgg cttcatcaac ggcgtcgtgg ccgcgccgcg gacctacagc   3360

gtgcaattca acctgcatct ctaggcgcgc agaaggaggc gccgccatgc gcggcgcctc   3420

ccgctatcgg actgaaacgt taggtcctct tccccgcttc ggcgcgcggc gtcgccgcgc   3480

gccgtctctc tttgcaaccg tccgcggcga cccttgctgt cgcctagcag cgcggcgcgc   3540

tccatccatg cgccatgcgc aatgaatgcg acgatcgttg catttgatgg aggtttcgga   3600

ggccgctagt tctgctgcga gggggctccc gaccatgggc gccgtagccg cggctggcgc   3660

ggttcgcccc ctcgactgtc ccgacgtcgt cggcgcggac cgtagcgatc cgatcggaag   3720

gaatgggtgc gaagttgaag tatgacgtgg tggtggtcgg gggcggcaat gcggcgatga   3780

cggcggccgt caccgcgcgg gaagccggcg cgacggtgct ggtgcttgag catgcgcccc   3840

ggtcgatgcg cggcggcaac agccgccata cgcgcaacat gcgcacgatg cacgaggcgc   3900

cacttgcggt cttgaccggg caatattccg aagacgaata ctggaacgac ctgaagcggg   3960

tcacgggcgg ggaaaccgac gaggccctgg cccgtctggt gatccgcagc acgacggacg   4020

ccatcccctt catgctccgg tgcggcgtgc gcttccagcc atcgctgtcg ggcaccttga   4080

gcctgtcgcg gaccaacgcg ttcttcctgg ggggcggcaa ggctctggtg aacgcctact   4140

acgcgaccgc cgagcgcctg ggcgtcgaca tcctctatga cagcgaagtc accgagatcg   4200

tgctcgaagg cggccgggtc cggcgtctgg tggtccgcag ccaggggttc cccatcgagg   4260

tggaggcgcg cgcggtgatc gcctcgtcgg gcggcttcca ggccaacctg caatggctgg   4320

cgaacgcctg ggcccggcg gcgtcgaatt tcatcgtacg cgggacgccc tacgcgacgg   4380

gcacggtgct gcgcaacctg ctcgaccagg gcgtggcctc ggtgggcgat ccgacccagt   4440

gccatgctgt cgccatcgac gggcgcgcgc ccaagtacga cgggggggatc gtcacccgac   4500

tggactgcgt gccgttctcg atcgtggtca atcgcgacgg ccaacgcttc tacgacgagg   4560

gcgaggacat ctggcccaag cgatatgcga tctgggggcg tctgaccgcg caacagcccg   4620

atcagatcgc ctacagcatc atcgacagcc gatccgaacg acttttcatg ccgtcggtgt   4680

ttcccccgat caaagccgac tcgatttccg aactcgcggc caagctcggg ctggagccgg   4740

cgacgctcgc gcagaccatc gagacgttca atcgcgcctg ccaacccggt cgcttcgatc   4800

cgcaggatct tgacggggtc cgcaccgagg ggatcacgcc gtgcaagtcc aattgggccc   4860

ggccgatcac cgagccgccg ttcagcgcat atcccctgcg gcccggcatc accttcacct   4920

acctcggcgt caaggtcgat gaacgcgcca gggtgatcct ggcctccggc cagccgacag   4980

agaacctgtt cgcgtctggc gagatcatgg ccgggagcat tcttgggcgc ggttacctgg   5040

cgggcttcgg catggcgatc gggaccgtct tcggacgcat tgcgggccgg gaggccgcat   5100

atcatgcagc ataatgtcct ggatttcgtg accaagacgc gcacgggcga gccgcgcccg   5160

gccgaaacgc ccgcgatcat cgaagcgcgc cggaccatgg aggtttgcaa cgcctgtcgc   5220
```

-continued

```
tattgcgaag gctactgcgc ggtctttccg gccatgaccc tcaagcggga gttcgaggaa   5280
gccgatctca cctacctggc caatctctgt cactcgtgcc gcggctgtta ctacgcttgc   5340
caatacgcgc cgccccatga gttcgggatc aacgtgccca aggtgctggc cgaggtccgc   5400
accgaaagct accaggccca tgcctggccg caggccgtcg ccgtcgcctt cgagcgtaac   5460
ggtctggtgg tgtccctgag cgctgcactc gcgatcgttg tcgtgctgct gggaacggcc   5520
ttcttcaatg gatcggcgat gttccaggcg cacgcctcga cgcccggcgc aggcttctac   5580
aaggccgtgc cctatgcggt catggtgagc gtcgccggcg cgatcttcgc ctatgccgcc   5640
ttggcgatgt tcatcggcct tatccggttt tggaagaccg tgggccttgg cttgcgcgac   5700
gccgtcgaac cgcgaacctt gttccaggcg ctgaaggatg cggcgaccct gcgctatctc   5760
ggcggggggcg gcgatggctg caacgacgtc gacgctagct tctcgacctc acgccgacgt   5820
ttccatcacg ccatggccta cggcttcctg ctctgttttg cctccacctc caccggtacg   5880
gtctacgacc acctcctggg ctggcccgcg ccctatccct tcttcagcct gccggtgctg   5940
ctgggaacgg tcggcggaat tggatcgtc atcggcacgc tcggactgct ctggctgaag   6000
ctggtcggcg accaggagcc taggtcgaag gcgcaattgg gcgccgacac cgcgctgctg   6060
gtgctgctgt tcctgatcag cgtgacgggg ctgttgctgc tggcgcttcg gacgacggcg   6120
gccatgggcg tgatcctgac cgtgcacctt ggactggtct tctcgttctt cgcgacgatg   6180
ccgtacagca agttcgtgca cggactctat cgaaccgtcg ccttggttcg ttacgccgtc   6240
gagcgcaagg cgctggcctc cgggacgacg gaggaagcgt cttgatcttg gccnacgctt   6300
tggacgccgc aggccgcgcc cgccgctcag ccgaggggcg cctgggcctt gatcgcgcat   6360
cgaggggcct tggcccttgt tccgaccaat gtgtcggcgc ccgcaccgcc gtggccgaag   6420
acaggagaca atgaatgaaa gcggccattt accggcgcgg ggagatcgtt gtcgataccg   6480
ttcccgatcc ggttccagga ccaggccagg ttctcgtccg gagccttgtt tgcggggtat   6540
gtggttcgga tctgcattac cgacatcacg cacaccggtt cgtcgatctg gccttgcgct   6600
cgggcgcgcc cgccctggcc gccgatttgg atcgcgatat cgtccttggt cacgaattca   6660
gcgctcaagt cgtcgactac gggcctaaga ccgagcgtct cctgaagtcg ggaacggtcg   6720
tctgctcgcc ccccgtcgcg ttcggggcca gcggcatgcg cgccgttggc tactccgacg   6780
aattaccggg cgggtttggc cagtacatgg tcttgaatga ggcgttcctg atgccggccc   6840
caaacggact ggatccggct cgcgcggcgc tcaccgagcc gatggcggtg gggtggcacg   6900
cggtgaagct ggccggtccc ggacgcgacc atatcccgct cgtgatcggc tgcgggcccg   6960
tgggcatggc ggtcatcgcc gcgctccggg gtctgggcgt cggaccgatc atcgcggccg   7020
acttcaatcc ggcgcgtcgg agcctggcgg cgcgcatggg cgccgatatt gtcatcgacc   7080
cggcggagcg gtccccctac gacgaatggc gggataccgc ggcggcgtca ggcctggccg   7140
gactggcggg ggcgccagcg tcgctgcgga cctgtctggt cttcgagtgt gtcggcctgc   7200
caggaatgct gcgtcagatc atggaaggcg ccccggcgga gtcggagatc atcgtcgtcg   7260
gggcctgcat ggagcccgat agcctcgagc cgatgatggc gatgcataag gctctgacgc   7320
tgaattttcg cgaacctaca cgatcgagga gttcgccgag gtccttcgga tgatcggtga   7380
gggcgagctc cacgtcgagc cgttgctcag ccaacccatc ggcctggaag accttccggg   7440
ggtcttcgac naagcgcccg ggagggccgg gggcgccaag gtcctcgtcg acccctggcg   7500
ctgacgccgc cgaaaaccaa cgacagaaaa caacgggcgg gaggaacaat tgggtagcga   7560
```

-continued

```
tgagcaagac gatcctctcg tcggcggcgg tcgtcagttg cttctcaagc aatgtctgct   7620
caacgtcgtt gaccaggcgg ggagcaacga gatcgtctat caaggccggc tgaggttcag   7680
ctacgccgac ctgctttctc ggatttcgcg actggccgat gctttgacgg gcttgggcgt   7740
caagccgggc gacaccgtgg cggttctgga gtgggacagt caccggtacc tggaatgctt   7800
cttcgccatt cccatgcttg gcgccgtcat ccagacggtg aacatccgac tagcccgaga   7860
cgacctgcgc tacacgctcg agcatgcggg cgccaccctg gcgctgagcc acaccgattt   7920
cctgccgatc ctcgaggagg tgatcgacca attgcccagc ctgcgcgggg tcgtccatct   7980
gaaggacgac gaggcggaag ccgcccatcc ctgggtgctg ggggagtatg aggccctgat   8040
ggcggccgcg cgccctcggt tcgacttccc ggacttcgac gagaacacgc gggcgacgac   8100
cttctacacc agcggcacga ccgggcgtcc gaagggcgtc tactattcgc atcgtcagct   8160
ggtgctgcac accctggcgg tgatggcgac gctggccctt ggagacggtt acgccaggct   8220
ggggcgcgat acggtctaca tgccgatcac cccgatgttc catgctcatg cgtggggaat   8280
gcccttcgtg gcgacgatgg tcggctgcaa gcaagtctac ccagggcgct atgttcccga   8340
gcaactggtg gagcttcagc gcgcggagaa ggtgaccttc tctcattgcg tgcccacact   8400
tttgcagatg atgctcaatt cgccttcggg ccagacggcg gatttcaccg gatggcaggt   8460
gctcgtcggc ggagcggcgc tgccccgcgg cctggctctt caggccgcgg ggcgcggcat   8520
cgtcctgacc accggatacg gaatgtccga aaccgggccg ctggtcagct tcacgcgcat   8580
taggaccgaa gcaatggctc cagctcagga ggaggtcgcc attcgcacca aggtcggaca   8640
agctatcgcg ctggtcgacc tccgggtcgt ggatgagtcc atggcggatg tgccccgcga   8700
cggcctctcc gcgggcgaga tcgtgttgcg tgcgccttgg ctgacggctg ggtaccatcg   8760
cgatctggcc gcctcgcgcg agctttggcg cggaggaagc cttcatacgc aggatttcgg   8820
ccggattgac gcggagggct acctgcagat cagcgaccgc ctccagggag tcatcaagac   8880
ggtggggatg ggttctcctg agctgggaga tctcgtcagc cgccatccgg cggtgctgga   8940
gagcgccgcg atcgctgtcg ccgacgagcg ttggggagag cgcccagcga tggtcgtcgt   9000
gctcaggccg ggcatgagcg cgaccacggc ggacatccga gaccaccttt catcgtatgt   9060
cgcgaccggc gaaatacctc gctacgccgt gcccgagcag atctggttcg tcgaggagct   9120
cgaccgaacg agcgtgggca aggtcgacaa gcgggcgctt cgttccaggt tcgccgaagc   9180
ggcgtcctga gatggcgcat gaccgaacgg gaccaaatgg cgtcggcgtt ggttggctct   9240
ttccaaccct gttacggtcg ggtctgatga tggcgacgcg gtggtcgaac cgcgggaatg   9300
ggatcgtgta gccgggatgt tgaactgcga tctattggat ctgcgcgcct tcgtcgcggt   9360
ccacgaaacc cgcagcttca tccgcgcggc gcatctgctc ggcctttccc agcccgcgct   9420
cagtcgccgg atccaacgct tggagggact ggtcggcggc gctctcttcg accgaaccag   9480
ccggaccatg accgagaccg cgcttggcaa ggagctgctg ccggtggccc gccgaacgct   9540
tgagtttctg gacaattcgc tgttcgcctc gcccaagctg cgcgaaccgc gctggaccga   9600
catcagcatt ttttgcgtgc agaccgccgc gttccgcgtt ctgccgcgcg cggcccggcg   9660
cttcatggat gaaaatcccc gactgcgcct gaggatcatc gatgttccgg ctgtcgaagg   9720
cgcggaactg gtggcgcgag gggaagcgga gttcggtatc agcatcgaga gcctgcttcc   9780
gtccggcctg cgtttcgagg ctcttcacga ggacccgttt ggcttggcgt gccatcggag   9840
ccatcgcctg gcgcaaagcg acgtcatcga atggtccgcg ctccgcggcg aaaatcttgt   9900
cgccgtccac cgggccagtc gcaaccggac cctgctcgac gccgagctca agcagcatgc   9960
```

-continued

```
gatctccctg gactggcgtt acgaggtcgg tcacttgacg accgcgctgg ggctgatcga  10020
gtccgaggtc ggcgtggccg tcatgccgcg gatggtgatg ccccaatcag gccgctcaga  10080
actggtctgg gttcccttgg tcgccccggt cgtgaggcgc acgatcggca tcgtgcagcg  10140
ccgggtgggc gcgatgcatc ccgccgccgc ccaactgctc gagcggttgc gggaggaatg  10200
gccgaccggc gcgcccgcgg acgagtagac cgccaagatt cgaggtccgt gcgggcgcgc  10260
ggcggctggc cggtcgtcac cgcggccccg tcaccgcgtc atattcagca cctgcacttg  10320
ggtgaactcg tgcagccctt cctcgcctaa ctccgagccc atccccgaga acttggcgcc  10380
gccgagcggg agatcgggct gcacgtcggc gtgcttgttc acccagaccg agccggcctc  10440
catatcggcg gccaggctcc acgcgcggac gacgttgcgg gaccagatgg atccccccag  10500
accatagggc gaggcgttgg cgcggcgcac ggcgtcgacg gggtcggagt accggatcac  10560
cggcatcacc gggccaaact gctcttcgtc gacgagctga gcgccttcgg cgatgtcgcg  10620
tacgatggtg ggctcgatga aatagccctt gtcgcccttg cggcggccgc cggcgatgat  10680
gcggccgtcc gtcctcgcac gctcgattag accaagaacc ttctcgaact ggcgccggtt  10740
ctgcagcggc cccatctgaa cgccctgttc gagtccatcg cccacgaccg tgcgggccgc  10800
caactgcgcg aactcctcgc acatggcctc atagaggctc tcatggacgt aaatccgttt  10860
ggcggcgatg cacacctgac cggcgttttg catggccgcg gcgaacaccc tgggagcgac  10920
ttccttgggg tcgacgtcat ccaggacgat cagagcgtcg tttccgccca actcaagcga  10980
tatacgtttg aggccttcgg ccgcgccggc catgaccttt tttccggtct gggtcgatcc  11040
ggtgaagctg attttgcgaa tgccaggatg gcgggtcatt tccgcgccga gatcgtcggc  11100
gtcggtgatg atgttaatga cgcccggtgg gacgatatcc ttgaccaagg cgccaaaccg  11160
aagcgccgtc agaggcgtcg tcgccgccgg cttgaggatg accgtgttgc cggccagcag  11220
ggccgccggg atcttgaacg ccatcaacag catcgggaaa ttccagggga cgatgcagcc  11280
caccacgcct agggggcgtc tatgcacctc tacgcggccc gtcgcgtcgt ctctgaccac  11340
gcgaggcggc agatcgagcg aggtgaagta gcggaagaag gccgcggagg cgtagatctc  11400
gcccatcgcg tctgcgagcg gcttgccctg ttcctgcgtc agcaaacgcg ccagcgccga  11460
ctggtcggct tcaattgcgt cggcgatggc gttgagcgtg gccctgcgct gctcgagcgt  11520
ggttgcccgc cagctctgaa aggcgcgttc cgcggcggcg acggcttcgt ccagttggtc  11580
gcggtcggcc ctggggcaat cgatcaccag cggcgtttca gtcgcgggat tgattacgga  11640
catcgtcgtt gcgccggcga ccaggcggcc gtcgatcagc agcttgtact ctagcatgtt  11700
ggctccgatg gtcggctgat cgagccgccg gtttgcatgc ggcgctcgat cacgggattg  11760
gagatcgact tcaaccggtc aggccctgat agccctcgtg gaagcgcatg gcgatcgacg  11820
ggggaaaggc caggttcgca gccctatctg tccggacccg cacaagggcc ggtccgagcg  11880
catcgcgcgc cgcgctcaga gcgggccgca gatccggcgc ggtctcggcc ttgaagccga  11940
agcatcccag gctttcggcc aacctttccc agaggacggg gcccatctcg gtgccgaagg  12000
tcctgccgta gcgcgcctgc tcattcggga cctccatcga ccacgaccct tcggccagga  12060
cgacgacggt caccttgacg tcctcgcgga cggcggactg cagttccata caatggaagc  12120
cggccgcgcc gtcgccagta acgcagacga tctggcgatc cgggcttccg agacccgcgc  12180
cgatcgcaga cggtatgccg gtgcccagca tccccatctc aagaatgttc aggtacgagc  12240
gcggtctggt cgagggcaac ataaagtgag cccaaaggct cgtgaaaccg ccatcggcga  12300
```

-continued

```
cgtacaccgc atcgggaccg aaaacctctc ccaccgtctg cataacctca gccgggtgag  12360
gacttggacc gccatgggcc tcgatatgag cgaactcgga acgccgccat tcggcgtcca  12420
tttggcgata gcgcgtgagg tcgacgtccg cgcccgagcg cgtgggcgcg ttctcgaggg  12480
cctcgaggag gccttccacg aggctgcccg cgtccgaaac gatgcctagc gtcaacggac  12540
gtgaggcgcc caaattgcgg gggtcgatat cgacctggat cagcttgtgc ccctccgatg  12600
agccccaata gcggtcgaag ggcgtgtcga tgtttcccag gcgcgtgccc agcgccagga  12660
tgacgtcggc ttcgcgtcgc gcctgatcag cgccggcgcc ataggcgtgc aggtggaggg  12720
ggtgatcttg agggacggcc gaccggcccg ccaggctggc gatgacgccg caacccagct  12780
tgtcggctag gcgcagcaca gcctcgcccg cgccagctcg gtcgaccccg gagccgacca  12840
tgatcagcgg acgagtcgcg gcggccagca attgggcggc ggcgttgatt tgcgagccgc  12900
cggctgaagg agggggcgcc cgataggcga tcggatcgag caggccagcc cgggactcgt  12960
cggtcatgtc gtacatcact gggctcggaa catcgatctg gaccgggccg ggacgccccg  13020
cccacatctc ccggaacgcc atgcgcgtaa cctcgccgat gcgttgccag gtatgaatgg  13080
gcgcgcccca tttgaccgcc gggcgcagga gttccaattg gtcggcgccc tggaacgtgc  13140
tgggcgtcgc gggatagacg accccgccat gatgctgcgc ggtgatggcg atcatcggca  13200
cgccctcatg cttggcggtc accaagccgg gcagcaggtt tgccgtaccg ggtcctgggt  13260
ttgtcacggt ggcggcgact tggcctgtcg tcttgtagag accctcggcc atataggccg  13320
cagccgcctc atgccgcacg gggatgaagc ggatgccgtt gtcgtcgagc gccgccagca  13380
gcggatcaac ctccggcgac atcaagccga aaacaaaccg cacgccttcg cgcgctaggc  13440
actgcgcaag taatgcgccc ccggtgatcg ccatttgttt ctccctgcgt acgacggcgc  13500
atggaacacc gccgcgtctg gtcgttgtcc gaccacgttg ccgacttttc gaactatcag  13560
tcgataatta tcgaaacagc aaccggtctc gtttgcaata cgagccgtag gccgccattc  13620
tgatcgatga gaaacgaagt ggcgcgatgc ggttcaaacg cttgttttat ggggcgtttc  13680
gccatcgcga catgcgttcg gcgcattgat cgccccgatc attgcattgg ctggcggact  13740
ggcgcgccga tagtcgttgc gatggtcgcg agaataagcg tgcgaagtgg gaggatgtga  13800
agatgggggc caggagtatg tgtgcgggac ggttcggacg cttctgcatt ggcttggctt  13860
catcggttgc cgtgactcta gggggagcct ccgccgccgg cgcggcaacc gcgacggatt  13920
ttccggtccg caggaccgat ctgggccagg ttcagggact ggccggggac gtgatgagct  13980
ttcgcggaat accctatgca gcgccgccgg tgggcgggct gcgttggaag ccgccccaac  14040
acgcccggcc ctgggcgggc gttcgccccg ccacccaatt tggctccgac tgcttcggcg  14100
cggcctatct tcgcaaaggc agcctcgccc ccggcgtgag cgaggactgt ctttacctca  14160
acgtatgggc gccgtcaggc gctaaacccg gccagtaccc cgtcatggtc tgggtctacg  14220
gcggcggctt cgccggcggc acggccgcca tgccctacta cgacggcgag gcgcttgcgc  14280
gacagggcgt cgtcgtggtg acgtttaact atcggacgaa catcctgggc tttttcgccc  14340
atcctggtct ctcgcgcgag agccccaccg gaacttcggg caactacggc ctactcgaca  14400
ttctcgccgc tcttcggtgg gtgcagagca acgcccgcgc cttcggaggg gaccccggcc  14460
gagtgacggt ctttggtgaa tcggccggag cgagcgcgat cggacttctg ctcacctcgc  14520
cgctgagcaa gggtctcttc cgtggcgcta tcctcgaaag tccagggctg acgcgaccgc  14580
tcgcgacgct cgccgacagc gccgcctcgg gcgagcgcct cgacgccgat ctttcgcgac  14640
tgcgctcgac cgacccagcc accctgatgg cgcgcgccga cgcggcccgc ccggcatcgc  14700
```

-continued

```
gggacctgcg caggccgcgt ccgaccggac cgatcgtcga tggccatgtg ctgccgcaga  14760
ccgacagcgc ggcgatcgcg gcggggcagc tggcgccggt tcgggtcctg atcggaacca  14820
atgccgacga aggccgcgcc ttcctcgggc gcgcgccgat ggagacgcca gcggactacc  14880
aagcctatct ggaggcgcag tttggcgacc aagccgccgc cgtggcggcg tgctatcccc  14940
tcgacggccg ggccacgccc aaggaaatgg tcgcgcgcat cttcggcgac aatcagttca  15000
atcggggggt ctcggccttc tcggaagcgc ttgtgcgcca gggcgcgccc gtgtggcgtt  15060
atcagttcaa cggtaatacc gagggtggaa gagcgccggc tacccacgga gccgaaattc  15120
cctacgtttt cggggtgttc aagctcgacg agttgggtct gttcgattgg ccgcccgagg  15180
ggcccacgcc cgccgaccgt gcgctgggcc aactgatgtc ctccgcctgg gtccggttcg  15240
ccaagaatgg cgaccccgcc ggggacgccc ttacctggcc tgcctattct acgggcaagt  15300
cgaccatgac attcggtccc gagggccgcg cggcggtggt gtcgcccgga ccttccatcc  15360
ccccttgcgc ggatggcgcc aaggcggggt gacgccgtcg acgatggcgt gacgacggtc  15420
gaggcgatgt tctcgatctg gagtccgcgc cgcctcgatt tgcgtcgtct ccggcgctca  15480
gacgaacgcc ccagttccat ccacacagtc actttcccga gccgagctgt cggcggtggg  15540
acgaaagaga agccgatgcg agccataccg attcaaagcc gacccgttcc atccgatcgc  15600
caagccccgg ctcgcggggt gacgcaatga cggccgcgga ggagcgccgc gggcatttgg  15660
gtaagatcct gcgcgtggcg agcggcaact tcctcgagca gtacgacttc ttcatctacg  15720
gctactacgc gacctacatc gcccaggtgt tctttccatc gggcgacgag acgacgtcgt  15780
tgatgctctc cctggccacc tttggcgtcg ggttcctgat gcggccgcta ggggcgatca  15840
ttctcggatc ctacatagat cgcgtcggcc gccggcaggg cttgatcgtc acgttgggga  15900
tcatggcgat cggcacgctc accatcgccc tgacgccggg ttacagcgcc atcgggatcg  15960
ccgcgccgct catcgtcgtc gccggtaggc tcttgcaggg cttctccgcc ggagccgaac  16020
tcggcggcgt ctcgatctac ctggcggaaa tcgcaaagcc tggtcgacgg ggcttctaca  16080
cctcctggca gtcggccagc cagcaggtcg cggtgatggc ggccgcgctt gtcggtctaa  16140
gcctcggcgc aacattgacg cccgaccaaa tgcaccagtg ggctggcgc gttccgttgc  16200
tgctcggctg tgcgatcgtc cccgtcatcc tgtggctccg ccgatcgctc gacgagaccg  16260
aggcctataa acacattcat cacaaggccc attccctatt gggctcgctg gcccagttgg  16320
ggggcagctg gaggccgatc ttggccggca tggcgatctc ggtcctgacc accacgacct  16380
tctatatgat caccgcctac acgccgacct tcggaaagca ggctctcggt ttggacgccc  16440
aggacgtcct cgtcgtcacc atgctggtcg gcgcctcgaa ctttatatgg ctgccggtcg  16500
gcggcgcgct ctccgactgg attgggcgca cgccggtgct cctctctgtg cccctggtgg  16560
tccttgtcgc ggcctacccg ctgatcgcct ggctggtggg cgcgccatcg ttcttcgcgt  16620
tcgcgacggc gctgctggcc ttgtcggtct gctttggcct ctataacggc gcgatgatcg  16680
cacgactgac cgaactgatg ccgcctgcgg cacggacgct ggggttttcc ctggcgttca  16740
gtctggccac gtcgctgttc ggaggcttca cgccgctggt cagcacttat ctgatcagcg  16800
cgaccggtaa caaggccgca cccgcgctgt ggctgtgctt cgccgcgatg atcagcctga  16860
tcggggtatt ggcttcacgc aggatggggg ccgaccccga tcgatccatg gcttgaaggc  16920
gctcgccgcc gacggcctcc cgtacccaga tcctatcggc ggagccagcc ggcctgcgga  16980
tccccgacac gggcgttccg caggccggtt ttcttgttcg tggggaggag gttggcctgc  17040
```

-continued

```
ggcgctcgat ctcgcgagcc atgggccgcc cccaatcttt cggctgggcc gtgcggcgtt  17100
gggcgcgccg gccatttcga cggcggcttg cgccgccatc gacacgtcgt tcaggccggg  17160
gctttggtgt tcgcatgtcg ggactttaaa gtagccgccc gccgccaggg gccggccacg  17220
acgtagagcg ccgccgccgc aacgaggagc cggccgaaac ctggaatgcg cctcccaccc  17280
gattatcgtc aatgacgaac gaggccgcca acggaccggc gctgaagccc accaacgcga  17340
gaggggcgag cagtacggcg gcggtcctgc tgggctccaa ggcgatcacg tccgccacca  17400
gaaacggctg cagcgccagc cagaacaggc caaagccaca agcgcttgcg atgagcgcga  17460
cgggcgtgcc ggcgtgaagc aggccgatga caagaccggc ctgcagcact gcgccggcgg  17520
ccagaaccgt acgggcgtgc acgcgcgcac cgagccagga tgctgcaaga gcacccgcca  17580
cctggaaggc caggctgccc gcgatcgcgg cgccgaccgt ggccggggcg aaatggtgtt  17640
gcgcggccag gcgctccagg tagttccatg ccgccccgat gccggcgttt tgaagaaacg  17700
ccgcgagcgc cacgaccatc agggccggag agacgactac gcgaccatgg tgcgatcccg  17760
taggagcagg cacgtggtcg acgatcgccg gcgcaacgag gcaggaggcc atcgcaacgc  17820
ccgccaagac cgcgaacccg gcatccacgc caaaccgcgg gatcacccag atcggcagca  17880
aataggccgc gatcacctgg gggatcgtgg aaagaccgag cagcagcccg ctcatgcgct  17940
caggccggtc gttgtgggta aggatggcgc cggccgcgcc cagcaatagc ccttccagca  18000
acccggccgc gccgcgttgg accaggatcg tggccgggga tgcggcccag tagatggcga  18060
ggttgatgat cgcaaggagc agggaggcag cggccacctt ggcgcgcatg tggccgaggt  18120
tcatcaggaa cggacccgcc gtcgagcctg cggccagggc gaagacttcg atcatggcgg  18180
cctgacctac gcccgcctcg ctgatccgcc cggcgttggc gagacccccg agcaggatgg  18240
gttcgacgcc catcaccagc atcgaggccg tgccgatcag catagtggcc gatacgacgg  18300
acacggcctg gtgatggcga ggtccggtat tccggggcag ggtcagggac ataggctcca  18360
actgtcgtcg agaaggtgaa gggaattcgc atctgtgggg gagcggctgc gctccacaca  18420
cccagcaaat atcgataata gtttgagagc aattctgaca tcgtccgcga tttacgaaaa  18480
cacgcatatt ttaattgcct gccgctggat taagcagata aatatcgagt taagcctccg  18540
gtgcgttttc gatcccgaag ttggtgatca tcggaccgcc gatagtcagg gcgcacgaaa  18600
ccagggaggt gagcatgccg gatggtgagg ctatcagcgg cgtcggccag tggttggcgg  18660
ctttcgagag cgcgctgaaa cgcgacgatc tggcggcggc ggtcgaccta tttgtcgagg  18720
acgtcttttg gcgagacatc gtcgccttca cctgggatat ccgcacgctc gaggggcgcg  18780
gggcgatcca agagcttcta ggagccgcct cggggctcgc aaggtccgcg tcctggtcga  18840
cgacgtcggc cgatcatgat caggaaggcg tcgtcagctt tgaaaccgac ctggggcgag  18900
gccatggtta ccttcgcctc cgggggggac gctgctcgac attgctgacc tgtctggaag  18960
aactcacggg acatgaggag acacgcggcc ctcgccgtcc gcgcggggcg agcgtaggcc  19020
cggcggaccc tgacgaaaat tggaagaatc gtctcgaggc ggaaagccgg gcgatggggc  19080
gtgagaccca gccgttcgtg cttatcgtcg gcggcggtca aggcggtcta gcgcttggcg  19140
cgcgcctccg tcagctccag gtcccgactc tgatcgtcga tcagcaccca cgggtggggg  19200
accaatggcg atcgcggtac gcatcgctct gcctgcacga tccagtctgg tacgaccacc  19260
ttccttacct gccgtttccc gatacttggc cggtttatac gcccaaggac aagatcggcg  19320
attggctcga agcttatgcg caggcgatgg agctgctggt ctggtgttcg accagatgcg  19380
tgtccgccgt ctatgacgcc gaagccgggc gatggaccgt caccctgcgc cgaggcgagg  19440
```

-continued agaccagcgt catccgcccc gcgcatctgg tcctggcgac gggcaacgcc ggcaagccgc 19500
gcgttccgcg cttcaagggc caagcgcagt tcgaaggtcc gatcctgcac tcgagcgcct 19560
atcggagcgg ggctgatttc aaaggacggc gcgtggccgt gatcggatcg aacaattcgg 19620
cccacgacat ctgcgcagac ctcgtggccc acggcgttga cgtcaccatg atccagcgca 19680
gttcgaccca tgtcgtccgt tccgaaacgg tcatgcggac catgctcgcg ccgctttatt 19740
cagaggaggc cttggcggcc ggcataggca cggagctggc cgacctgctt gtggcttcca 19800
tgccgttacg cctgcaggcc gaaggctatc gcgccctcca cgtcgcgatc gccgagcagg 19860
acgcagcgtt ctacgccgcg ctcgaggcga tcggcttcat gcatgacttc ggcgaggacg 19920
gcaccggcat gccgctgaag tatcttcgtc gcgcgtcggg gtactatatc gacgtcggcg 19980
catccgaact cctggccagc ggggccataa agctgcgctc ccgcgtcgag atcgatcact 20040
tcgacaccga cggcctggcc ctctcggacg gcagcaaggt cgacgccgac gccgtcatct 20100
gcgcaaccgg tttcggctcc atggacgagt gggcggccga attgatttcc cccgaggtcg 20160
cggccaaggt cggaagggtc tggggctatg ggtccggcac ccgaggcgat ccgggcccct 20220
gggagggcga acttcggaac atgtggaagc ccacccgcca gcagggcttg tggttccagg 20280
gcggaaacct ggcgcaaacc cgcttctact ccagagcgct cgctctgcag ttgaagcccg 20340
acatgctgat tgccgtgagt ctacgttcgt caccgactag gcggcggcga agctcactga 20400
tcttgctccg cggcgtccca gaggctcacg ctcgcctctc cctggtctat tgcttcgcga 20460
atttgcggcc gcagctcgag atgttcgggc aagaacgtcc tgcaataggc gacgctcacg 20520
gtcagggcct cttcgtagta gtcctcggtg atcgcaccgt tttggacaaa cgagatcgcc 20580
agaaccgcat cgacgatctg gatgttcgtg tgaaacttct tctgcggatc gcgcagaaaa 20640
ggcatgtgga agatgcggtc aaggcgctga taggccgcgc gagcgacggc ttccacatat 20700
tcgcgatcgg cctgccgtgt ctcgagcccg ccaaatccac ccaggaatag cttcgaagcc 20760
ggcgagttgg cgttgtagta atccacgcca ttgcgcaggt cccacgccgt cagcgcctgc 20820
caactactga gactcttcac cggaatgggc cggcgggtga gttgctcgaa acctttcagg 20880
tgcctttgcg ccagcgccag gaaggcggcc tccttggtcg ggaagaagtg atagaccgag 20940
gcgggtggaa cgccggcccg ctcggcgatc tgatagaggc cgacggcggc ggggttctcg 21000
tcctgtagca gcgcctcggt cgcatccagc agggccgtgt agcgagtcag cgacgtgctg 21060
cgggacggcg cgcgcgggcg aaccttcttc ccggatgcgt tccgcgggtg atggggcctg 21120
agtcgtctcc atgaacgaga gtagcggcgc ggcgagcctt ggatatcggc aatgatggcg 21180
ccgggttgct ctatgacgag ccgaatggcg gcgctcggcg caagtgtgcg atgtaaaaaa 21240
tgtgccgcgg acgtgacgtc cgcggcacac aaccgggcga tggctagagt tgctcgtatc 21300
ctacagccac ctcccggtgg acgccgccag ggaggaatgg gcgtccgggg aggggagtca 21360
gtagcggaag cggagcccga cgttgaaata cctgccgcgc ggatcgtagg ctgcgctcgt 21420
cgggaccgag aagctggacg gattgaccgt cgccaccggt ggatcacggt cgaagaggtt 21480
gtttaccgaa gcaaaaacct gctgcttatg cccgaatgaa tcgaagctgt aggtcaccgt 21540
ggcgtcagtg taccagactg cgccggtgtg gttcaggttg gtgtcgacac cttcgacgtt 21600
ttcagcgtca aagaccgagc gagagatgaa gcgctcttgc aggaacagcg accatgcggc 21660
gcgctcgtaa cgcgcctgca gattgagcag ccatttgggg gcggtgggtt cgccgagcga 21720
ttgtaggggc gccgagccca gggcggtgac ggatgcggcc gtgcggtggt tggccaaggc 21780

-continued

```
ccgcaggttc agagatccgc ccgcgacgtt gcgcacgtag gacgcctcca aatcgacacc  21840
cgccgccttc tgcaccgcaa ggttcaggtt ggggccgatg acggtcagcg tgttgtccgc  21900
attccgggtg atcaaggcgc acatggactg gttgcccgcg gcgcagaggt cgatctcctg  21960
ctggggcagg aggtagtcga tggcgtcttt gagatcgatg atatagcggt ccgccgaaag  22020
ctgaagcccc ggggcgaagg ccggccgcaa cacgacgccg aaggtcaggg tatcggcgcg  22080
ctcggggcga agatccgggt tgccggcggt gaagaagcgg gtctgcaacg tctggccctg  22140
atagacagag ttcagggtag cctgacggcc ggggtcgtag agttccacca ggctggcgcc  22200
gcggatgtcg cgcgagcgag tcaggcgaaa ccgcagtcca tcgacgggct cgtagtcgcc  22260
gccgaccttc caggtcgtga cgccgcccga gacgctatag tcggcatacc ggaccgcgcc  22320
gttgaggttg agcgctcgac caagcgcgct gtccttgagc accggaaccc cgacctcaag  22380
ataagcctcc ttgatgttgt agctcccgct gaagggaaga gggttgtaga ggttgaaacc  22440
accaggccgg ttgctctgag aggccggcgc tccacgcagt ccggcggtcg acgtgatcgc  22500
ctgcgagatg gcgtcggtgg tctggttggc tttctcctca cgatattcgc cgcccgcggc  22560
gatcgagatc ggcccggcgc ccagcgaaaa cgcctggcca aggtcgccga cgaggttcag  22620
gcccgcgacg acctgttcca gtttcaggtt cgccaccccg tcgtcgagga catagtcgat  22680
cgcggcggca cttggcgcgc cggcgccgaa aatgttgagc ggcacgcagc ccgcgtcgag  22740
acccgaaagg gtcgaacggc agacgatctt tcccgtcggg tccttcacgg cgtcgaccgc  22800
tgcatagaga ttgcggttga tcgacaggtt gttttcgcga agctccaggt tcgtgcggcc  22860
gtaggagatc gaaccgtcga gcttccaggt gtcgttgagg tccgcccgga agccggcagc  22920
tccgcgacgc accttggcgt aggactcgat ctcgaccagc gggaactcgc cggcgaaccg  22980
gccgacggaa accgacgtca gccggttggt gtccatcagt gcgccgagtg cggtcgggag  23040
gaacgcgttg tcgcggaaga tcgtgaaggc gttcgcgctg ccgacaaact ggttgacgaa  23100
ggcgccgagg ttggtgtggc tataggcata ggtgccttcc gcatagagct tgacgcgttc  23160
tgaggcctcg aactcgccgc ggaggaagcc attgtagcgc cgctggtccg gagcgaagcc  23220
gagattgacg cgcggaccgt cgccgccgct ctggaaggaa ctgctggtaa agcttccgta  23280
gttaaaggtc gcaagcgtac cgccgggaag aaaggtgacg cccttcagcg gacccgatgt  23340
gatcaggccg ccgtaggcgc cgcgcgagct tcggatgtcg ggaaccaccg tgacgcccgt  23400
cggggcgccg ggcacgggat attgccccgc cgcgcgatca taccacgccc gatcggtggc  23460
ctgatcggcg cgaatgccgt cctcgtgata gtattcgacc gcggcaagga gatgtgcgcg  23520
cccttgggca aacgacttgc cggccgccag cgatccgccc accgaggcca gatcgttgcg  23580
gctcgagacg ccggtctgga cgttcgcctt taggccctcg aaatcctcgt cgaggacgaa  23640
gttgattacg ccggatacgg catcggatcc gtaggcggcc gaagcgccgc cggtcaccac  23700
gtcgacccgc ttgacgagag cctggggcaa cacattgacg tccaccgatc cggtgtagtt  23760
ggtggcgacg aagcggttgc cgttgagcag aacgaggttt cggttcgcgc ccaggccgcg  23820
caggctcagg agattctggc cgctgttgcc ggtgcccggc gtcgtgccgg ggttcgacgt  23880
tttcagacta ttattgaaga ccggaagttg gttgaggcca tcggcgatgt tggttggagc  23940
cgccgccttg agctgatcgc agacgccgcg gtcacgggag tcggtgcgct gaatccgctc  24000
tggaggcggc tgcccgtgac gacgatttcg ctgacttcct ggcgtcctgg gccgagggtt  24060
ttcgacaggt gcttgctgcg cccggccgag gcttggggct agaagcacgg acgtcgccgc  24120
tgcgcccagc aggctaaggc ggaaagtgct cttctgattg gttgctgctt ggctcatggc  24180
```

-continued

```
taatccctcc ctctctttgt gacggcgagg gggggacggc atggcggaac gccgcacgcg  24240

aaaatgtccc ggttcctcct cgattgggcg atgtgcctcg cccttccgct atgagtaacg  24300

agggcttttg ggcccatcaa atgcaatgat cggcgggctc tattcgcccg gcgcatggat  24360

cttttcgatc tgccggattg gcaattcagg gttgaaaata cgataattat cgaattgagt  24420

tagtgggggc tctcgtttct cgagcagaat tgatcggtgg cgtagtgagg ctgaccatgc  24480

aggttgacgg gatc                                                    24494


<210> SEQ ID NO 2
<211> LENGTH: 1590
<212> TYPE: DNA
<213> ORGANISM: Bacterium 2412.1
<220> FEATURE:
<223> OTHER INFORMATION: fccA Fumonisin Esterase
<221> NAME/KEY: CDS
<222> LOCATION: (1)..(1587)

<400> SEQUENCE: 2

atg ggg gcc agg agt atg tgt gcg gga cgg ttc gga cgc ttc tgc att       48
Met Gly Ala Arg Ser Met Cys Ala Gly Arg Phe Gly Arg Phe Cys Ile
  1               5                  10                  15

ggc ttg gct tca tcg gtt gcc gtg act cta ggg gga gcc tcc gcc gcc       96
Gly Leu Ala Ser Ser Val Ala Val Thr Leu Gly Gly Ala Ser Ala Ala
             20                  25                  30

ggc gcg gca acc gcg acg gat ttt ccg gtc cgc agg acc gat ctg ggc      144
Gly Ala Ala Thr Ala Thr Asp Phe Pro Val Arg Arg Thr Asp Leu Gly
         35                  40                  45

cag gtt cag gga ctg gcc ggg gac gtg atg agc ttt cgc gga ata ccc      192
Gln Val Gln Gly Leu Ala Gly Asp Val Met Ser Phe Arg Gly Ile Pro
     50                  55                  60

tat gca gcg ccg ccg gtg ggc ggg ctg cgt tgg aag ccg ccc caa cac      240
Tyr Ala Ala Pro Pro Val Gly Gly Leu Arg Trp Lys Pro Pro Gln His
 65                  70                  75                  80

gcc cgg ccc tgg gcg ggc gtt cgc ccc gcc acc caa ttt ggc tcc gac      288
Ala Arg Pro Trp Ala Gly Val Arg Pro Ala Thr Gln Phe Gly Ser Asp
                 85                  90                  95

tgc ttc ggc gcg gcc tat ctt cgc aaa ggc agc ctc gcc ccc ggc gtg      336
Cys Phe Gly Ala Ala Tyr Leu Arg Lys Gly Ser Leu Ala Pro Gly Val
            100                 105                 110

agc gag gac tgt ctt tac ctc aac gta tgg gcg ccg tca ggc gct aaa      384
Ser Glu Asp Cys Leu Tyr Leu Asn Val Trp Ala Pro Ser Gly Ala Lys
        115                 120                 125

ccc ggc cag tac ccc gtc atg gtc tgg gtc tac ggc ggc ggc ttc gcc      432
Pro Gly Gln Tyr Pro Val Met Val Trp Val Tyr Gly Gly Gly Phe Ala
    130                 135                 140

ggc ggc acg gcc gcc atg ccc tac tac gac ggc gag gcg ctt gcg cga      480
Gly Gly Thr Ala Ala Met Pro Tyr Tyr Asp Gly Glu Ala Leu Ala Arg
145                 150                 155                 160

cag ggc gtc gtc gtg gtg acg ttt aac tat cgg acg aac atc ctg ggc      528
Gln Gly Val Val Val Val Thr Phe Asn Tyr Arg Thr Asn Ile Leu Gly
                165                 170                 175

ttt ttc gcc cat cct ggt ctc tcg cgc gag agc ccc acc gga act tcg      576
Phe Phe Ala His Pro Gly Leu Ser Arg Glu Ser Pro Thr Gly Thr Ser
            180                 185                 190

ggc aac tac ggc cta ctc gac att ctc gcc gct ctt cgg tgg gtg cag      624
Gly Asn Tyr Gly Leu Leu Asp Ile Leu Ala Ala Leu Arg Trp Val Gln
        195                 200                 205

agc aac gcc cgc gcc ttc gga ggg gac ccc ggc cga gtg acg gtc ttt      672
Ser Asn Ala Arg Ala Phe Gly Gly Asp Pro Gly Arg Val Thr Val Phe
```

-continued

```
    210                 215                 220

ggt gaa tcg gcc gga gcg agc gcg atc gga ctt ctg ctc acc tcg ccg      720
Gly Glu Ser Ala Gly Ala Ser Ala Ile Gly Leu Leu Leu Thr Ser Pro
225                 230                 235                 240

ctg agc aag ggt ctc ttc cgt ggc gct atc ctc gaa agt cca ggg ctg      768
Leu Ser Lys Gly Leu Phe Arg Gly Ala Ile Leu Glu Ser Pro Gly Leu
                245                 250                 255

acg cga ccg ctc gcg acg ctc gcc gac agc gcc gcc tcg ggc gag cgc      816
Thr Arg Pro Leu Ala Thr Leu Ala Asp Ser Ala Ala Ser Gly Glu Arg
            260                 265                 270

ctc gac gcc gat ctt tcg cga ctg cgc tcg acc gac cca gcc acc ctg      864
Leu Asp Ala Asp Leu Ser Arg Leu Arg Ser Thr Asp Pro Ala Thr Leu
        275                 280                 285

atg gcg cgc gcc gac gcg gcc cgc ccg gca tcg cgg gac ctg cgc agg      912
Met Ala Arg Ala Asp Ala Ala Arg Pro Ala Ser Arg Asp Leu Arg Arg
    290                 295                 300

ccg cgt ccg acc gga ccg atc gtc gat ggc cat gtg ctg ccg cag acc      960
Pro Arg Pro Thr Gly Pro Ile Val Asp Gly His Val Leu Pro Gln Thr
305                 310                 315                 320

gac agc gcg gcg atc gcg gcg ggg cag ctg gcg ccg gtt cgg gtc ctg     1008
Asp Ser Ala Ala Ile Ala Ala Gly Gln Leu Ala Pro Val Arg Val Leu
                325                 330                 335

atc gga acc aat gcc gac gaa ggc cgc gcc ttc ctc ggg cgc gcg ccg     1056
Ile Gly Thr Asn Ala Asp Glu Gly Arg Ala Phe Leu Gly Arg Ala Pro
            340                 345                 350

atg gag acg cca gcg gac tac caa gcc tat ctg gag gcg cag ttt ggc     1104
Met Glu Thr Pro Ala Asp Tyr Gln Ala Tyr Leu Glu Ala Gln Phe Gly
        355                 360                 365

gac caa gcc gcc gcc gtg gcg gcg tgc tat ccc ctc gac ggc cgg gcc     1152
Asp Gln Ala Ala Ala Val Ala Ala Cys Tyr Pro Leu Asp Gly Arg Ala
    370                 375                 380

acg ccc aag gaa atg gtc gcg cgc atc ttc ggc gac aat cag ttc aat     1200
Thr Pro Lys Glu Met Val Ala Arg Ile Phe Gly Asp Asn Gln Phe Asn
385                 390                 395                 400

cgg ggg gtc tcg gcc ttc tcg gaa gcg ctt gtg cgc cag ggc gcg ccc     1248
Arg Gly Val Ser Ala Phe Ser Glu Ala Leu Val Arg Gln Gly Ala Pro
                405                 410                 415

gtg tgg cgt tat cag ttc aac ggt aat acc gag ggt gga aga gcg ccg     1296
Val Trp Arg Tyr Gln Phe Asn Gly Asn Thr Glu Gly Gly Arg Ala Pro
            420                 425                 430

gct acc cac gga gcc gaa att ccc tac gtt ttc ggg gtg ttc aag ctc     1344
Ala Thr His Gly Ala Glu Ile Pro Tyr Val Phe Gly Val Phe Lys Leu
        435                 440                 445

gac gag ttg ggt ctg ttc gat tgg ccg ccc gag ggg ccc acg ccc gcc     1392
Asp Glu Leu Gly Leu Phe Asp Trp Pro Pro Glu Gly Pro Thr Pro Ala
    450                 455                 460

gac cgt gcg ctg ggc caa ctg atg tcc tcc gcc tgg gtc cgg ttc gcc     1440
Asp Arg Ala Leu Gly Gln Leu Met Ser Ser Ala Trp Val Arg Phe Ala
465                 470                 475                 480

aag aat ggc gac ccc gcc ggg gac gcc ctt acc tgg cct gcc tat tct     1488
Lys Asn Gly Asp Pro Ala Gly Asp Ala Leu Thr Trp Pro Ala Tyr Ser
                485                 490                 495

acg ggc aag tcg acc atg aca ttc ggt ccc gag ggc cgc gcg gcg gtg     1536
Thr Gly Lys Ser Thr Met Thr Phe Gly Pro Glu Gly Arg Ala Ala Val
            500                 505                 510

gtg tcg ccc gga cct tcc atc ccc cct tgc gcg gat ggc gcc aag gcg     1584
Val Ser Pro Gly Pro Ser Ile Pro Pro Cys Ala Asp Gly Ala Lys Ala
        515                 520                 525

ggg tga                                                             1590
```

-continued

Gly

<210> SEQ ID NO 3
<211> LENGTH: 529
<212> TYPE: PRT
<213> ORGANISM: Bacterium 2412.1

<400> SEQUENCE: 3

```
Met Gly Ala Arg Ser Met Cys Ala Gly Arg Phe Gly Arg Phe Cys Ile
  1               5                  10                  15

Gly Leu Ala Ser Ser Val Ala Val Thr Leu Gly Gly Ala Ser Ala Ala
             20                  25                  30

Gly Ala Ala Thr Ala Thr Asp Phe Pro Val Arg Arg Thr Asp Leu Gly
         35                  40                  45

Gln Val Gln Gly Leu Ala Gly Asp Val Met Ser Phe Arg Gly Ile Pro
     50                  55                  60

Tyr Ala Ala Pro Pro Val Gly Gly Leu Arg Trp Lys Pro Pro Gln His
 65                  70                  75                  80

Ala Arg Pro Trp Ala Gly Val Arg Pro Ala Thr Gln Phe Gly Ser Asp
                 85                  90                  95

Cys Phe Gly Ala Ala Tyr Leu Arg Lys Gly Ser Leu Ala Pro Gly Val
            100                 105                 110

Ser Glu Asp Cys Leu Tyr Leu Asn Val Trp Ala Pro Ser Gly Ala Lys
        115                 120                 125

Pro Gly Gln Tyr Pro Val Met Val Trp Val Tyr Gly Gly Gly Phe Ala
    130                 135                 140

Gly Gly Thr Ala Ala Met Pro Tyr Tyr Asp Gly Glu Ala Leu Ala Arg
145                 150                 155                 160

Gln Gly Val Val Val Val Thr Phe Asn Tyr Arg Thr Asn Ile Leu Gly
                165                 170                 175

Phe Phe Ala His Pro Gly Leu Ser Arg Glu Ser Pro Thr Gly Thr Ser
            180                 185                 190

Gly Asn Tyr Gly Leu Leu Asp Ile Leu Ala Ala Leu Arg Trp Val Gln
        195                 200                 205

Ser Asn Ala Arg Ala Phe Gly Gly Asp Pro Gly Arg Val Thr Val Phe
    210                 215                 220

Gly Glu Ser Ala Gly Ala Ser Ala Ile Gly Leu Leu Leu Thr Ser Pro
225                 230                 235                 240

Leu Ser Lys Gly Leu Phe Arg Gly Ala Ile Leu Glu Ser Pro Gly Leu
                245                 250                 255

Thr Arg Pro Leu Ala Thr Leu Ala Asp Ser Ala Ala Ser Gly Glu Arg
            260                 265                 270

Leu Asp Ala Asp Leu Ser Arg Leu Arg Ser Thr Asp Pro Ala Thr Leu
        275                 280                 285

Met Ala Arg Ala Asp Ala Ala Arg Pro Ala Ser Arg Asp Leu Arg Arg
    290                 295                 300

Pro Arg Pro Thr Gly Pro Ile Val Asp Gly His Val Leu Pro Gln Thr
305                 310                 315                 320

Asp Ser Ala Ala Ile Ala Ala Gly Gln Leu Ala Pro Val Arg Val Leu
                325                 330                 335

Ile Gly Thr Asn Ala Asp Glu Gly Arg Ala Phe Leu Gly Arg Ala Pro
            340                 345                 350

Met Glu Thr Pro Ala Asp Tyr Gln Ala Tyr Leu Glu Ala Gln Phe Gly
        355                 360                 365
```

-continued

```
Asp Gln Ala Ala Ala Val Ala Ala Cys Tyr Pro Leu Asp Gly Arg Ala
    370                 375                 380

Thr Pro Lys Glu Met Val Ala Arg Ile Phe Gly Asp Asn Gln Phe Asn
385                 390                 395                 400

Arg Gly Val Ser Ala Phe Ser Glu Ala Leu Val Arg Gln Gly Ala Pro
                405                 410                 415

Val Trp Arg Tyr Gln Phe Asn Gly Asn Thr Glu Gly Gly Arg Ala Pro
            420                 425                 430

Ala Thr His Gly Ala Glu Ile Pro Tyr Val Phe Gly Val Phe Lys Leu
        435                 440                 445

Asp Glu Leu Gly Leu Phe Asp Trp Pro Pro Glu Gly Pro Thr Pro Ala
    450                 455                 460

Asp Arg Ala Leu Gly Gln Leu Met Ser Ser Ala Trp Val Arg Phe Ala
465                 470                 475                 480

Lys Asn Gly Asp Pro Ala Gly Asp Ala Leu Thr Trp Pro Ala Tyr Ser
                485                 490                 495

Thr Gly Lys Ser Thr Met Thr Phe Gly Pro Glu Gly Arg Ala Ala Val
            500                 505                 510

Val Ser Pro Gly Pro Ser Ile Pro Pro Cys Ala Asp Gly Ala Lys Ala
        515                 520                 525

Gly


<210> SEQ ID NO 4
<211> LENGTH: 1290
<212> TYPE: DNA
<213> ORGANISM: Bacterium 2412.1
<220> FEATURE:
<223> OTHER INFORMATION: fccB Citrate Transport nucleotide
<221> NAME/KEY: CDS
<222> LOCATION: (1)..(1287)

<400> SEQUENCE: 4

atg acg gcc gcg gag gag cgc cgc ggg cat ttg ggt aag atc ctg cgc       48
Met Thr Ala Ala Glu Glu Arg Arg Gly His Leu Gly Lys Ile Leu Arg
  1               5                  10                  15

gtg gcg agc ggc aac ttc ctc gag cag tac gac ttc ttc atc tac ggc       96
Val Ala Ser Gly Asn Phe Leu Glu Gln Tyr Asp Phe Phe Ile Tyr Gly
            20                  25                  30

tac tac gcg acc tac atc gcc cag gtg ttc ttt cca tcg ggc gac gag      144
Tyr Tyr Ala Thr Tyr Ile Ala Gln Val Phe Phe Pro Ser Gly Asp Glu
        35                  40                  45

acg acg tcg ttg atg ctc tcc ctg gcc acc ttt ggc gtc ggg ttc ctg      192
Thr Thr Ser Leu Met Leu Ser Leu Ala Thr Phe Gly Val Gly Phe Leu
     50                  55                  60

atg cgg ccg cta ggg gcg atc att ctc gga tcc tac ata gat cgc gtc      240
Met Arg Pro Leu Gly Ala Ile Ile Leu Gly Ser Tyr Ile Asp Arg Val
 65                  70                  75                  80

ggc cgc cgg cag ggc ttg atc gtc acg ttg ggg atc atg gcg atc ggc      288
Gly Arg Arg Gln Gly Leu Ile Val Thr Leu Gly Ile Met Ala Ile Gly
                 85                  90                  95

acg ctc acc atc gcc ctg acg ccg ggt tac agc gcc atc ggg atc gcc      336
Thr Leu Thr Ile Ala Leu Thr Pro Gly Tyr Ser Ala Ile Gly Ile Ala
            100                 105                 110

gcg ccg ctc atc gtc gtc gcc ggt agg ctc ttg cag ggc ttc tcc gcc      384
Ala Pro Leu Ile Val Val Ala Gly Arg Leu Leu Gln Gly Phe Ser Ala
        115                 120                 125

gga gcc gaa ctc ggc ggc gtc tcg atc tac ctg gcg gaa atc gca aag      432
Gly Ala Glu Leu Gly Gly Val Ser Ile Tyr Leu Ala Glu Ile Ala Lys
    130                 135                 140
```

-continued

```
cct ggt cga cgg ggc ttc tac acc tcc tgg cag tcg gcc agc cag cag      480
Pro Gly Arg Arg Gly Phe Tyr Thr Ser Trp Gln Ser Ala Ser Gln Gln
145                 150                 155                 160

gtc gcg gtg atg gcg gcc gcg ctt gtc ggt cta agc ctc ggc gca aca      528
Val Ala Val Met Ala Ala Ala Leu Val Gly Leu Ser Leu Gly Ala Thr
                165                 170                 175

ttg acg ccc gac caa atg cac cag tgg ggc tgg cgc gtt ccg ttg ctg      576
Leu Thr Pro Asp Gln Met His Gln Trp Gly Trp Arg Val Pro Leu Leu
            180                 185                 190

ctc ggc tgt gcg atc gtc ccc gtc atc ctg tgg ctc cgc cga tcg ctc      624
Leu Gly Cys Ala Ile Val Pro Val Ile Leu Trp Leu Arg Arg Ser Leu
        195                 200                 205

gac gag acc gag gcc tat aaa cac att cat cac aag gcc cat tcc cta      672
Asp Glu Thr Glu Ala Tyr Lys His Ile His His Lys Ala His Ser Leu
    210                 215                 220

ttg ggc tcg ctg gcc cag ttg ggg ggc agc tgg agg ccg atc ttg gcc      720
Leu Gly Ser Leu Ala Gln Leu Gly Gly Ser Trp Arg Pro Ile Leu Ala
225                 230                 235                 240

ggc atg gcg atc tcg gtc ctg acc acc acg acc ttc tat atg atc acc      768
Gly Met Ala Ile Ser Val Leu Thr Thr Thr Thr Phe Tyr Met Ile Thr
                245                 250                 255

gcc tac acg ccg acc ttc gga aag cag gct ctc ggt ttg gac gcc cag      816
Ala Tyr Thr Pro Thr Phe Gly Lys Gln Ala Leu Gly Leu Asp Ala Gln
            260                 265                 270

gac gtc ctc gtc gtc acc atg ctg gtc ggc gcc tcg aac ttt ata tgg      864
Asp Val Leu Val Val Thr Met Leu Val Gly Ala Ser Asn Phe Ile Trp
        275                 280                 285

ctg ccg gtc ggc ggc gcg ctc tcc gac tgg att ggg cgc acg ccg gtg      912
Leu Pro Val Gly Gly Ala Leu Ser Asp Trp Ile Gly Arg Thr Pro Val
    290                 295                 300

ctc ctc tct gtg ccc ctg gtg gtc ctt gtc gcg gcc tac ccg ctg atc      960
Leu Leu Ser Val Pro Leu Val Val Leu Val Ala Ala Tyr Pro Leu Ile
305                 310                 315                 320

gcc tgg ctg gtg ggc gcg cca tcg ttc ttc gcg ttc gcg acg gcg ctg     1008
Ala Trp Leu Val Gly Ala Pro Ser Phe Phe Ala Phe Ala Thr Ala Leu
                325                 330                 335

ctg gcc ttg tcg gtc tgc ttt ggc ctc tat aac ggc gcg atg atc gca     1056
Leu Ala Leu Ser Val Cys Phe Gly Leu Tyr Asn Gly Ala Met Ile Ala
            340                 345                 350

cga ctg acc gaa ctg atg ccg cct gcg gca cgg acg ctg ggg ttt tcc     1104
Arg Leu Thr Glu Leu Met Pro Pro Ala Ala Arg Thr Leu Gly Phe Ser
        355                 360                 365

ctg gcg ttc agt ctg gcc acg tcg ctg ttc gga ggc ttc acg ccg ctg     1152
Leu Ala Phe Ser Leu Ala Thr Ser Leu Phe Gly Gly Phe Thr Pro Leu
    370                 375                 380

gtc agc act tat ctg atc agc gcg acc ggt aac aag gcc gca ccc gcg     1200
Val Ser Thr Tyr Leu Ile Ser Ala Thr Gly Asn Lys Ala Ala Pro Ala
385                 390                 395                 400

ctg tgg ctg tgc ttc gcc gcg atg atc agc ctg atc ggg gta ttg gct     1248
Leu Trp Leu Cys Phe Ala Ala Met Ile Ser Leu Ile Gly Val Leu Ala
                405                 410                 415

tca cgc agg atg ggg gcc gac ccc gat cga tcc atg gct tga             1290
Ser Arg Arg Met Gly Ala Asp Pro Asp Arg Ser Met Ala
            420                 425
```

<210> SEQ ID NO 5
<211> LENGTH: 429
<212> TYPE: PRT
<213> ORGANISM: Bacterium 2412.1

-continued

<400> SEQUENCE: 5

```
Met Thr Ala Ala Glu Glu Arg Arg Gly His Leu Gly Lys Ile Leu Arg
  1               5                  10                  15

Val Ala Ser Gly Asn Phe Leu Glu Gln Tyr Asp Phe Phe Ile Tyr Gly
             20                  25                  30

Tyr Tyr Ala Thr Tyr Ile Ala Gln Val Phe Phe Pro Ser Gly Asp Glu
         35                  40                  45

Thr Thr Ser Leu Met Leu Ser Leu Ala Thr Phe Gly Val Gly Phe Leu
     50                  55                  60

Met Arg Pro Leu Gly Ala Ile Ile Leu Gly Ser Tyr Ile Asp Arg Val
 65                  70                  75                  80

Gly Arg Arg Gln Gly Leu Ile Val Thr Leu Gly Ile Met Ala Ile Gly
                 85                  90                  95

Thr Leu Thr Ile Ala Leu Thr Pro Gly Tyr Ser Ala Ile Gly Ile Ala
            100                 105                 110

Ala Pro Leu Ile Val Val Ala Gly Arg Leu Leu Gln Gly Phe Ser Ala
        115                 120                 125

Gly Ala Glu Leu Gly Gly Val Ser Ile Tyr Leu Ala Glu Ile Ala Lys
    130                 135                 140

Pro Gly Arg Arg Gly Phe Tyr Thr Ser Trp Gln Ser Ala Ser Gln Gln
145                 150                 155                 160

Val Ala Val Met Ala Ala Ala Leu Val Gly Leu Ser Leu Gly Ala Thr
                165                 170                 175

Leu Thr Pro Asp Gln Met His Gln Trp Gly Trp Arg Val Pro Leu Leu
            180                 185                 190

Leu Gly Cys Ala Ile Val Pro Val Ile Leu Trp Leu Arg Arg Ser Leu
        195                 200                 205

Asp Glu Thr Glu Ala Tyr Lys His Ile His His Lys Ala His Ser Leu
    210                 215                 220

Leu Gly Ser Leu Ala Gln Leu Gly Gly Ser Trp Arg Pro Ile Leu Ala
225                 230                 235                 240

Gly Met Ala Ile Ser Val Leu Thr Thr Thr Thr Phe Tyr Met Ile Thr
                245                 250                 255

Ala Tyr Thr Pro Thr Phe Gly Lys Gln Ala Leu Gly Leu Asp Ala Gln
            260                 265                 270

Asp Val Leu Val Val Thr Met Leu Val Gly Ala Ser Asn Phe Ile Trp
        275                 280                 285

Leu Pro Val Gly Gly Ala Leu Ser Asp Trp Ile Gly Arg Thr Pro Val
    290                 295                 300

Leu Leu Ser Val Pro Leu Val Val Leu Val Ala Ala Tyr Pro Leu Ile
305                 310                 315                 320

Ala Trp Leu Val Gly Ala Pro Ser Phe Phe Ala Phe Ala Thr Ala Leu
                325                 330                 335

Leu Ala Leu Ser Val Cys Phe Gly Leu Tyr Asn Gly Ala Met Ile Ala
            340                 345                 350

Arg Leu Thr Glu Leu Met Pro Pro Ala Ala Arg Thr Leu Gly Phe Ser
        355                 360                 365

Leu Ala Phe Ser Leu Ala Thr Ser Leu Phe Gly Gly Phe Thr Pro Leu
    370                 375                 380

Val Ser Thr Tyr Leu Ile Ser Ala Thr Gly Asn Lys Ala Ala Pro Ala
385                 390                 395                 400

Leu Trp Leu Cys Phe Ala Ala Met Ile Ser Leu Ile Gly Val Leu Ala
                405                 410                 415
```

-continued

```
Ser Arg Arg Met Gly Ala Asp Pro Asp Arg Ser Met Ala
            420                 425


<210> SEQ ID NO 6
<211> LENGTH: 1677
<212> TYPE: DNA
<213> ORGANISM: Bacterium 2412.1
<220> FEATURE:
<223> OTHER INFORMATION: fccC  Flavin Monooxygenase
<221> NAME/KEY: CDS
<222> LOCATION: (1)..(1674)

<400> SEQUENCE: 6

atg ggg cgt gag acc cag ccg ttc gtg ctt atc gtc ggc ggc ggt caa       48
Met Gly Arg Glu Thr Gln Pro Phe Val Leu Ile Val Gly Gly Gly Gln
  1               5                  10                  15

ggc ggt cta gcg ctt ggc gcg cgc ctc cgt cag ctc cag gtc ccg act       96
Gly Gly Leu Ala Leu Gly Ala Arg Leu Arg Gln Leu Gln Val Pro Thr
             20                  25                  30

ctg atc gtc gat cag cac cca cgg gtg ggg gac caa tgg cga tcg cgg      144
Leu Ile Val Asp Gln His Pro Arg Val Gly Asp Gln Trp Arg Ser Arg
         35                  40                  45

tac gca tcg ctc tgc ctg cac gat cca gtc tgg tac gac cac ctt cct      192
Tyr Ala Ser Leu Cys Leu His Asp Pro Val Trp Tyr Asp His Leu Pro
     50                  55                  60

tac ctg ccg ttt ccc gat act tgg ccg gtt tat acg ccc aag gac aag      240
Tyr Leu Pro Phe Pro Asp Thr Trp Pro Val Tyr Thr Pro Lys Asp Lys
 65                  70                  75                  80

atc ggc gat tgg ctc gaa gct tat gcg cag gcg atg gag ctg ctg gtc      288
Ile Gly Asp Trp Leu Glu Ala Tyr Ala Gln Ala Met Glu Leu Leu Val
                 85                  90                  95

tgg tgt tcg acc aga tgc gtg tcc gcc gtc tat gac gcc gaa gcc ggg      336
Trp Cys Ser Thr Arg Cys Val Ser Ala Val Tyr Asp Ala Glu Ala Gly
            100                 105                 110

cga tgg acc gtc acc ctg cgc cga ggc gag gag acc agc gtc atc cgc      384
Arg Trp Thr Val Thr Leu Arg Arg Gly Glu Glu Thr Ser Val Ile Arg
        115                 120                 125

ccc gcg cat ctg gtc ctg gcg acg ggc aac gcc ggc aag ccg cgc gtt      432
Pro Ala His Leu Val Leu Ala Thr Gly Asn Ala Gly Lys Pro Arg Val
    130                 135                 140

ccg cgc ttc aag ggc caa gcg cag ttc gaa ggt ccg atc ctg cac tcg      480
Pro Arg Phe Lys Gly Gln Ala Gln Phe Glu Gly Pro Ile Leu His Ser
145                 150                 155                 160

agc gcc tat cgg agc ggg gct gat ttc aaa gga cgg cgc gtg gcc gtg      528
Ser Ala Tyr Arg Ser Gly Ala Asp Phe Lys Gly Arg Arg Val Ala Val
                165                 170                 175

atc gga tcg aac aat tcg gcc cac gac atc tgc gca gac ctc gtg gcc      576
Ile Gly Ser Asn Asn Ser Ala His Asp Ile Cys Ala Asp Leu Val Ala
            180                 185                 190

cac ggc gtt gac gtc acc atg atc cag cgc agt tcg acc cat gtc gtc      624
His Gly Val Asp Val Thr Met Ile Gln Arg Ser Ser Thr His Val Val
        195                 200                 205

cgt tcc gaa acg gtc atg cgg acc atg ctc gcg ccg ctt tat tca gag      672
Arg Ser Glu Thr Val Met Arg Thr Met Leu Ala Pro Leu Tyr Ser Glu
    210                 215                 220

gag gcc ttg gcg gcc ggc ata ggc acg gag ctg gcc gac ctg ctt gtg      720
Glu Ala Leu Ala Ala Gly Ile Gly Thr Glu Leu Ala Asp Leu Leu Val
225                 230                 235                 240

gct tcc atg ccg tta cgc ctg cag gcc gaa ggc tat cgc gcc ctc cac      768
Ala Ser Met Pro Leu Arg Leu Gln Ala Glu Gly Tyr Arg Ala Leu His
                245                 250                 255
```

-continued

```
gtc gcg atc gcc gag cag gac gca gcg ttc tac gcc gcg ctc gag gcg      816
Val Ala Ile Ala Glu Gln Asp Ala Ala Phe Tyr Ala Ala Leu Glu Ala
            260                 265                 270

atc ggc ttc atg cat gac ttc ggc gag gac ggc acc ggc atg ccg ctg      864
Ile Gly Phe Met His Asp Phe Gly Glu Asp Gly Thr Gly Met Pro Leu
        275                 280                 285

aag tat ctt cgt cgc gcg tcg ggg tac tat atc gac gtc ggc gca tcc      912
Lys Tyr Leu Arg Arg Ala Ser Gly Tyr Tyr Ile Asp Val Gly Ala Ser
    290                 295                 300

gaa ctc ctg gcc agc ggg gcc ata aag ctg cgc tcc cgc gtc gag atc      960
Glu Leu Leu Ala Ser Gly Ala Ile Lys Leu Arg Ser Arg Val Glu Ile
305                 310                 315                 320

gat cac ttc gac acc gac ggc ctg gcc ctc tcg gac ggc agc aag gtc     1008
Asp His Phe Asp Thr Asp Gly Leu Ala Leu Ser Asp Gly Ser Lys Val
                325                 330                 335

gac gcc gac gcc gtc atc tgc gca acc ggt ttc ggc tcc atg gac gag     1056
Asp Ala Asp Ala Val Ile Cys Ala Thr Gly Phe Gly Ser Met Asp Glu
            340                 345                 350

tgg gcg gcc gaa ttg att tcc ccc gag gtc gcg gcc aag gtc gga agg     1104
Trp Ala Ala Glu Leu Ile Ser Pro Glu Val Ala Ala Lys Val Gly Arg
        355                 360                 365

gtc tgg ggc tat ggg tcc ggc acc cga ggc gat ccg ggc ccc tgg gag     1152
Val Trp Gly Tyr Gly Ser Gly Thr Arg Gly Asp Pro Gly Pro Trp Glu
    370                 375                 380

ggc gaa ctt cgg aac atg tgg aag ccc acc cgc cag cag ggc ttg tgg     1200
Gly Glu Leu Arg Asn Met Trp Lys Pro Thr Arg Gln Gln Gly Leu Trp
385                 390                 395                 400

ttc cag ggc gga aac ctg gcg caa acc cgc ttc tac tcc aga gcg ctc     1248
Phe Gln Gly Gly Asn Leu Ala Gln Thr Arg Phe Tyr Ser Arg Ala Leu
                405                 410                 415

gct ctg cag ttg aag ccc gac atg ctg att gcc gtg agt cta cgt tcg     1296
Ala Leu Gln Leu Lys Pro Asp Met Leu Ile Ala Val Ser Leu Arg Ser
            420                 425                 430

tca ccg act agg cgg cgg cga agc tca ctg atc ttg ctc cgc ggc gtc     1344
Ser Pro Thr Arg Arg Arg Arg Ser Ser Leu Ile Leu Leu Arg Gly Val
        435                 440                 445

cca gag gct cac gct cgc ctc tcc ctg gtc tat tgc ttc gcg aat ttg     1392
Pro Glu Ala His Ala Arg Leu Ser Leu Val Tyr Cys Phe Ala Asn Leu
    450                 455                 460

cgg ccg cag ctc gag atg ttc ggg caa gaa cgt cct gca ata ggc gac     1440
Arg Pro Gln Leu Glu Met Phe Gly Gln Glu Arg Pro Ala Ile Gly Asp
465                 470                 475                 480

gct cac ggt cag ggc ctc ttc gta gta gtc ctc ggt gat cgc acc gtt     1488
Ala His Gly Gln Gly Leu Phe Val Val Val Leu Gly Asp Arg Thr Val
                485                 490                 495

ttg gac aaa cga gat cgc cag aac cgc atc gac gat ctg gat gtt cgt     1536
Leu Asp Lys Arg Asp Arg Gln Asn Arg Ile Asp Asp Leu Asp Val Arg
            500                 505                 510

gtg aaa ctt ctt ctg cgg atc gcg cag aaa agg cat gtg gaa gat gcg     1584
Val Lys Leu Leu Leu Arg Ile Ala Gln Lys Arg His Val Glu Asp Ala
        515                 520                 525

gtc aag gcg ctg ata ggc cgc gcg agc gac ggc ttc cac ata ttc gcg     1632
Val Lys Ala Leu Ile Gly Arg Ala Ser Asp Gly Phe His Ile Phe Ala
    530                 535                 540

atc ggc ctg ccg tgt ctc gag ccc gcc aaa tcc acc cag gaa tag         1677
Ile Gly Leu Pro Cys Leu Glu Pro Ala Lys Ser Thr Gln Glu
545                 550                 555
```

<210> SEQ ID NO 7

-continued

<211> LENGTH: 558
<212> TYPE: PRT
<213> ORGANISM: Bacterium 2412.1

<400> SEQUENCE: 7

```
Met Gly Arg Glu Thr Gln Pro Phe Val Leu Ile Val Gly Gly Gly Gln
  1               5                  10                  15

Gly Gly Leu Ala Leu Gly Ala Arg Leu Arg Gln Leu Gln Val Pro Thr
             20                  25                  30

Leu Ile Val Asp Gln His Pro Arg Val Gly Asp Gln Trp Arg Ser Arg
         35                  40                  45

Tyr Ala Ser Leu Cys Leu His Asp Pro Val Trp Tyr Asp His Leu Pro
     50                  55                  60

Tyr Leu Pro Phe Pro Asp Thr Trp Pro Val Tyr Thr Pro Lys Asp Lys
 65                  70                  75                  80

Ile Gly Asp Trp Leu Glu Ala Tyr Ala Gln Ala Met Glu Leu Leu Val
                 85                  90                  95

Trp Cys Ser Thr Arg Cys Val Ser Ala Val Tyr Asp Ala Glu Ala Gly
            100                 105                 110

Arg Trp Thr Val Thr Leu Arg Arg Gly Glu Glu Thr Ser Val Ile Arg
        115                 120                 125

Pro Ala His Leu Val Leu Ala Thr Gly Asn Ala Gly Lys Pro Arg Val
    130                 135                 140

Pro Arg Phe Lys Gly Gln Ala Gln Phe Glu Gly Pro Ile Leu His Ser
145                 150                 155                 160

Ser Ala Tyr Arg Ser Gly Ala Asp Phe Lys Gly Arg Arg Val Ala Val
                165                 170                 175

Ile Gly Ser Asn Asn Ser Ala His Asp Ile Cys Ala Asp Leu Val Ala
            180                 185                 190

His Gly Val Asp Val Thr Met Ile Gln Arg Ser Ser Thr His Val Val
        195                 200                 205

Arg Ser Glu Thr Val Met Arg Thr Met Leu Ala Pro Leu Tyr Ser Glu
    210                 215                 220

Glu Ala Leu Ala Ala Gly Ile Gly Thr Glu Leu Ala Asp Leu Leu Val
225                 230                 235                 240

Ala Ser Met Pro Leu Arg Leu Gln Ala Glu Gly Tyr Arg Ala Leu His
                245                 250                 255

Val Ala Ile Ala Glu Gln Asp Ala Ala Phe Tyr Ala Ala Leu Glu Ala
            260                 265                 270

Ile Gly Phe Met His Asp Phe Gly Glu Asp Gly Thr Gly Met Pro Leu
        275                 280                 285

Lys Tyr Leu Arg Arg Ala Ser Gly Tyr Tyr Ile Asp Val Gly Ala Ser
    290                 295                 300

Glu Leu Leu Ala Ser Gly Ala Ile Lys Leu Arg Ser Arg Val Glu Ile
305                 310                 315                 320

Asp His Phe Asp Thr Asp Gly Leu Ala Leu Ser Asp Gly Ser Lys Val
                325                 330                 335

Asp Ala Asp Ala Val Ile Cys Ala Thr Gly Phe Gly Ser Met Asp Glu
            340                 345                 350

Trp Ala Ala Glu Leu Ile Ser Pro Glu Val Ala Ala Lys Val Gly Arg
        355                 360                 365

Val Trp Gly Tyr Gly Ser Gly Thr Arg Gly Asp Pro Gly Pro Trp Glu
    370                 375                 380

Gly Glu Leu Arg Asn Met Trp Lys Pro Thr Arg Gln Gln Gly Leu Trp
```

-continued

```
385                 390                 395                 400

Phe Gln Gly Gly Asn Leu Ala Gln Thr Arg Phe Tyr Ser Arg Ala Leu
                405                 410                 415

Ala Leu Gln Leu Lys Pro Asp Met Leu Ile Ala Val Ser Leu Arg Ser
            420                 425                 430

Ser Pro Thr Arg Arg Arg Arg Ser Ser Leu Ile Leu Leu Arg Gly Val
        435                 440                 445

Pro Glu Ala His Ala Arg Leu Ser Leu Val Tyr Cys Phe Ala Asn Leu
    450                 455                 460

Arg Pro Gln Leu Glu Met Phe Gly Gln Glu Arg Pro Ala Ile Gly Asp
465                 470                 475                 480

Ala His Gly Gln Gly Leu Phe Val Val Val Leu Gly Asp Arg Thr Val
                485                 490                 495

Leu Asp Lys Arg Asp Arg Gln Asn Arg Ile Asp Asp Leu Asp Val Arg
            500                 505                 510

Val Lys Leu Leu Leu Arg Ile Ala Gln Lys Arg His Val Glu Asp Ala
        515                 520                 525

Val Lys Ala Leu Ile Gly Arg Ala Ser Asp Gly Phe His Ile Phe Ala
    530                 535                 540

Ile Gly Leu Pro Cys Leu Glu Pro Ala Lys Ser Thr Gln Glu
545                 550                 555


<210> SEQ ID NO 8
<211> LENGTH: 1407
<212> TYPE: DNA
<213> ORGANISM: Bacterium 2412.1
<220> FEATURE:
<223> OTHER INFORMATION: fccD Aldehyde Dehydrogenase
<221> NAME/KEY: CDS
<222> LOCATION: (1)..(1404)

<400> SEQUENCE: 8

atg cta gag tac aag ctg ctg atc gac ggc cgc ctg gtc gcc ggc gca       48
Met Leu Glu Tyr Lys Leu Leu Ile Asp Gly Arg Leu Val Ala Gly Ala
  1               5                  10                  15

acg acg atg tcc gta atc aat ccc gcg act gaa acg ccg ctg gtg atc       96
Thr Thr Met Ser Val Ile Asn Pro Ala Thr Glu Thr Pro Leu Val Ile
            20                  25                  30

gat tgc ccc agg gcc gac cgc gac caa ctg gac gaa gcc gtc gcc gcc      144
Asp Cys Pro Arg Ala Asp Arg Asp Gln Leu Asp Glu Ala Val Ala Ala
        35                  40                  45

gcg gaa cgc gcc ttt cag agc tgg cgg gca acc acg ctc gag cag cgc      192
Ala Glu Arg Ala Phe Gln Ser Trp Arg Ala Thr Thr Leu Glu Gln Arg
     50                  55                  60

agg gcc acg ctc aac gcc atc gcc gac gca att gaa gcc gac cag tcg      240
Arg Ala Thr Leu Asn Ala Ile Ala Asp Ala Ile Glu Ala Asp Gln Ser
 65                  70                  75                  80

gcg ctg gcg cgt ttg ctg acg cag gaa cag ggc aag ccg ctc gca gac      288
Ala Leu Ala Arg Leu Leu Thr Gln Glu Gln Gly Lys Pro Leu Ala Asp
                 85                  90                  95

gcg atg ggc gag atc tac gcc tcc gcg gcc ttc ttc cgc tac ttc acc      336
Ala Met Gly Glu Ile Tyr Ala Ser Ala Ala Phe Phe Arg Tyr Phe Thr
            100                 105                 110

tcg ctc gat ctg ccg cct cgc gtg gtc aga gac gac gcg acg ggc cgc      384
Ser Leu Asp Leu Pro Pro Arg Val Val Arg Asp Asp Ala Thr Gly Arg
        115                 120                 125

gta gag gtg cat aga cgc ccc cta ggc gtg gtg ggc tgc atc gtc ccc      432
Val Glu Val His Arg Arg Pro Leu Gly Val Val Gly Cys Ile Val Pro
    130                 135                 140
```

-continued

```
tgg aat ttc ccg atg ctg ttg atg gcg ttc aag atc ccg gcg gcc ctg      480
Trp Asn Phe Pro Met Leu Leu Met Ala Phe Lys Ile Pro Ala Ala Leu
145                 150                 155                 160

ctg gcc ggc aac acg gtc atc ctc aag ccg gcg gcg acg acg cct ctg      528
Leu Ala Gly Asn Thr Val Ile Leu Lys Pro Ala Ala Thr Thr Pro Leu
            165                 170                 175

acg gcg ctt cgg ttt ggc gcc ttg gtc aag gat atc gtc cca ccg ggc      576
Thr Ala Leu Arg Phe Gly Ala Leu Val Lys Asp Ile Val Pro Pro Gly
        180                 185                 190

gtc att aac atc atc acc gac gcc gac gat ctc ggc gcg gaa atg acc      624
Val Ile Asn Ile Ile Thr Asp Ala Asp Asp Leu Gly Ala Glu Met Thr
      195                 200                 205

cgc cat cct ggc att cgc aaa atc agc ttc acc gga tcg acc cag acc      672
Arg His Pro Gly Ile Arg Lys Ile Ser Phe Thr Gly Ser Thr Gln Thr
    210                 215                 220

gga aaa aag gtc atg gcc ggc gcg gcc gaa ggc ctc aaa cgt ata tcg      720
Gly Lys Lys Val Met Ala Gly Ala Ala Glu Gly Leu Lys Arg Ile Ser
225                 230                 235                 240

ctt gag ttg ggc gga aac gac gct ctg atc gtc ctg gat gac gtc gac      768
Leu Glu Leu Gly Gly Asn Asp Ala Leu Ile Val Leu Asp Asp Val Asp
            245                 250                 255

ccc aag gaa gtc gct ccc agg gtg ttc gcc gcg gcc atg caa aac gcc      816
Pro Lys Glu Val Ala Pro Arg Val Phe Ala Ala Ala Met Gln Asn Ala
        260                 265                 270

ggt cag gtg tgc atc gcc gcc aaa cgg att tac gtc cat gag agc ctc      864
Gly Gln Val Cys Ile Ala Ala Lys Arg Ile Tyr Val His Glu Ser Leu
      275                 280                 285

tat gag gcc atg tgc gag gag ttc gcg cag ttg gcg gcc cgc acg gtc      912
Tyr Glu Ala Met Cys Glu Glu Phe Ala Gln Leu Ala Ala Arg Thr Val
    290                 295                 300

gtg ggc gat gga ctc gaa cag ggc gtt cag atg ggg ccg ctg cag aac      960
Val Gly Asp Gly Leu Glu Gln Gly Val Gln Met Gly Pro Leu Gln Asn
305                 310                 315                 320

cgg cgc cag ttc gag aag gtt ctt ggt cta atc gag cgt gcg agg acg     1008
Arg Arg Gln Phe Glu Lys Val Leu Gly Leu Ile Glu Arg Ala Arg Thr
            325                 330                 335

gac ggc cgc atc atc gcc ggc ggc cgc cgc aag ggc gac aag ggc tat     1056
Asp Gly Arg Ile Ile Ala Gly Gly Arg Arg Lys Gly Asp Lys Gly Tyr
        340                 345                 350

ttc atc gag ccc acc atc gta cgc gac atc gcc gaa ggc gct cag ctc     1104
Phe Ile Glu Pro Thr Ile Val Arg Asp Ile Ala Glu Gly Ala Gln Leu
      355                 360                 365

gtc gac gaa gag cag ttt ggc ccg gtg atg ccg gtg atc cgg tac tcc     1152
Val Asp Glu Glu Gln Phe Gly Pro Val Met Pro Val Ile Arg Tyr Ser
    370                 375                 380

gac ccc gtc gac gcc gtg cgc cgc gcc aac gcc tcg ccc tat ggt ctg     1200
Asp Pro Val Asp Ala Val Arg Arg Ala Asn Ala Ser Pro Tyr Gly Leu
385                 390                 395                 400

ggg gga tcc atc tgg tcc cgc aac gtc gtc cgc gcg tgg agc ctg gcc     1248
Gly Gly Ser Ile Trp Ser Arg Asn Val Val Arg Ala Trp Ser Leu Ala
            405                 410                 415

gcc gat atg gag gcc ggc tcg gtc tgg gtg aac aag cac gcc gac gtg     1296
Ala Asp Met Glu Ala Gly Ser Val Trp Val Asn Lys His Ala Asp Val
        420                 425                 430

cag ccc gat ctc ccg ctc ggc ggc gcc aag ttc tcg ggg atg ggc tcg     1344
Gln Pro Asp Leu Pro Leu Gly Gly Ala Lys Phe Ser Gly Met Gly Ser
      435                 440                 445

gag tta ggc gag gaa ggg ctg cac gag ttc acc caa gtg cag gtg ctg     1392
Glu Leu Gly Glu Glu Gly Leu His Glu Phe Thr Gln Val Gln Val Leu
```

-continued

```
    450                 455                 460

aat atg acg cgg tga                                                  1407
Asn Met Thr Arg
465


<210> SEQ ID NO 9
<211> LENGTH: 468
<212> TYPE: PRT
<213> ORGANISM: Bacterium 2412.1

<400> SEQUENCE: 9

Met Leu Glu Tyr Lys Leu Leu Ile Asp Gly Arg Leu Val Ala Gly Ala
  1               5                  10                  15

Thr Thr Met Ser Val Ile Asn Pro Ala Thr Glu Thr Pro Leu Val Ile
             20                  25                  30

Asp Cys Pro Arg Ala Asp Arg Asp Gln Leu Asp Glu Ala Val Ala Ala
        35                  40                  45

Ala Glu Arg Ala Phe Gln Ser Trp Arg Ala Thr Thr Leu Glu Gln Arg
     50                  55                  60

Arg Ala Thr Leu Asn Ala Ile Ala Asp Ala Ile Glu Ala Asp Gln Ser
 65                  70                  75                  80

Ala Leu Ala Arg Leu Leu Thr Gln Glu Gln Gly Lys Pro Leu Ala Asp
                 85                  90                  95

Ala Met Gly Glu Ile Tyr Ala Ser Ala Ala Phe Phe Arg Tyr Phe Thr
            100                 105                 110

Ser Leu Asp Leu Pro Pro Arg Val Val Arg Asp Asp Ala Thr Gly Arg
        115                 120                 125

Val Glu Val His Arg Arg Pro Leu Gly Val Val Gly Cys Ile Val Pro
    130                 135                 140

Trp Asn Phe Pro Met Leu Leu Met Ala Phe Lys Ile Pro Ala Ala Leu
145                 150                 155                 160

Leu Ala Gly Asn Thr Val Ile Leu Lys Pro Ala Ala Thr Thr Pro Leu
                165                 170                 175

Thr Ala Leu Arg Phe Gly Ala Leu Val Lys Asp Ile Val Pro Pro Gly
            180                 185                 190

Val Ile Asn Ile Ile Thr Asp Ala Asp Asp Leu Gly Ala Glu Met Thr
        195                 200                 205

Arg His Pro Gly Ile Arg Lys Ile Ser Phe Thr Gly Ser Thr Gln Thr
    210                 215                 220

Gly Lys Lys Val Met Ala Gly Ala Ala Glu Gly Leu Lys Arg Ile Ser
225                 230                 235                 240

Leu Glu Leu Gly Gly Asn Asp Ala Leu Ile Val Leu Asp Asp Val Asp
                245                 250                 255

Pro Lys Glu Val Ala Pro Arg Val Phe Ala Ala Ala Met Gln Asn Ala
            260                 265                 270

Gly Gln Val Cys Ile Ala Ala Lys Arg Ile Tyr Val His Glu Ser Leu
        275                 280                 285

Tyr Glu Ala Met Cys Glu Glu Phe Ala Gln Leu Ala Ala Arg Thr Val
    290                 295                 300

Val Gly Asp Gly Leu Glu Gln Gly Val Gln Met Gly Pro Leu Gln Asn
305                 310                 315                 320

Arg Arg Gln Phe Glu Lys Val Leu Gly Leu Ile Glu Arg Ala Arg Thr
                325                 330                 335

Asp Gly Arg Ile Ile Ala Gly Gly Arg Arg Lys Gly Asp Lys Gly Tyr
            340                 345                 350
```

-continued

```
Phe Ile Glu Pro Thr Ile Val Arg Asp Ile Ala Glu Gly Ala Gln Leu
        355                 360                 365

Val Asp Glu Glu Gln Phe Gly Pro Val Met Pro Val Ile Arg Tyr Ser
    370                 375                 380

Asp Pro Val Asp Ala Val Arg Arg Ala Asn Ala Ser Pro Tyr Gly Leu
385                 390                 395                 400

Gly Gly Ser Ile Trp Ser Arg Asn Val Val Arg Ala Trp Ser Leu Ala
                405                 410                 415

Ala Asp Met Glu Ala Gly Ser Val Trp Val Asn Lys His Ala Asp Val
            420                 425                 430

Gln Pro Asp Leu Pro Leu Gly Gly Ala Lys Phe Ser Gly Met Gly Ser
        435                 440                 445

Glu Leu Gly Glu Glu Gly Leu His Glu Phe Thr Gln Val Gln Val Leu
    450                 455                 460

Asn Met Thr Arg
465


<210> SEQ ID NO 10
<211> LENGTH: 939
<212> TYPE: DNA
<213> ORGANISM: Bacterium 2412.1
<220> FEATURE:
<223> OTHER INFORMATION: fccE Alcohol Dehydrogenase
<221> NAME/KEY: CDS
<222> LOCATION: (1)..(936)

<400> SEQUENCE: 10

atg aaa gcg gcc att tac cgg cgc ggg gag atc gtt gtc gat acc gtt       48
Met Lys Ala Ala Ile Tyr Arg Arg Gly Glu Ile Val Val Asp Thr Val
  1               5                  10                  15

ccc gat ccg gtt cca gga cca ggc cag gtt ctc gtc cgg agc ctt gtt       96
Pro Asp Pro Val Pro Gly Pro Gly Gln Val Leu Val Arg Ser Leu Val
             20                  25                  30

tgc ggg gta tgt ggt tcg gat ctg cat tac cga cat cac gca cac cgg      144
Cys Gly Val Cys Gly Ser Asp Leu His Tyr Arg His His Ala His Arg
         35                  40                  45

ttc gtc gat ctg gcc ttg cgc tcg ggc gcg ccc gcc ctg gcc gcc gat      192
Phe Val Asp Leu Ala Leu Arg Ser Gly Ala Pro Ala Leu Ala Ala Asp
     50                  55                  60

ttg gat cgc gat atc gtc ctt ggt cac gaa ttc agc gct caa gtc gtc      240
Leu Asp Arg Asp Ile Val Leu Gly His Glu Phe Ser Ala Gln Val Val
 65                  70                  75                  80

gac tac ggg cct aag acc gag cgt ctc ctg aag tcg gga acg gtc gtc      288
Asp Tyr Gly Pro Lys Thr Glu Arg Leu Leu Lys Ser Gly Thr Val Val
                 85                  90                  95

tgc tcg ccc ccc gtc gcg ttc ggg gcc agc ggc atg cgc gcc gtt ggc      336
Cys Ser Pro Pro Val Ala Phe Gly Ala Ser Gly Met Arg Ala Val Gly
            100                 105                 110

tac tcc gac gaa tta ccg ggc ggg ttt ggc cag tac atg gtc ttg aat      384
Tyr Ser Asp Glu Leu Pro Gly Gly Phe Gly Gln Tyr Met Val Leu Asn
        115                 120                 125

gag gcg ttc ctg atg ccg gcc cca aac gga ctg gat ccg gct cgc gcg      432
Glu Ala Phe Leu Met Pro Ala Pro Asn Gly Leu Asp Pro Ala Arg Ala
    130                 135                 140

gcg ctc acc gag ccg atg gcg gtg ggg tgg cac gcg gtg aag ctg gcc      480
Ala Leu Thr Glu Pro Met Ala Val Gly Trp His Ala Val Lys Leu Ala
145                 150                 155                 160

ggt ccc gga cgc gac cat atc ccg ctc gtg atc ggc tgc ggg ccc gtg      528
Gly Pro Gly Arg Asp His Ile Pro Leu Val Ile Gly Cys Gly Pro Val
```

-continued

```
                165                 170                 175

ggc atg gcg gtc atc gcc gcg ctc cgg ggt ctg ggc gtc gga ccg atc      576
Gly Met Ala Val Ile Ala Ala Leu Arg Gly Leu Gly Val Gly Pro Ile
            180                 185                 190

atc gcg gcc gac ttc aat ccg gcg cgt cgg agc ctg gcg gcg cgc atg      624
Ile Ala Ala Asp Phe Asn Pro Ala Arg Arg Ser Leu Ala Ala Arg Met
        195                 200                 205

ggc gcc gat att gtc atc gac ccg gcg gag cgg tcc ccc tac gac gaa      672
Gly Ala Asp Ile Val Ile Asp Pro Ala Glu Arg Ser Pro Tyr Asp Glu
    210                 215                 220

tgg cgg gat acc gcg gcg gcg tca ggc ctg gcc gga ctg gcg ggg gcg      720
Trp Arg Asp Thr Ala Ala Ala Ser Gly Leu Ala Gly Leu Ala Gly Ala
225                 230                 235                 240

cca gcg tcg ctg cgg acc tgt ctg gtc ttc gag tgt gtc ggc ctg cca      768
Pro Ala Ser Leu Arg Thr Cys Leu Val Phe Glu Cys Val Gly Leu Pro
                245                 250                 255

gga atg ctg cgt cag atc atg gaa ggc gcc ccg gcg gag tcg gag atc      816
Gly Met Leu Arg Gln Ile Met Glu Gly Ala Pro Ala Glu Ser Glu Ile
            260                 265                 270

atc gtc gtc ggg gcc tgc atg gag ccc gat agc ctc gag ccg atg atg      864
Ile Val Val Gly Ala Cys Met Glu Pro Asp Ser Leu Glu Pro Met Met
        275                 280                 285

gcg atg cat aag gct ctg acg ctg aat ttt cgc gaa cct aca cga tcg      912
Ala Met His Lys Ala Leu Thr Leu Asn Phe Arg Glu Pro Thr Arg Ser
    290                 295                 300

agg agt tcg ccg agg tcc ttc gga tga                                  939
Arg Ser Ser Pro Arg Ser Phe Gly
305                 310


<210> SEQ ID NO 11
<211> LENGTH: 312
<212> TYPE: PRT
<213> ORGANISM: Bacterium 2412.1

<400> SEQUENCE: 11

Met Lys Ala Ala Ile Tyr Arg Arg Gly Glu Ile Val Val Asp Thr Val
  1               5                  10                  15

Pro Asp Pro Val Pro Gly Pro Gly Gln Val Leu Val Arg Ser Leu Val
            20                  25                  30

Cys Gly Val Cys Gly Ser Asp Leu His Tyr Arg His His Ala His Arg
        35                  40                  45

Phe Val Asp Leu Ala Leu Arg Ser Gly Ala Pro Ala Leu Ala Ala Asp
     50                  55                  60

Leu Asp Arg Asp Ile Val Leu Gly His Glu Phe Ser Ala Gln Val Val
 65                  70                  75                  80

Asp Tyr Gly Pro Lys Thr Glu Arg Leu Leu Lys Ser Gly Thr Val Val
                85                  90                  95

Cys Ser Pro Pro Val Ala Phe Gly Ala Ser Gly Met Arg Ala Val Gly
            100                 105                 110

Tyr Ser Asp Glu Leu Pro Gly Gly Phe Gly Gln Tyr Met Val Leu Asn
        115                 120                 125

Glu Ala Phe Leu Met Pro Ala Pro Asn Gly Leu Asp Pro Ala Arg Ala
    130                 135                 140

Ala Leu Thr Glu Pro Met Ala Val Gly Trp His Ala Val Lys Leu Ala
145                 150                 155                 160

Gly Pro Gly Arg Asp His Ile Pro Leu Val Ile Gly Cys Gly Pro Val
                165                 170                 175
```

-continued

```
Gly Met Ala Val Ile Ala Ala Leu Arg Gly Leu Gly Val Gly Pro Ile
            180                 185                 190

Ile Ala Ala Asp Phe Asn Pro Ala Arg Arg Ser Leu Ala Ala Arg Met
        195                 200                 205

Gly Ala Asp Ile Val Ile Asp Pro Ala Glu Arg Ser Pro Tyr Asp Glu
    210                 215                 220

Trp Arg Asp Thr Ala Ala Ala Ser Gly Leu Ala Gly Leu Ala Gly Ala
225                 230                 235                 240

Pro Ala Ser Leu Arg Thr Cys Leu Val Phe Glu Cys Val Gly Leu Pro
                245                 250                 255

Gly Met Leu Arg Gln Ile Met Glu Gly Ala Pro Ala Glu Ser Glu Ile
            260                 265                 270

Ile Val Val Gly Ala Cys Met Glu Pro Asp Ser Leu Glu Pro Met Met
        275                 280                 285

Ala Met His Lys Ala Leu Thr Leu Asn Phe Arg Glu Pro Thr Arg Ser
    290                 295                 300

Arg Ser Ser Pro Arg Ser Phe Gly
305                 310


<210> SEQ ID NO 12
<211> LENGTH: 1377
<212> TYPE: DNA
<213> ORGANISM: Bacterium 2412.1
<220> FEATURE:
<223> OTHER INFORMATION: fccF CoA Ligase
<221> NAME/KEY: CDS
<222> LOCATION: (1)..(1374)

<400> SEQUENCE: 12

atg ctt ggc gcc gtc atc cag acg gtg aac atc cga cta gcc cga gac       48
Met Leu Gly Ala Val Ile Gln Thr Val Asn Ile Arg Leu Ala Arg Asp
  1               5                  10                  15

gac ctg cgc tac acg ctc gag cat gcg ggc gcc acc ctg gcg ctg agc       96
Asp Leu Arg Tyr Thr Leu Glu His Ala Gly Ala Thr Leu Ala Leu Ser
            20                  25                  30

cac acc gat ttc ctg ccg atc ctc gag gag gtg atc gac caa ttg ccc      144
His Thr Asp Phe Leu Pro Ile Leu Glu Glu Val Ile Asp Gln Leu Pro
        35                  40                  45

agc ctg cgc ggg gtc gtc cat ctg aag gac gac gag gcg gaa gcc gcc      192
Ser Leu Arg Gly Val Val His Leu Lys Asp Asp Glu Ala Glu Ala Ala
     50                  55                  60

cat ccc tgg gtg ctg ggg gag tat gag gcc ctg atg gcg gcc gcg cgc      240
His Pro Trp Val Leu Gly Glu Tyr Glu Ala Leu Met Ala Ala Ala Arg
 65                  70                  75                  80

cct cgg ttc gac ttc ccg gac ttc gac gag aac acg cgg gcg acg acc      288
Pro Arg Phe Asp Phe Pro Asp Phe Asp Glu Asn Thr Arg Ala Thr Thr
                 85                  90                  95

ttc tac acc agc ggc acg acc ggg cgt ccg aag ggc gtc tac tat tcg      336
Phe Tyr Thr Ser Gly Thr Thr Gly Arg Pro Lys Gly Val Tyr Tyr Ser
            100                 105                 110

cat cgt cag ctg gtg ctg cac acc ctg gcg gtg atg gcg acg ctg gcc      384
His Arg Gln Leu Val Leu His Thr Leu Ala Val Met Ala Thr Leu Ala
        115                 120                 125

ctt gga gac ggt tac gcc agg ctg ggg cgc gat acg gtc tac atg ccg      432
Leu Gly Asp Gly Tyr Ala Arg Leu Gly Arg Asp Thr Val Tyr Met Pro
    130                 135                 140

atc acc ccg atg ttc cat gct cat gcg tgg gga atg ccc ttc gtg gcg      480
Ile Thr Pro Met Phe His Ala His Ala Trp Gly Met Pro Phe Val Ala
145                 150                 155                 160
```

-continued

```
acg atg gtc ggc tgc aag caa gtc tac cca ggg cgc tat gtt ccc gag      528
Thr Met Val Gly Cys Lys Gln Val Tyr Pro Gly Arg Tyr Val Pro Glu
            165                 170                 175

caa ctg gtg gag ctt cag cgc gcg gag aag gtg acc ttc tct cat tgc      576
Gln Leu Val Glu Leu Gln Arg Ala Glu Lys Val Thr Phe Ser His Cys
            180                 185                 190

gtg ccc aca ctt ttg cag atg atg ctc aat tcg cct tcg ggc cag acg      624
Val Pro Thr Leu Leu Gln Met Met Leu Asn Ser Pro Ser Gly Gln Thr
        195                 200                 205

gcg gat ttc acc gga tgg cag gtg ctc gtc ggc gga gcg gcg ctg ccc      672
Ala Asp Phe Thr Gly Trp Gln Val Leu Val Gly Gly Ala Ala Leu Pro
    210                 215                 220

cgc ggc ctg gct ctt cag gcc gcg ggg cgc ggc atc gtc ctg acc acc      720
Arg Gly Leu Ala Leu Gln Ala Ala Gly Arg Gly Ile Val Leu Thr Thr
225                 230                 235                 240

gga tac gga atg tcc gaa acc ggg ccg ctg gtc agc ttc acg cgc att      768
Gly Tyr Gly Met Ser Glu Thr Gly Pro Leu Val Ser Phe Thr Arg Ile
            245                 250                 255

agg acc gaa gca atg gct cca gct cag gag gag gtc gcc att cgc acc      816
Arg Thr Glu Ala Met Ala Pro Ala Gln Glu Glu Val Ala Ile Arg Thr
            260                 265                 270

aag gtc gga caa gct atc gcg ctg gtc gac ctc cgg gtc gtg gat gag      864
Lys Val Gly Gln Ala Ile Ala Leu Val Asp Leu Arg Val Val Asp Glu
        275                 280                 285

tcc atg gcg gat gtg ccc cgc gac ggc ctc tcc gcg ggc gag atc gtg      912
Ser Met Ala Asp Val Pro Arg Asp Gly Leu Ser Ala Gly Glu Ile Val
    290                 295                 300

ttg cgt gcg cct tgg ctg acg gct ggg tac cat cgc gat ctg gcc gcc      960
Leu Arg Ala Pro Trp Leu Thr Ala Gly Tyr His Arg Asp Leu Ala Ala
305                 310                 315                 320

tcg cgc gag ctt tgg cgc gga gga agc ctt cat acg cag gat ttc ggc     1008
Ser Arg Glu Leu Trp Arg Gly Gly Ser Leu His Thr Gln Asp Phe Gly
            325                 330                 335

cgg att gac gcg gag ggc tac ctg cag atc agc gac cgc ctc cag gga     1056
Arg Ile Asp Ala Glu Gly Tyr Leu Gln Ile Ser Asp Arg Leu Gln Gly
            340                 345                 350

gtc atc aag acg gtg ggg atg ggt tct cct gag ctg gga gat ctc gtc     1104
Val Ile Lys Thr Val Gly Met Gly Ser Pro Glu Leu Gly Asp Leu Val
        355                 360                 365

agc cgc cat ccg gcg gtg ctg gag agc gcc gcg atc gct gtc gcc gac     1152
Ser Arg His Pro Ala Val Leu Glu Ser Ala Ala Ile Ala Val Ala Asp
    370                 375                 380

gag cgt tgg gga gag cgc cca gcg atg gtc gtc gtg ctc agg ccg ggc     1200
Glu Arg Trp Gly Glu Arg Pro Ala Met Val Val Val Leu Arg Pro Gly
385                 390                 395                 400

atg agc gcg acc acg gcg gac atc cga gac cac ctt tca tcg tat gtc     1248
Met Ser Ala Thr Thr Ala Asp Ile Arg Asp His Leu Ser Ser Tyr Val
            405                 410                 415

gcg acc ggc gaa ata cct cgc tac gcc gtg ccc gag cag atc tgg ttc     1296
Ala Thr Gly Glu Ile Pro Arg Tyr Ala Val Pro Glu Gln Ile Trp Phe
            420                 425                 430

gtc gag gag ctc gac cga acg agc gtg ggc aag gtc gac aag cgg gcg     1344
Val Glu Glu Leu Asp Arg Thr Ser Val Gly Lys Val Asp Lys Arg Ala
        435                 440                 445

ctt cgt tcc agg ttc gcc gaa gcg gcg tcc tga                         1377
Leu Arg Ser Arg Phe Ala Glu Ala Ala Ser
    450                 455
```

<210> SEQ ID NO 13
<211> LENGTH: 458

-continued

<212> TYPE: PRT
<213> ORGANISM: Bacterium 2412.1

<400> SEQUENCE: 13

Met Leu Gly Ala Val Ile Gln Thr Val Asn Ile Arg Leu Ala Arg Asp
1 5 10 15

Asp Leu Arg Tyr Thr Leu Glu His Ala Gly Ala Thr Leu Ala Leu Ser
20 25 30

His Thr Asp Phe Leu Pro Ile Leu Glu Glu Val Ile Asp Gln Leu Pro
35 40 45

Ser Leu Arg Gly Val Val His Leu Lys Asp Asp Glu Ala Glu Ala Ala
50 55 60

His Pro Trp Val Leu Gly Glu Tyr Glu Ala Leu Met Ala Ala Ala Arg
65 70 75 80

Pro Arg Phe Asp Phe Pro Asp Phe Asp Glu Asn Thr Arg Ala Thr Thr
85 90 95

Phe Tyr Thr Ser Gly Thr Thr Gly Arg Pro Lys Gly Val Tyr Tyr Ser
100 105 110

His Arg Gln Leu Val Leu His Thr Leu Ala Val Met Ala Thr Leu Ala
115 120 125

Leu Gly Asp Gly Tyr Ala Arg Leu Gly Arg Asp Thr Val Tyr Met Pro
130 135 140

Ile Thr Pro Met Phe His Ala His Ala Trp Gly Met Pro Phe Val Ala
145 150 155 160

Thr Met Val Gly Cys Lys Gln Val Tyr Pro Gly Arg Tyr Val Pro Glu
165 170 175

Gln Leu Val Glu Leu Gln Arg Ala Glu Lys Val Thr Phe Ser His Cys
180 185 190

Val Pro Thr Leu Leu Gln Met Met Leu Asn Ser Pro Ser Gly Gln Thr
195 200 205

Ala Asp Phe Thr Gly Trp Gln Val Leu Val Gly Gly Ala Ala Leu Pro
210 215 220

Arg Gly Leu Ala Leu Gln Ala Ala Gly Arg Gly Ile Val Leu Thr Thr
225 230 235 240

Gly Tyr Gly Met Ser Glu Thr Gly Pro Leu Val Ser Phe Thr Arg Ile
245 250 255

Arg Thr Glu Ala Met Ala Pro Ala Gln Glu Glu Val Ala Ile Arg Thr
260 265 270

Lys Val Gly Gln Ala Ile Ala Leu Val Asp Leu Arg Val Val Asp Glu
275 280 285

Ser Met Ala Asp Val Pro Arg Asp Gly Leu Ser Ala Gly Glu Ile Val
290 295 300

Leu Arg Ala Pro Trp Leu Thr Ala Gly Tyr His Arg Asp Leu Ala Ala
305 310 315 320

Ser Arg Glu Leu Trp Arg Gly Gly Ser Leu His Thr Gln Asp Phe Gly
325 330 335

Arg Ile Asp Ala Glu Gly Tyr Leu Gln Ile Ser Asp Arg Leu Gln Gly
340 345 350

Val Ile Lys Thr Val Gly Met Gly Ser Pro Glu Leu Gly Asp Leu Val
355 360 365

Ser Arg His Pro Ala Val Leu Glu Ser Ala Ala Ile Ala Val Ala Asp
370 375 380

Glu Arg Trp Gly Glu Arg Pro Ala Met Val Val Val Leu Arg Pro Gly
385 390 395 400

-continued

```
Met Ser Ala Thr Thr Ala Asp Ile Arg Asp His Leu Ser Ser Tyr Val
                405                 410                 415

Ala Thr Gly Glu Ile Pro Arg Tyr Ala Val Pro Glu Gln Ile Trp Phe
            420                 425                 430

Val Glu Glu Leu Asp Arg Thr Ser Val Gly Lys Val Asp Lys Arg Ala
        435                 440                 445

Leu Arg Ser Arg Phe Ala Glu Ala Ala Ser
    450                 455


<210> SEQ ID NO 14
<211> LENGTH: 1632
<212> TYPE: DNA
<213> ORGANISM: Bacterium 2412.1
<220> FEATURE:
<223> OTHER INFORMATION: fccG Acetohydroxyacid  synthase
<221> NAME/KEY: CDS
<222> LOCATION: (1)..(1629)

<400> SEQUENCE: 14

atg tcg ccg gag gtt gat ccg ctg ctg gcg gcg ctc gac gac aac ggc       48
Met Ser Pro Glu Val Asp Pro Leu Leu Ala Ala Leu Asp Asp Asn Gly
  1               5                  10                  15

atc cgc ttc atc ccc gtg cgg cat gag gcg gct gcg gcc tat atg gcc       96
Ile Arg Phe Ile Pro Val Arg His Glu Ala Ala Ala Ala Tyr Met Ala
            20                  25                  30

gag ggt ctc tac aag acg aca ggc caa gtc gcc gcc acc gtg aca aac      144
Glu Gly Leu Tyr Lys Thr Thr Gly Gln Val Ala Ala Thr Val Thr Asn
        35                  40                  45

cca gga ccc ggt acg gca aac ctg ctg ccc ggc ttg gtg acc gcc aag      192
Pro Gly Pro Gly Thr Ala Asn Leu Leu Pro Gly Leu Val Thr Ala Lys
     50                  55                  60

cat gag ggc gtg ccg atg atc gcc atc acc gcg cag cat cat ggc ggg      240
His Glu Gly Val Pro Met Ile Ala Ile Thr Ala Gln His His Gly Gly
 65                  70                  75                  80

gtc gtc tat ccc gcg acg ccc agc acg ttc cag ggc gcc gac caa ttg      288
Val Val Tyr Pro Ala Thr Pro Ser Thr Phe Gln Gly Ala Asp Gln Leu
                 85                  90                  95

gaa ctc ctg cgc ccg gcg gtc aaa tgg ggc gcg ccc att cat acc tgg      336
Glu Leu Leu Arg Pro Ala Val Lys Trp Gly Ala Pro Ile His Thr Trp
            100                 105                 110

caa cgc atc ggc gag gtt acg cgc atg gcg ttc cgg gag atg tgg gcg      384
Gln Arg Ile Gly Glu Val Thr Arg Met Ala Phe Arg Glu Met Trp Ala
        115                 120                 125

ggg cgt ccc ggc ccg gtc cag atc gat gtt ccg agc cca gtg atg tac      432
Gly Arg Pro Gly Pro Val Gln Ile Asp Val Pro Ser Pro Val Met Tyr
    130                 135                 140

gac atg acc gac gag tcc cgg gct ggc ctg ctc gat ccg atc gcc tat      480
Asp Met Thr Asp Glu Ser Arg Ala Gly Leu Leu Asp Pro Ile Ala Tyr
145                 150                 155                 160

cgg gcg ccc cct cct tca gcc ggc ggc tcg caa atc aac gcc gcc gcc      528
Arg Ala Pro Pro Pro Ser Ala Gly Gly Ser Gln Ile Asn Ala Ala Ala
                165                 170                 175

caa ttg ctg gcc gcc gcg act cgt ccg ctg atc atg gtc ggc tcc ggg      576
Gln Leu Leu Ala Ala Ala Thr Arg Pro Leu Ile Met Val Gly Ser Gly
            180                 185                 190

gtc gac cga gct ggc gcg ggc gag gct gtg ctg cgc cta gcc gac aag      624
Val Asp Arg Ala Gly Ala Gly Glu Ala Val Leu Arg Leu Ala Asp Lys
        195                 200                 205

ctg ggt tgc ggc gtc atc gcc agc ctg gcg ggc cgg tcg gcc gtc cct      672
Leu Gly Cys Gly Val Ile Ala Ser Leu Ala Gly Arg Ser Ala Val Pro
```

-continued

```
    210                 215                 220

caa gat cac ccc ctc cac ctg cac gcc tat ggc gcc ggc gct gat cag      720
Gln Asp His Pro Leu His Leu His Ala Tyr Gly Ala Gly Ala Asp Gln
225                 230                 235                 240

gcg cga cgc gaa gcc gac gtc atc ctg gcg ctg ggc acg cgc ctg gga      768
Ala Arg Arg Glu Ala Asp Val Ile Leu Ala Leu Gly Thr Arg Leu Gly
                245                 250                 255

aac atc gac acg ccc ttc gac cgc tat tgg ggc tca tcg gag ggg cac      816
Asn Ile Asp Thr Pro Phe Asp Arg Tyr Trp Gly Ser Ser Glu Gly His
            260                 265                 270

aag ctg atc cag gtc gat atc gac ccc cgc aat ttg ggc gcc tca cgt      864
Lys Leu Ile Gln Val Asp Ile Asp Pro Arg Asn Leu Gly Ala Ser Arg
        275                 280                 285

ccg ttg acg cta ggc atc gtt tcg gac gcg ggc agc ctc gtg gaa ggc      912
Pro Leu Thr Leu Gly Ile Val Ser Asp Ala Gly Ser Leu Val Glu Gly
    290                 295                 300

ctc ctc gag gcc ctc gag aac gcg ccc acg cgc tcg ggc gcg gac gtc      960
Leu Leu Glu Ala Leu Glu Asn Ala Pro Thr Arg Ser Gly Ala Asp Val
305                 310                 315                 320

gac ctc acg cgc tat cgc caa atg gac gcc gaa tgg cgg cgt tcc gag     1008
Asp Leu Thr Arg Tyr Arg Gln Met Asp Ala Glu Trp Arg Arg Ser Glu
                325                 330                 335

ttc gct cat atc gag gcc cat ggc ggt cca agt cct cac ccg gct gag     1056
Phe Ala His Ile Glu Ala His Gly Gly Pro Ser Pro His Pro Ala Glu
            340                 345                 350

gtt atg cag acg gtg gga gag gtt ttc ggt ccc gat gcg gtg tac gtc     1104
Val Met Gln Thr Val Gly Glu Val Phe Gly Pro Asp Ala Val Tyr Val
        355                 360                 365

gcc gat ggc ggt ttc acg agc ctt tgg gct cac ttt atg ttg ccc tcg     1152
Ala Asp Gly Gly Phe Thr Ser Leu Trp Ala His Phe Met Leu Pro Ser
    370                 375                 380

acc aga ccg cgc tcg tac ctg aac att ctt gag atg ggg atg ctg ggc     1200
Thr Arg Pro Arg Ser Tyr Leu Asn Ile Leu Glu Met Gly Met Leu Gly
385                 390                 395                 400

acc ggc ata ccg tct gcg atc ggc gcg ggt ctc gga agc ccg gat cgc     1248
Thr Gly Ile Pro Ser Ala Ile Gly Ala Gly Leu Gly Ser Pro Asp Arg
                405                 410                 415

cag atc gtc tgc gtt act ggc gac ggc gcg gcc ggc ttc cat tgt atg     1296
Gln Ile Val Cys Val Thr Gly Asp Gly Ala Ala Gly Phe His Cys Met
            420                 425                 430

gaa ctg cag tcc gcc gtc cgc gag gac gtc aag gtg acc gtc gtc gtc     1344
Glu Leu Gln Ser Ala Val Arg Glu Asp Val Lys Val Thr Val Val Val
        435                 440                 445

ctg gcc gaa ggg tcg tgg tcg atg gag gtc ccg aat gag cag gcg cgc     1392
Leu Ala Glu Gly Ser Trp Ser Met Glu Val Pro Asn Glu Gln Ala Arg
    450                 455                 460

tac ggc agg acc ttc ggc acc gag atg ggc ccc gtc ctc tgg gaa agg     1440
Tyr Gly Arg Thr Phe Gly Thr Glu Met Gly Pro Val Leu Trp Glu Arg
465                 470                 475                 480

ttg gcc gaa agc ctg gga tgc ttc ggc ttc aag gcc gag acc gcg ccg     1488
Leu Ala Glu Ser Leu Gly Cys Phe Gly Phe Lys Ala Glu Thr Ala Pro
                485                 490                 495

gat ctg cgg ccc gct ctg agc gcg gcg cgc gat gcg ctc gga ccg gcc     1536
Asp Leu Arg Pro Ala Leu Ser Ala Ala Arg Asp Ala Leu Gly Pro Ala
            500                 505                 510

ctt gtg cgg gtc cgg aca gat agg gct gcg aac ctg gcc ttt ccc ccg     1584
Leu Val Arg Val Arg Thr Asp Arg Ala Ala Asn Leu Ala Phe Pro Pro
        515                 520                 525

tcg atc gcc atg cgc ttc cac gag ggc tat cag ggc ctg acc ggt tga     1632
```

-continued

```
Ser Ile Ala Met Arg Phe His Glu Gly Tyr Gln Gly Leu Thr Gly
    530                 535                 540


<210> SEQ ID NO 15
<211> LENGTH: 543
<212> TYPE: PRT
<213> ORGANISM: Bacterium 2412.1

<400> SEQUENCE: 15

Met Ser Pro Glu Val Asp Pro Leu Leu Ala Ala Leu Asp Asp Asn Gly
  1               5                  10                  15

Ile Arg Phe Ile Pro Val Arg His Glu Ala Ala Ala Ala Tyr Met Ala
             20                  25                  30

Glu Gly Leu Tyr Lys Thr Thr Gly Gln Val Ala Ala Thr Val Thr Asn
         35                  40                  45

Pro Gly Pro Gly Thr Ala Asn Leu Leu Pro Gly Leu Val Thr Ala Lys
     50                  55                  60

His Glu Gly Val Pro Met Ile Ala Ile Thr Ala Gln His His Gly Gly
 65                  70                  75                  80

Val Val Tyr Pro Ala Thr Pro Ser Thr Phe Gln Gly Ala Asp Gln Leu
                 85                  90                  95

Glu Leu Leu Arg Pro Ala Val Lys Trp Gly Ala Pro Ile His Thr Trp
            100                 105                 110

Gln Arg Ile Gly Glu Val Thr Arg Met Ala Phe Arg Glu Met Trp Ala
        115                 120                 125

Gly Arg Pro Gly Pro Val Gln Ile Asp Val Pro Ser Pro Val Met Tyr
    130                 135                 140

Asp Met Thr Asp Glu Ser Arg Ala Gly Leu Leu Asp Pro Ile Ala Tyr
145                 150                 155                 160

Arg Ala Pro Pro Pro Ser Ala Gly Gly Ser Gln Ile Asn Ala Ala Ala
                165                 170                 175

Gln Leu Leu Ala Ala Ala Thr Arg Pro Leu Ile Met Val Gly Ser Gly
            180                 185                 190

Val Asp Arg Ala Gly Ala Gly Glu Ala Val Leu Arg Leu Ala Asp Lys
        195                 200                 205

Leu Gly Cys Gly Val Ile Ala Ser Leu Ala Gly Arg Ser Ala Val Pro
    210                 215                 220

Gln Asp His Pro Leu His Leu His Ala Tyr Gly Ala Gly Ala Asp Gln
225                 230                 235                 240

Ala Arg Arg Glu Ala Asp Val Ile Leu Ala Leu Gly Thr Arg Leu Gly
                245                 250                 255

Asn Ile Asp Thr Pro Phe Asp Arg Tyr Trp Gly Ser Ser Glu Gly His
            260                 265                 270

Lys Leu Ile Gln Val Asp Ile Asp Pro Arg Asn Leu Gly Ala Ser Arg
        275                 280                 285

Pro Leu Thr Leu Gly Ile Val Ser Asp Ala Gly Ser Leu Val Glu Gly
    290                 295                 300

Leu Leu Glu Ala Leu Glu Asn Ala Pro Thr Arg Ser Gly Ala Asp Val
305                 310                 315                 320

Asp Leu Thr Arg Tyr Arg Gln Met Asp Ala Glu Trp Arg Arg Ser Glu
                325                 330                 335

Phe Ala His Ile Glu Ala His Gly Gly Pro Ser Pro His Pro Ala Glu
            340                 345                 350

Val Met Gln Thr Val Gly Glu Val Phe Gly Pro Asp Ala Val Tyr Val
        355                 360                 365
```

-continued

```
Ala Asp Gly Gly Phe Thr Ser Leu Trp Ala His Phe Met Leu Pro Ser
    370                 375                 380

Thr Arg Pro Arg Ser Tyr Leu Asn Ile Leu Glu Met Gly Met Leu Gly
385                 390                 395                 400

Thr Gly Ile Pro Ser Ala Ile Gly Ala Gly Leu Gly Ser Pro Asp Arg
                405                 410                 415

Gln Ile Val Cys Val Thr Gly Asp Gly Ala Ala Gly Phe His Cys Met
            420                 425                 430

Glu Leu Gln Ser Ala Val Arg Glu Asp Val Lys Val Thr Val Val Val
        435                 440                 445

Leu Ala Glu Gly Ser Trp Ser Met Glu Val Pro Asn Glu Gln Ala Arg
    450                 455                 460

Tyr Gly Arg Thr Phe Gly Thr Glu Met Gly Pro Val Leu Trp Glu Arg
465                 470                 475                 480

Leu Ala Glu Ser Leu Gly Cys Phe Gly Phe Lys Ala Glu Thr Ala Pro
                485                 490                 495

Asp Leu Arg Pro Ala Leu Ser Ala Ala Arg Asp Ala Leu Gly Pro Ala
            500                 505                 510

Leu Val Arg Val Arg Thr Asp Arg Ala Ala Asn Leu Ala Phe Pro Pro
        515                 520                 525

Ser Ile Ala Met Arg Phe His Glu Gly Tyr Gln Gly Leu Thr Gly
    530                 535                 540


<210> SEQ ID NO 16
<211> LENGTH: 2865
<212> TYPE: DNA
<213> ORGANISM: Bacterium 2412.1
<220> FEATURE:
<223> OTHER INFORMATION: fccH Vitamin B12 Receptor
<221> NAME/KEY: CDS
<222> LOCATION: (1)..(2862)

<400> SEQUENCE: 16

atg ccg tcc ccc cct cgc cgt cac aaa gag agg gag gga tta gcc atg       48
Met Pro Ser Pro Pro Arg Arg His Lys Glu Arg Glu Gly Leu Ala Met
  1               5                  10                  15

agc caa gca gca acc aat cag aag agc act ttc cgc ctt agc ctg ctg       96
Ser Gln Ala Ala Thr Asn Gln Lys Ser Thr Phe Arg Leu Ser Leu Leu
             20                  25                  30

ggc gca gcg gcg acg tcc gtg ctt cta gcc cca agc ctc ggc cgg gcg      144
Gly Ala Ala Ala Thr Ser Val Leu Leu Ala Pro Ser Leu Gly Arg Ala
         35                  40                  45

cag caa gca cct gtc gaa aac cct cgg ccc agg acg cca gga agt cag      192
Gln Gln Ala Pro Val Glu Asn Pro Arg Pro Arg Thr Pro Gly Ser Gln
     50                  55                  60

cga aat cgt cgt cac ggg cag ccg cct cca gag cgg att cag cgc acc      240
Arg Asn Arg Arg His Gly Gln Pro Pro Pro Glu Arg Ile Gln Arg Thr
 65                  70                  75                  80

gac tcc cgt gac cgc ggc gtc tgc gat cag ctc aag gcg gcg gct cca      288
Asp Ser Arg Asp Arg Gly Val Cys Asp Gln Leu Lys Ala Ala Ala Pro
                 85                  90                  95

acc aac atc gcc gat ggc ctc aac caa ctt ccg gtc ttc aat aat agt      336
Thr Asn Ile Ala Asp Gly Leu Asn Gln Leu Pro Val Phe Asn Asn Ser
            100                 105                 110

ctg aaa acg tcg aac ccc ggc acg acg ccg ggc acc ggc aac agc ggc      384
Leu Lys Thr Ser Asn Pro Gly Thr Thr Pro Gly Thr Gly Asn Ser Gly
        115                 120                 125

cag aat ctc ctg agc ctg cgc ggc ctg ggc gcg aac cga aac ctc gtt      432
```

-continued

```
Gln Asn Leu Leu Ser Leu Arg Gly Leu Gly Ala Asn Arg Asn Leu Val
    130                 135                 140

ctg ctc aac ggc aac cgc ttc gtc gcc acc aac tac acc gga tcg gtg      480
Leu Leu Asn Gly Asn Arg Phe Val Ala Thr Asn Tyr Thr Gly Ser Val
145                 150                 155                 160

gac gtc aat gtg ttg ccc cag gct ctc gtc aag cgg gtc gac gtg gtg      528
Asp Val Asn Val Leu Pro Gln Ala Leu Val Lys Arg Val Asp Val Val
                165                 170                 175

acc ggc ggc gct tcg gcc gcc tac gga tcc gat gcc gta tcc ggc gta      576
Thr Gly Gly Ala Ser Ala Ala Tyr Gly Ser Asp Ala Val Ser Gly Val
            180                 185                 190

atc aac ttc gtc ctc gac gag gat ttc gag ggc cta aag gcg aac gtc      624
Ile Asn Phe Val Leu Asp Glu Asp Phe Glu Gly Leu Lys Ala Asn Val
        195                 200                 205

cag acc ggc gtc tcg agc cgc aac gat ctg gcc tcg gtg ggc gga tcg      672
Gln Thr Gly Val Ser Ser Arg Asn Asp Leu Ala Ser Val Gly Gly Ser
    210                 215                 220

ctg gcg gcc ggc aag tcg ttt gcc caa ggg cgc gca cat ctc ctt gcc      720
Leu Ala Ala Gly Lys Ser Phe Ala Gln Gly Arg Ala His Leu Leu Ala
225                 230                 235                 240

gcg gtc gaa tac tat cac gag gac ggc att cgc gcc gat cag gcc acc      768
Ala Val Glu Tyr Tyr His Glu Asp Gly Ile Arg Ala Asp Gln Ala Thr
                245                 250                 255

gat cgg gcg tgg tat gat cgc gcg gcg ggg caa tat ccc gtg ccc ggc      816
Asp Arg Ala Trp Tyr Asp Arg Ala Ala Gly Gln Tyr Pro Val Pro Gly
            260                 265                 270

gcc ccg acg ggc gtc acg gtg gtt ccc gac atc cga agc tcg cgc ggc      864
Ala Pro Thr Gly Val Thr Val Val Pro Asp Ile Arg Ser Ser Arg Gly
        275                 280                 285

gcc tac ggc ggc ctg atc aca tcg ggt ccg ctg aag ggc gtc acc ttt      912
Ala Tyr Gly Gly Leu Ile Thr Ser Gly Pro Leu Lys Gly Val Thr Phe
    290                 295                 300

ctt ccc ggc ggt acg ctt gcg acc ttt aac tac gga agc ttt acc agc      960
Leu Pro Gly Gly Thr Leu Ala Thr Phe Asn Tyr Gly Ser Phe Thr Ser
305                 310                 315                 320

agt tcc ttc cag agc ggc ggc gac ggt ccg cgc gtc aat ctc ggc ttc     1008
Ser Ser Phe Gln Ser Gly Gly Asp Gly Pro Arg Val Asn Leu Gly Phe
                325                 330                 335

gct ccg gac cag cgg cgc tac aat ggc ttc ctc cgc ggc gag ttc gag     1056
Ala Pro Asp Gln Arg Arg Tyr Asn Gly Phe Leu Arg Gly Glu Phe Glu
            340                 345                 350

gcc tca gaa cgc gtc aag ctc tat gcg gaa ggc acc tat gcc tat agc     1104
Ala Ser Glu Arg Val Lys Leu Tyr Ala Glu Gly Thr Tyr Ala Tyr Ser
        355                 360                 365

cac acc aac ctc ggc gcc ttc gtc aac cag ttt gtc ggc agc gcg aac     1152
His Thr Asn Leu Gly Ala Phe Val Asn Gln Phe Val Gly Ser Ala Asn
    370                 375                 380

gcc ttc acg atc ttc cgc gac aac gcg ttc ctc ccg acc gca ctc ggc     1200
Ala Phe Thr Ile Phe Arg Asp Asn Ala Phe Leu Pro Thr Ala Leu Gly
385                 390                 395                 400

gca ctg atg gac acc aac cgg ctg acg tcg gtt tcc gtc ggc cgg ttc     1248
Ala Leu Met Asp Thr Asn Arg Leu Thr Ser Val Ser Val Gly Arg Phe
                405                 410                 415

gcc ggc gag ttc ccg ctg gtc gag atc gag tcc tac gcc aag gtg cgt     1296
Ala Gly Glu Phe Pro Leu Val Glu Ile Glu Ser Tyr Ala Lys Val Arg
            420                 425                 430

cgc gga gct gcc ggc ttc cgg gcg gac ctc aac gac acc tgg aag ctc     1344
Arg Gly Ala Ala Gly Phe Arg Ala Asp Leu Asn Asp Thr Trp Lys Leu
        435                 440                 445
```

-continued

```
gac ggt tcg atc tcc tac ggc cgc acg aac ctg gag ctt cgc gaa aac      1392
Asp Gly Ser Ile Ser Tyr Gly Arg Thr Asn Leu Glu Leu Arg Glu Asn
    450                 455                 460

aac ctg tcg atc aac cgc aat ctc tat gca gcg gtc gac gcc gtg aag      1440
Asn Leu Ser Ile Asn Arg Asn Leu Tyr Ala Ala Val Asp Ala Val Lys
465                 470                 475                 480

gac ccg acg gga aag atc gtc tgc cgt tcg acc ctt tcg ggt ctc gac      1488
Asp Pro Thr Gly Lys Ile Val Cys Arg Ser Thr Leu Ser Gly Leu Asp
                485                 490                 495

gcg ggc tgc gtg ccg ctc aac att ttc ggc gcc ggc gcg cca agt gcc      1536
Ala Gly Cys Val Pro Leu Asn Ile Phe Gly Ala Gly Ala Pro Ser Ala
            500                 505                 510

gcc gcg atc gac tat gtc ctc gac gac ggg gtg gcg aac ctg aaa ctg      1584
Ala Ala Ile Asp Tyr Val Leu Asp Asp Gly Val Ala Asn Leu Lys Leu
        515                 520                 525

gaa cag gtc gtc gcg ggc ctg aac ctc gtc ggc gac ctt ggc cag gcg      1632
Glu Gln Val Val Ala Gly Leu Asn Leu Val Gly Asp Leu Gly Gln Ala
    530                 535                 540

ttt tcg ctg ggc gcc ggg ccg atc tcg atc gcc gcg ggc ggc gaa tat      1680
Phe Ser Leu Gly Ala Gly Pro Ile Ser Ile Ala Ala Gly Gly Glu Tyr
545                 550                 555                 560

cgt gag gag aaa gcc aac cag acc acc gac gcc atc tcg cag gcg atc      1728
Arg Glu Glu Lys Ala Asn Gln Thr Thr Asp Ala Ile Ser Gln Ala Ile
                565                 570                 575

acg tcg acc gcc gga ctg cgt gga gcg ccg gcc tct cag agc aac cgg      1776
Thr Ser Thr Ala Gly Leu Arg Gly Ala Pro Ala Ser Gln Ser Asn Arg
            580                 585                 590

cct ggt ggt ttc aac ctc tac aac cct ctt ccc ttc agc ggg agc tac      1824
Pro Gly Gly Phe Asn Leu Tyr Asn Pro Leu Pro Phe Ser Gly Ser Tyr
        595                 600                 605

aac atc aag gag gct tat ctt gag gtc ggg gtt ccg gtg ctc aag gac      1872
Asn Ile Lys Glu Ala Tyr Leu Glu Val Gly Val Pro Val Leu Lys Asp
    610                 615                 620

agc gcg ctt ggt cga gcg ctc aac ctc aac ggc gcg gtc cgg tat gcc      1920
Ser Ala Leu Gly Arg Ala Leu Asn Leu Asn Gly Ala Val Arg Tyr Ala
625                 630                 635                 640

gac tat agc gtc tcg ggc ggc gtc acg acc tgg aag gtc ggc ggc gac      1968
Asp Tyr Ser Val Ser Gly Gly Val Thr Thr Trp Lys Val Gly Gly Asp
                645                 650                 655

tac gag ccc gtc gat gga ctg cgg ttt cgc ctg act cgc tcg cgc gac      2016
Tyr Glu Pro Val Asp Gly Leu Arg Phe Arg Leu Thr Arg Ser Arg Asp
            660                 665                 670

atc cgc ggc gcc agc ctg gtg gaa ctc tac gac ccc ggc cgt cag gct      2064
Ile Arg Gly Ala Ser Leu Val Glu Leu Tyr Asp Pro Gly Arg Gln Ala
        675                 680                 685

acc ctg aac tct gtc tat cag ggc cag acg ttg cag acc cgc ttc ttc      2112
Thr Leu Asn Ser Val Tyr Gln Gly Gln Thr Leu Gln Thr Arg Phe Phe
    690                 695                 700

acc gcc ggc aac ccg gat ctt cgc ccc gag cgc gcc gat acc ctg acc      2160
Thr Ala Gly Asn Pro Asp Leu Arg Pro Glu Arg Ala Asp Thr Leu Thr
705                 710                 715                 720

ttc ggc gtc gtg ttg cgg ccg gcc ttc gcc ccg ggg ctt cag ctt tcg      2208
Phe Gly Val Val Leu Arg Pro Ala Phe Ala Pro Gly Leu Gln Leu Ser
                725                 730                 735

gcg gac cgc tat atc atc gat ctc aaa gac gcc atc gac tac ctc ctg      2256
Ala Asp Arg Tyr Ile Ile Asp Leu Lys Asp Ala Ile Asp Tyr Leu Leu
            740                 745                 750

ccc cag cag gag atc gac ctc tgc gcc gcg ggc aac cag tcc atg tgc      2304
Pro Gln Gln Glu Ile Asp Leu Cys Ala Ala Gly Asn Gln Ser Met Cys
        755                 760                 765
```

-continued

```
gcc ttg atc acc cgg aat gcg gac aac acg ctg acc gtc atc ggc ccc     2352
Ala Leu Ile Thr Arg Asn Ala Asp Asn Thr Leu Thr Val Ile Gly Pro
    770                 775                 780

aac ctg aac ctt gcg gtg cag aag gcg gcg ggt gtc gat ttg gag gcg     2400
Asn Leu Asn Leu Ala Val Gln Lys Ala Ala Gly Val Asp Leu Glu Ala
785                 790                 795                 800

tcc tac gtg cgc aac gtc gcg ggc gga tct ctg aac ctg cgg gcc ttg     2448
Ser Tyr Val Arg Asn Val Ala Gly Gly Ser Leu Asn Leu Arg Ala Leu
                805                 810                 815

gcc aac cac cgc acg gcc gca tcc gtc acc gcc ctg ggc tcg gcg ccc     2496
Ala Asn His Arg Thr Ala Ala Ser Val Thr Ala Leu Gly Ser Ala Pro
            820                 825                 830

cta caa tcg ctc ggc gaa ccc acc gcc ccc aaa tgg ctg ctc aat ctg     2544
Leu Gln Ser Leu Gly Glu Pro Thr Ala Pro Lys Trp Leu Leu Asn Leu
        835                 840                 845

cag gcg cgt tac gag cgc gcc gca tgg tcg ctg ttc ctg caa gag cgc     2592
Gln Ala Arg Tyr Glu Arg Ala Ala Trp Ser Leu Phe Leu Gln Glu Arg
    850                 855                 860

ttc atc tct cgc tcg gtc ttt gac gct gaa aac gtc gaa ggt gtc gac     2640
Phe Ile Ser Arg Ser Val Phe Asp Ala Glu Asn Val Glu Gly Val Asp
865                 870                 875                 880

acc aac ctg aac cac acc ggc gca gtc tgg tac act gac gcc acg gtg     2688
Thr Asn Leu Asn His Thr Gly Ala Val Trp Tyr Thr Asp Ala Thr Val
                885                 890                 895

acc tac agc ttc gat tca ttc ggg cat aag cag cag gtt ttt gct tcg     2736
Thr Tyr Ser Phe Asp Ser Phe Gly His Lys Gln Gln Val Phe Ala Ser
            900                 905                 910

gta aac aac ctc ttc gac cgt gat cca ccg gtg gcg acg gtc aat ccg     2784
Val Asn Asn Leu Phe Asp Arg Asp Pro Pro Val Ala Thr Val Asn Pro
        915                 920                 925

tcc agc ttc tcg gtc ccg acg agc gca gcc tac gat ccg cgc ggc agg     2832
Ser Ser Phe Ser Val Pro Thr Ser Ala Ala Tyr Asp Pro Arg Gly Arg
    930                 935                 940

tat ttc aac gtc ggg ctc cgc ttc cgc tac tga                         2865
Tyr Phe Asn Val Gly Leu Arg Phe Arg Tyr
945                 950


<210> SEQ ID NO 17
<211> LENGTH: 954
<212> TYPE: PRT
<213> ORGANISM: Bacterium 2412.1

<400> SEQUENCE: 17

Met Pro Ser Pro Pro Arg Arg His Lys Glu Arg Glu Gly Leu Ala Met
  1               5                  10                  15

Ser Gln Ala Ala Thr Asn Gln Lys Ser Thr Phe Arg Leu Ser Leu Leu
             20                  25                  30

Gly Ala Ala Ala Thr Ser Val Leu Leu Ala Pro Ser Leu Gly Arg Ala
         35                  40                  45

Gln Gln Ala Pro Val Glu Asn Pro Arg Pro Arg Thr Pro Gly Ser Gln
     50                  55                  60

Arg Asn Arg Arg His Gly Gln Pro Pro Pro Glu Arg Ile Gln Arg Thr
 65                  70                  75                  80

Asp Ser Arg Asp Arg Gly Val Cys Asp Gln Leu Lys Ala Ala Ala Pro
                 85                  90                  95

Thr Asn Ile Ala Asp Gly Leu Asn Gln Leu Pro Val Phe Asn Asn Ser
            100                 105                 110

Leu Lys Thr Ser Asn Pro Gly Thr Thr Pro Gly Thr Gly Asn Ser Gly
```

-continued

```
        115                 120                 125

Gln Asn Leu Leu Ser Leu Arg Gly Leu Gly Ala Asn Arg Asn Leu Val
    130                 135                 140

Leu Leu Asn Gly Asn Arg Phe Val Ala Thr Asn Tyr Thr Gly Ser Val
145                 150                 155                 160

Asp Val Asn Val Leu Pro Gln Ala Leu Val Lys Arg Val Asp Val Val
                165                 170                 175

Thr Gly Gly Ala Ser Ala Ala Tyr Gly Ser Asp Ala Val Ser Gly Val
            180                 185                 190

Ile Asn Phe Val Leu Asp Glu Asp Phe Glu Gly Leu Lys Ala Asn Val
        195                 200                 205

Gln Thr Gly Val Ser Ser Arg Asn Asp Leu Ala Ser Val Gly Gly Ser
    210                 215                 220

Leu Ala Ala Gly Lys Ser Phe Ala Gln Gly Arg Ala His Leu Leu Ala
225                 230                 235                 240

Ala Val Glu Tyr Tyr His Glu Asp Gly Ile Arg Ala Asp Gln Ala Thr
                245                 250                 255

Asp Arg Ala Trp Tyr Asp Arg Ala Ala Gly Gln Tyr Pro Val Pro Gly
            260                 265                 270

Ala Pro Thr Gly Val Thr Val Val Pro Asp Ile Arg Ser Ser Arg Gly
        275                 280                 285

Ala Tyr Gly Gly Leu Ile Thr Ser Gly Pro Leu Lys Gly Val Thr Phe
    290                 295                 300

Leu Pro Gly Gly Thr Leu Ala Thr Phe Asn Tyr Gly Ser Phe Thr Ser
305                 310                 315                 320

Ser Ser Phe Gln Ser Gly Gly Asp Gly Pro Arg Val Asn Leu Gly Phe
                325                 330                 335

Ala Pro Asp Gln Arg Arg Tyr Asn Gly Phe Leu Arg Gly Glu Phe Glu
            340                 345                 350

Ala Ser Glu Arg Val Lys Leu Tyr Ala Glu Gly Thr Tyr Ala Tyr Ser
        355                 360                 365

His Thr Asn Leu Gly Ala Phe Val Asn Gln Phe Val Gly Ser Ala Asn
    370                 375                 380

Ala Phe Thr Ile Phe Arg Asp Asn Ala Phe Leu Pro Thr Ala Leu Gly
385                 390                 395                 400

Ala Leu Met Asp Thr Asn Arg Leu Thr Ser Val Ser Val Gly Arg Phe
                405                 410                 415

Ala Gly Glu Phe Pro Leu Val Glu Ile Glu Ser Tyr Ala Lys Val Arg
            420                 425                 430

Arg Gly Ala Ala Gly Phe Arg Ala Asp Leu Asn Asp Thr Trp Lys Leu
        435                 440                 445

Asp Gly Ser Ile Ser Tyr Gly Arg Thr Asn Leu Glu Leu Arg Glu Asn
    450                 455                 460

Asn Leu Ser Ile Asn Arg Asn Leu Tyr Ala Ala Val Asp Ala Val Lys
465                 470                 475                 480

Asp Pro Thr Gly Lys Ile Val Cys Arg Ser Thr Leu Ser Gly Leu Asp
                485                 490                 495

Ala Gly Cys Val Pro Leu Asn Ile Phe Gly Ala Gly Ala Pro Ser Ala
            500                 505                 510

Ala Ala Ile Asp Tyr Val Leu Asp Asp Gly Val Ala Asn Leu Lys Leu
        515                 520                 525

Glu Gln Val Val Ala Gly Leu Asn Leu Val Gly Asp Leu Gly Gln Ala
    530                 535                 540
```

-continued

```
Phe Ser Leu Gly Ala Gly Pro Ile Ser Ile Ala Ala Gly Gly Glu Tyr
545                 550                 555                 560

Arg Glu Glu Lys Ala Asn Gln Thr Thr Asp Ala Ile Ser Gln Ala Ile
                565                 570                 575

Thr Ser Thr Ala Gly Leu Arg Gly Ala Pro Ala Ser Gln Ser Asn Arg
            580                 585                 590

Pro Gly Gly Phe Asn Leu Tyr Asn Pro Leu Pro Phe Ser Gly Ser Tyr
        595                 600                 605

Asn Ile Lys Glu Ala Tyr Leu Glu Val Gly Val Pro Val Leu Lys Asp
    610                 615                 620

Ser Ala Leu Gly Arg Ala Leu Asn Leu Asn Gly Ala Val Arg Tyr Ala
625                 630                 635                 640

Asp Tyr Ser Val Ser Gly Gly Val Thr Thr Trp Lys Val Gly Gly Asp
                645                 650                 655

Tyr Glu Pro Val Asp Gly Leu Arg Phe Arg Leu Thr Arg Ser Arg Asp
            660                 665                 670

Ile Arg Gly Ala Ser Leu Val Glu Leu Tyr Asp Pro Gly Arg Gln Ala
        675                 680                 685

Thr Leu Asn Ser Val Tyr Gln Gly Gln Thr Leu Gln Thr Arg Phe Phe
    690                 695                 700

Thr Ala Gly Asn Pro Asp Leu Arg Pro Glu Arg Ala Asp Thr Leu Thr
705                 710                 715                 720

Phe Gly Val Val Leu Arg Pro Ala Phe Ala Pro Gly Leu Gln Leu Ser
                725                 730                 735

Ala Asp Arg Tyr Ile Ile Asp Leu Lys Asp Ala Ile Asp Tyr Leu Leu
            740                 745                 750

Pro Gln Gln Glu Ile Asp Leu Cys Ala Ala Gly Asn Gln Ser Met Cys
        755                 760                 765

Ala Leu Ile Thr Arg Asn Ala Asp Asn Thr Leu Thr Val Ile Gly Pro
    770                 775                 780

Asn Leu Asn Leu Ala Val Gln Lys Ala Ala Gly Val Asp Leu Glu Ala
785                 790                 795                 800

Ser Tyr Val Arg Asn Val Ala Gly Gly Ser Leu Asn Leu Arg Ala Leu
                805                 810                 815

Ala Asn His Arg Thr Ala Ala Ser Val Thr Ala Leu Gly Ser Ala Pro
            820                 825                 830

Leu Gln Ser Leu Gly Glu Pro Thr Ala Pro Lys Trp Leu Leu Asn Leu
        835                 840                 845

Gln Ala Arg Tyr Glu Arg Ala Ala Trp Ser Leu Phe Leu Gln Glu Arg
    850                 855                 860

Phe Ile Ser Arg Ser Val Phe Asp Ala Glu Asn Val Glu Gly Val Asp
865                 870                 875                 880

Thr Asn Leu Asn His Thr Gly Ala Val Trp Tyr Thr Asp Ala Thr Val
                885                 890                 895

Thr Tyr Ser Phe Asp Ser Phe Gly His Lys Gln Gln Val Phe Ala Ser
            900                 905                 910

Val Asn Asn Leu Phe Asp Arg Asp Pro Pro Val Ala Thr Val Asn Pro
        915                 920                 925

Ser Ser Phe Ser Val Pro Thr Ser Ala Ala Tyr Asp Pro Arg Gly Arg
    930                 935                 940

Tyr Phe Asn Val Gly Leu Arg Phe Arg Tyr
945                 950
```

-continued

```
<210> SEQ ID NO 18
<211> LENGTH: 1302
<212> TYPE: DNA
<213> ORGANISM: Bacterium 2412.1
<220> FEATURE:
<223> OTHER INFORMATION: fccI Permease
<221> NAME/KEY: CDS
<222> LOCATION: (1)..(1299)

<400> SEQUENCE: 18

atg cgt gtt ttc gta aat cgc gga cga tgt cag aat tgc tct caa act       48
Met Arg Val Phe Val Asn Arg Gly Arg Cys Gln Asn Cys Ser Gln Thr
  1               5                  10                  15

att atc gat att tgc tgg gtg tgt gga gcg cag ccg ctc ccc cac aga       96
Ile Ile Asp Ile Cys Trp Val Cys Gly Ala Gln Pro Leu Pro His Arg
             20                  25                  30

tgc gaa ttc cct tca cct tct cga cga cag ttg gag cct atg tcc ctg      144
Cys Glu Phe Pro Ser Pro Ser Arg Arg Gln Leu Glu Pro Met Ser Leu
         35                  40                  45

acc ctg ccc cgg aat acc gga cct cgc cat cac cag gcc gtg tcc gtc      192
Thr Leu Pro Arg Asn Thr Gly Pro Arg His His Gln Ala Val Ser Val
     50                  55                  60

gta tcg gcc act atg ctg atc ggc acg gcc tcg atg ctg gtg atg ggc      240
Val Ser Ala Thr Met Leu Ile Gly Thr Ala Ser Met Leu Val Met Gly
 65                  70                  75                  80

gtc gaa ccc atc ctg ctc ggg ggt ctc gcc aac gcc ggg cgg atc agc      288
Val Glu Pro Ile Leu Leu Gly Gly Leu Ala Asn Ala Gly Arg Ile Ser
                 85                  90                  95

gag gcg ggc gta ggt cag gcc gcc atg atc gaa gtc ttc gcc ctg gcc      336
Glu Ala Gly Val Gly Gln Ala Ala Met Ile Glu Val Phe Ala Leu Ala
            100                 105                 110

gca ggc tcg acg gcg ggt ccg ttc ctg atg aac ctc ggc cac atg cgc      384
Ala Gly Ser Thr Ala Gly Pro Phe Leu Met Asn Leu Gly His Met Arg
        115                 120                 125

gcc aag gtg gcc gct gcc tcc ctg ctc ctt gcg atc atc aac ctc gcc      432
Ala Lys Val Ala Ala Ala Ser Leu Leu Leu Ala Ile Ile Asn Leu Ala
    130                 135                 140

atc tac tgg gcc gca tcc ccg gcc acg atc ctg gtc caa cgc ggc gcg      480
Ile Tyr Trp Ala Ala Ser Pro Ala Thr Ile Leu Val Gln Arg Gly Ala
145                 150                 155                 160

gcc ggg ttg ctg gaa ggg cta ttg ctg ggc gcg gcc ggc gcc atc ctt      528
Ala Gly Leu Leu Glu Gly Leu Leu Leu Gly Ala Ala Gly Ala Ile Leu
                165                 170                 175

acc cac aac gac cgg cct gag cgc atg agc ggg ctg ctg ctc ggt ctt      576
Thr His Asn Asp Arg Pro Glu Arg Met Ser Gly Leu Leu Leu Gly Leu
            180                 185                 190

tcc acg atc ccc cag gtg atc gcg gcc tat ttg ctg ccg atc tgg gtg      624
Ser Thr Ile Pro Gln Val Ile Ala Ala Tyr Leu Leu Pro Ile Trp Val
        195                 200                 205

atc ccg cgg ttt ggc gtg gat gcc ggg ttc gcg gtc ttg gcg ggc gtt      672
Ile Pro Arg Phe Gly Val Asp Ala Gly Phe Ala Val Leu Ala Gly Val
    210                 215                 220

gcg atg gcc tcc tgc ctc gtt gcg ccg gcg atc gtc gac cac gtg cct      720
Ala Met Ala Ser Cys Leu Val Ala Pro Ala Ile Val Asp His Val Pro
225                 230                 235                 240

gct cct acg gga tcg cac cat ggt cgc gta gtc gtc tct ccg gcc ctg      768
Ala Pro Thr Gly Ser His His Gly Arg Val Val Val Ser Pro Ala Leu
                245                 250                 255

atg gtc gtg gcg ctc gcg gcg ttt ctt caa aac gcc ggc atc ggg gcg      816
Met Val Val Ala Leu Ala Ala Phe Leu Gln Asn Ala Gly Ile Gly Ala
            260                 265                 270
```

-continued

```
gca tgg aac tac ctg gag cgc ctg gcc gcg caa cac cat ttc gcc ccg      864
Ala Trp Asn Tyr Leu Glu Arg Leu Ala Ala Gln His His Phe Ala Pro
        275                 280                 285

gcc acg gtc ggc gcc gcg atc gcg ggc agc ctg gcc ttc cag gtg gcg      912
Ala Thr Val Gly Ala Ala Ile Ala Gly Ser Leu Ala Phe Gln Val Ala
    290                 295                 300

ggt gct ctt gca gca tcc tgg ctc ggt gcg cgc gtg cac gcc cgt acg      960
Gly Ala Leu Ala Ala Ser Trp Leu Gly Ala Arg Val His Ala Arg Thr
305                 310                 315                 320

gtt ctg gcc gcc ggc gca gtg ctg cag gcc ggt ctt gtc atc ggc ctg     1008
Val Leu Ala Ala Gly Ala Val Leu Gln Ala Gly Leu Val Ile Gly Leu
                325                 330                 335

ctt cac gcc ggc acg ccc gtc gcg ctc atc gca agc gct tgt ggc ttt     1056
Leu His Ala Gly Thr Pro Val Ala Leu Ile Ala Ser Ala Cys Gly Phe
            340                 345                 350

ggc ctg ttc tgg ctg gcg ctg cag ccg ttt ctg gtg gcg gac gtg atc     1104
Gly Leu Phe Trp Leu Ala Leu Gln Pro Phe Leu Val Ala Asp Val Ile
        355                 360                 365

gcc ttg gag ccc agc agg acc gcc gcc gta ctg ctc gcc cct ctc gcg     1152
Ala Leu Glu Pro Ser Arg Thr Ala Ala Val Leu Leu Ala Pro Leu Ala
    370                 375                 380

ttg gtg ggc ttc agc gcc ggt ccg ttg gcg gcc tcg ttc gtc att gac     1200
Leu Val Gly Phe Ser Ala Gly Pro Leu Ala Ala Ser Phe Val Ile Asp
385                 390                 395                 400

gat aat cgg gtg gga ggc gca ttc cag gtt tcg gcc ggc tcc tcg ttg     1248
Asp Asn Arg Val Gly Gly Ala Phe Gln Val Ser Ala Gly Ser Ser Leu
                405                 410                 415

cgg cgg cgg cgc tct acg tcg tgg ccg gcc cct ggc ggc ggg cgg cta     1296
Arg Arg Arg Arg Ser Thr Ser Trp Pro Ala Pro Gly Gly Gly Arg Leu
            420                 425                 430

ctt taa                                                              1302
Leu


<210> SEQ ID NO 19
<211> LENGTH: 433
<212> TYPE: PRT
<213> ORGANISM: Bacterium 2412.1

<400> SEQUENCE: 19

Met Arg Val Phe Val Asn Arg Gly Arg Cys Gln Asn Cys Ser Gln Thr
  1               5                  10                  15

Ile Ile Asp Ile Cys Trp Val Cys Gly Ala Gln Pro Leu Pro His Arg
             20                  25                  30

Cys Glu Phe Pro Ser Pro Ser Arg Arg Gln Leu Glu Pro Met Ser Leu
         35                  40                  45

Thr Leu Pro Arg Asn Thr Gly Pro Arg His His Gln Ala Val Ser Val
     50                  55                  60

Val Ser Ala Thr Met Leu Ile Gly Thr Ala Ser Met Leu Val Met Gly
 65                  70                  75                  80

Val Glu Pro Ile Leu Leu Gly Gly Leu Ala Asn Ala Gly Arg Ile Ser
                 85                  90                  95

Glu Ala Gly Val Gly Gln Ala Ala Met Ile Glu Val Phe Ala Leu Ala
            100                 105                 110

Ala Gly Ser Thr Ala Gly Pro Phe Leu Met Asn Leu Gly His Met Arg
        115                 120                 125

Ala Lys Val Ala Ala Ala Ser Leu Leu Leu Ala Ile Ile Asn Leu Ala
    130                 135                 140
```

-continued

```
Ile Tyr Trp Ala Ala Ser Pro Ala Thr Ile Leu Val Gln Arg Gly Ala
145                 150                 155                 160

Ala Gly Leu Leu Glu Gly Leu Leu Leu Gly Ala Ala Gly Ala Ile Leu
                165                 170                 175

Thr His Asn Asp Arg Pro Glu Arg Met Ser Gly Leu Leu Leu Gly Leu
            180                 185                 190

Ser Thr Ile Pro Gln Val Ile Ala Ala Tyr Leu Leu Pro Ile Trp Val
        195                 200                 205

Ile Pro Arg Phe Gly Val Asp Ala Gly Phe Ala Val Leu Ala Gly Val
    210                 215                 220

Ala Met Ala Ser Cys Leu Val Ala Pro Ala Ile Val Asp His Val Pro
225                 230                 235                 240

Ala Pro Thr Gly Ser His His Gly Arg Val Val Val Ser Pro Ala Leu
                245                 250                 255

Met Val Val Ala Leu Ala Ala Phe Leu Gln Asn Ala Gly Ile Gly Ala
            260                 265                 270

Ala Trp Asn Tyr Leu Glu Arg Leu Ala Ala Gln His His Phe Ala Pro
        275                 280                 285

Ala Thr Val Gly Ala Ala Ile Ala Gly Ser Leu Ala Phe Gln Val Ala
    290                 295                 300

Gly Ala Leu Ala Ala Ser Trp Leu Gly Ala Arg Val His Ala Arg Thr
305                 310                 315                 320

Val Leu Ala Ala Gly Ala Val Leu Gln Ala Gly Leu Val Ile Gly Leu
                325                 330                 335

Leu His Ala Gly Thr Pro Val Ala Leu Ile Ala Ser Ala Cys Gly Phe
            340                 345                 350

Gly Leu Phe Trp Leu Ala Leu Gln Pro Phe Leu Val Ala Asp Val Ile
        355                 360                 365

Ala Leu Glu Pro Ser Arg Thr Ala Ala Val Leu Leu Ala Pro Leu Ala
    370                 375                 380

Leu Val Gly Phe Ser Ala Gly Pro Leu Ala Ala Ser Phe Val Ile Asp
385                 390                 395                 400

Asp Asn Arg Val Gly Gly Ala Phe Gln Val Ser Ala Gly Ser Ser Leu
                405                 410                 415

Arg Arg Arg Arg Ser Thr Ser Trp Pro Ala Pro Gly Gly Gly Arg Leu
            420                 425                 430

Leu


<210> SEQ ID NO 20
<211> LENGTH: 912
<212> TYPE: DNA
<213> ORGANISM: Bacterium 2412.1
<220> FEATURE:
<223> OTHER INFORMATION: fccJ Regulatory Protein
<221> NAME/KEY: CDS
<222> LOCATION: (1)..(909)

<400> SEQUENCE: 20

atg ttg aac tgc gat cta ttg gat ctg cgc gcc ttc gtc gcg gtc cac       48
Met Leu Asn Cys Asp Leu Leu Asp Leu Arg Ala Phe Val Ala Val His
  1               5                  10                  15

gaa acc cgc agc ttc atc cgc gcg gcg cat ctg ctc ggc ctt tcc cag       96
Glu Thr Arg Ser Phe Ile Arg Ala Ala His Leu Leu Gly Leu Ser Gln
            20                  25                  30

ccc gcg ctc agt cgc cgg atc caa cgc ttg gag gga ctg gtc ggc ggc      144
Pro Ala Leu Ser Arg Arg Ile Gln Arg Leu Glu Gly Leu Val Gly Gly
        35                  40                  45
```

-continued

```
gct ctc ttc gac cga acc agc cgg acc atg acc gag acc gcg ctt ggc      192
Ala Leu Phe Asp Arg Thr Ser Arg Thr Met Thr Glu Thr Ala Leu Gly
     50                  55                  60

aag gag ctg ctg ccg gtg gcc cgc cga acg ctt gag ttt ctg gac aat      240
Lys Glu Leu Leu Pro Val Ala Arg Arg Thr Leu Glu Phe Leu Asp Asn
 65                  70                  75                  80

tcg ctg ttc gcc tcg ccc aag ctg cgc gaa ccg cgc tgg acc gac atc      288
Ser Leu Phe Ala Ser Pro Lys Leu Arg Glu Pro Arg Trp Thr Asp Ile
                 85                  90                  95

agc att ttt tgc gtg cag acc gcc gcg ttc cgc gtt ctg ccg cgc gcg      336
Ser Ile Phe Cys Val Gln Thr Ala Ala Phe Arg Val Leu Pro Arg Ala
            100                 105                 110

gcc cgg cgc ttc atg gat gaa aat ccc cga ctg cgc ctg agg atc atc      384
Ala Arg Arg Phe Met Asp Glu Asn Pro Arg Leu Arg Leu Arg Ile Ile
        115                 120                 125

gat gtt ccg gct gtc gaa ggc gcg gaa ctg gtg gcg cga ggg gaa gcg      432
Asp Val Pro Ala Val Glu Gly Ala Glu Leu Val Ala Arg Gly Glu Ala
    130                 135                 140

gag ttc ggt atc agc atc gag agc ctg ctt ccg tcc ggc ctg cgt ttc      480
Glu Phe Gly Ile Ser Ile Glu Ser Leu Leu Pro Ser Gly Leu Arg Phe
145                 150                 155                 160

gag gct ctt cac gag gac ccg ttt ggc ttg gcg tgc cat cgg agc cat      528
Glu Ala Leu His Glu Asp Pro Phe Gly Leu Ala Cys His Arg Ser His
                165                 170                 175

cgc ctg gcg caa agc gac gtc atc gaa tgg tcc gcg ctc cgc ggc gaa      576
Arg Leu Ala Gln Ser Asp Val Ile Glu Trp Ser Ala Leu Arg Gly Glu
            180                 185                 190

aat ctt gtc gcc gtc cac cgg gcc agt cgc aac cgg acc ctg ctc gac      624
Asn Leu Val Ala Val His Arg Ala Ser Arg Asn Arg Thr Leu Leu Asp
        195                 200                 205

gcc gag ctc aag cag cat gcg atc tcc ctg gac tgg cgt tac gag gtc      672
Ala Glu Leu Lys Gln His Ala Ile Ser Leu Asp Trp Arg Tyr Glu Val
    210                 215                 220

ggt cac ttg acg acc gcg ctg ggg ctg atc gag tcc gag gtc ggc gtg      720
Gly His Leu Thr Thr Ala Leu Gly Leu Ile Glu Ser Glu Val Gly Val
225                 230                 235                 240

gcc gtc atg ccg cgg atg gtg atg ccc caa tca ggc cgc tca gaa ctg      768
Ala Val Met Pro Arg Met Val Met Pro Gln Ser Gly Arg Ser Glu Leu
                245                 250                 255

gtc tgg gtt ccc ttg gtc gcc ccg gtc gtg agg cgc acg atc ggc atc      816
Val Trp Val Pro Leu Val Ala Pro Val Val Arg Arg Thr Ile Gly Ile
            260                 265                 270

gtg cag cgc cgg gtg ggc gcg atg cat ccc gcc gcc gcc caa ctg ctc      864
Val Gln Arg Arg Val Gly Ala Met His Pro Ala Ala Ala Gln Leu Leu
        275                 280                 285

gag cgg ttg cgg gag gaa tgg ccg acc ggc gcg ccc gcg gac gag tag      912
Glu Arg Leu Arg Glu Glu Trp Pro Thr Gly Ala Pro Ala Asp Glu
    290                 295                 300


<210> SEQ ID NO 21
<211> LENGTH: 303
<212> TYPE: PRT
<213> ORGANISM: Bacterium 2412.1

<400> SEQUENCE: 21

Met Leu Asn Cys Asp Leu Leu Asp Leu Arg Ala Phe Val Ala Val His
  1               5                  10                  15

Glu Thr Arg Ser Phe Ile Arg Ala Ala His Leu Leu Gly Leu Ser Gln
             20                  25                  30
```

-continued

```
Pro Ala Leu Ser Arg Arg Ile Gln Arg Leu Glu Gly Leu Val Gly Gly
        35                  40                  45

Ala Leu Phe Asp Arg Thr Ser Arg Thr Met Thr Glu Thr Ala Leu Gly
    50                  55                  60

Lys Glu Leu Leu Pro Val Ala Arg Arg Thr Leu Glu Phe Leu Asp Asn
 65                 70                  75                  80

Ser Leu Phe Ala Ser Pro Lys Leu Arg Glu Pro Arg Trp Thr Asp Ile
                85                  90                  95

Ser Ile Phe Cys Val Gln Thr Ala Ala Phe Arg Val Leu Pro Arg Ala
            100                 105                 110

Ala Arg Arg Phe Met Asp Glu Asn Pro Arg Leu Arg Leu Arg Ile Ile
        115                 120                 125

Asp Val Pro Ala Val Glu Gly Ala Glu Leu Val Ala Arg Gly Glu Ala
    130                 135                 140

Glu Phe Gly Ile Ser Ile Glu Ser Leu Leu Pro Ser Gly Leu Arg Phe
145                 150                 155                 160

Glu Ala Leu His Glu Asp Pro Phe Gly Leu Ala Cys His Arg Ser His
                165                 170                 175

Arg Leu Ala Gln Ser Asp Val Ile Glu Trp Ser Ala Leu Arg Gly Glu
            180                 185                 190

Asn Leu Val Ala Val His Arg Ala Ser Arg Asn Arg Thr Leu Leu Asp
        195                 200                 205

Ala Glu Leu Lys Gln His Ala Ile Ser Leu Asp Trp Arg Tyr Glu Val
    210                 215                 220

Gly His Leu Thr Thr Ala Leu Gly Leu Ile Glu Ser Glu Val Gly Val
225                 230                 235                 240

Ala Val Met Pro Arg Met Val Met Pro Gln Ser Gly Arg Ser Glu Leu
                245                 250                 255

Val Trp Val Pro Leu Val Ala Pro Val Val Arg Arg Thr Ile Gly Ile
            260                 265                 270

Val Gln Arg Arg Val Gly Ala Met His Pro Ala Ala Ala Gln Leu Leu
        275                 280                 285

Glu Arg Leu Arg Glu Glu Trp Pro Thr Gly Ala Pro Ala Asp Glu
    290                 295                 300
```

<210> SEQ ID NO 22
<211> LENGTH: 1389
<212> TYPE: DNA
<213> ORGANISM: Bacterium 2412.1
<220> FEATURE:
<223> OTHER INFORMATION: fccK Fumarate Reductase/Aspartate oxidase
<221> NAME/KEY: CDS
<222> LOCATION: ()..(1389)

<400> SEQUENCE: 22

```
atg ggt gcg aag ttg aag tat gac gtg gtg gtg gtc ggg ggc ggc aat       48
Met Gly Ala Lys Leu Lys Tyr Asp Val Val Val Val Gly Gly Gly Asn
  1               5                  10                  15

gcg gcg atg acg gcg gcc gtc acc gcg cgg gaa gcc ggc gcg acg gtg       96
Ala Ala Met Thr Ala Ala Val Thr Ala Arg Glu Ala Gly Ala Thr Val
             20                  25                  30

ctg gtg ctt gag cat gcg ccc cgg tcg atg cgc ggc ggc aac agc cgc      144
Leu Val Leu Glu His Ala Pro Arg Ser Met Arg Gly Gly Asn Ser Arg
         35                  40                  45

cat acg cgc aac atg cgc acg atg cac gag gcg cca ctt gcg gtc ttg      192
His Thr Arg Asn Met Arg Thr Met His Glu Ala Pro Leu Ala Val Leu
     50                  55                  60
```

-continued

```
acc ggg caa tat tcc gaa gac gaa tac tgg aac gac ctg aag cgg gtc      240
Thr Gly Gln Tyr Ser Glu Asp Glu Tyr Trp Asn Asp Leu Lys Arg Val
 65                  70                  75                  80

acg ggc ggg gaa acc gac gag gcc ctg gcc cgt ctg gtg atc cgc agc      288
Thr Gly Gly Glu Thr Asp Glu Ala Leu Ala Arg Leu Val Ile Arg Ser
                 85                  90                  95

acg acg gac gcc atc ccc ttc atg ctc cgg tgc ggc gtg cgc ttc cag      336
Thr Thr Asp Ala Ile Pro Phe Met Leu Arg Cys Gly Val Arg Phe Gln
            100                 105                 110

cca tcg ctg tcg ggc acc ttg agc ctg tcg cgg acc aac gcg ttc ttc      384
Pro Ser Leu Ser Gly Thr Leu Ser Leu Ser Arg Thr Asn Ala Phe Phe
        115                 120                 125

ctg ggg ggc ggc aag gct ctg gtg aac gcc tac tac gcg acc gcc gag      432
Leu Gly Gly Gly Lys Ala Leu Val Asn Ala Tyr Tyr Ala Thr Ala Glu
    130                 135                 140

cgc ctg ggc gtc gac atc ctc tat gac agc gaa gtc acc gag atc gtg      480
Arg Leu Gly Val Asp Ile Leu Tyr Asp Ser Glu Val Thr Glu Ile Val
145                 150                 155                 160

ctc gaa ggc ggc cgg gtc cgg cgt ctg gtg gtc cgc agc cag ggg ttc      528
Leu Glu Gly Gly Arg Val Arg Arg Leu Val Val Arg Ser Gln Gly Phe
                165                 170                 175

ccc atc gag gtg gag gcg cgc gcg gtg atc gcc tcg tcg ggc ggc ttc      576
Pro Ile Glu Val Glu Ala Arg Ala Val Ile Ala Ser Ser Gly Gly Phe
            180                 185                 190

cag gcc aac ctg caa tgg ctg gcg aac gcc tgg ggc ccg gcg gcg tcg      624
Gln Ala Asn Leu Gln Trp Leu Ala Asn Ala Trp Gly Pro Ala Ala Ser
        195                 200                 205

aat ttc atc gta cgc ggg acg ccc tac gcg acg ggc acg gtg ctg cgc      672
Asn Phe Ile Val Arg Gly Thr Pro Tyr Ala Thr Gly Thr Val Leu Arg
    210                 215                 220

aac ctg ctc gac cag ggc gtg gcc tcg gtg ggc gat ccg acc cag tgc      720
Asn Leu Leu Asp Gln Gly Val Ala Ser Val Gly Asp Pro Thr Gln Cys
225                 230                 235                 240

cat gct gtc gcc atc gac ggg cgc gcg ccc aag tac gac ggg ggg atc      768
His Ala Val Ala Ile Asp Gly Arg Ala Pro Lys Tyr Asp Gly Gly Ile
                245                 250                 255

gtc acc cga ctg gac tgc gtg ccg ttc tcg atc gtg gtc aat cgc gac      816
Val Thr Arg Leu Asp Cys Val Pro Phe Ser Ile Val Val Asn Arg Asp
            260                 265                 270

ggc caa cgc ttc tac gac gag ggc gag gac atc tgg ccc aag cga tat      864
Gly Gln Arg Phe Tyr Asp Glu Gly Glu Asp Ile Trp Pro Lys Arg Tyr
        275                 280                 285

gcg atc tgg ggg cgt ctg acc gcg caa cag ccc gat cag atc gcc tac      912
Ala Ile Trp Gly Arg Leu Thr Ala Gln Gln Pro Asp Gln Ile Ala Tyr
    290                 295                 300

agc atc atc gac agc cga tcc gaa cga ctt ttc atg ccg tcg gtg ttt      960
Ser Ile Ile Asp Ser Arg Ser Glu Arg Leu Phe Met Pro Ser Val Phe
305                 310                 315                 320

ccc ccg atc aaa gcc gac tcg att tcc gaa ctc gcg gcc aag ctc ggg     1008
Pro Pro Ile Lys Ala Asp Ser Ile Ser Glu Leu Ala Ala Lys Leu Gly
                325                 330                 335

ctg gag ccg gcg acg ctc gcg cag acc atc gag acg ttc aat cgc gcc     1056
Leu Glu Pro Ala Thr Leu Ala Gln Thr Ile Glu Thr Phe Asn Arg Ala
            340                 345                 350

tgc caa ccc ggt cgc ttc gat ccg cag gat ctt gac ggg gtc cgc acc     1104
Cys Gln Pro Gly Arg Phe Asp Pro Gln Asp Leu Asp Gly Val Arg Thr
        355                 360                 365

gag ggg atc acg ccg tgc aag tcc aat tgg gcc cgg ccg atc acc gag     1152
Glu Gly Ile Thr Pro Cys Lys Ser Asn Trp Ala Arg Pro Ile Thr Glu
    370                 375                 380
```

-continued

```
ccg ccg ttc agc gca tat ccc ctg cgg ccc ggc atc acc ttc acc tac      1200
Pro Pro Phe Ser Ala Tyr Pro Leu Arg Pro Gly Ile Thr Phe Thr Tyr
385                 390                 395                 400

ctc ggc gtc aag gtc gat gaa cgc gcc agg gtg atc ctg gcc tcc ggc      1248
Leu Gly Val Lys Val Asp Glu Arg Ala Arg Val Ile Leu Ala Ser Gly
                405                 410                 415

cag ccg aca gag aac ctg ttc gcg tct ggc gag atc atg gcc ggg agc      1296
Gln Pro Thr Glu Asn Leu Phe Ala Ser Gly Glu Ile Met Ala Gly Ser
            420                 425                 430

att ctt ggg cgc ggt tac ctg gcg ggc ttc ggc atg gcg atc ggg acc      1344
Ile Leu Gly Arg Gly Tyr Leu Ala Gly Phe Gly Met Ala Ile Gly Thr
        435                 440                 445

gtc ttc gga cgc att gcg ggc cgg gag gcc gca tat cat gca gca          1389
Val Phe Gly Arg Ile Ala Gly Arg Glu Ala Ala Tyr His Ala Ala
    450                 455                 460


<210> SEQ ID NO 23
<211> LENGTH: 463
<212> TYPE: PRT
<213> ORGANISM: Bacterium 2412.1

<400> SEQUENCE: 23

Met Gly Ala Lys Leu Lys Tyr Asp Val Val Val Val Gly Gly Gly Asn
  1               5                  10                  15

Ala Ala Met Thr Ala Ala Val Thr Ala Arg Glu Ala Gly Ala Thr Val
            20                  25                  30

Leu Val Leu Glu His Ala Pro Arg Ser Met Arg Gly Gly Asn Ser Arg
        35                  40                  45

His Thr Arg Asn Met Arg Thr Met His Glu Ala Pro Leu Ala Val Leu
    50                  55                  60

Thr Gly Gln Tyr Ser Glu Asp Glu Tyr Trp Asn Asp Leu Lys Arg Val
 65                  70                  75                  80

Thr Gly Gly Glu Thr Asp Glu Ala Leu Ala Arg Leu Val Ile Arg Ser
                85                  90                  95

Thr Thr Asp Ala Ile Pro Phe Met Leu Arg Cys Gly Val Arg Phe Gln
            100                 105                 110

Pro Ser Leu Ser Gly Thr Leu Ser Leu Ser Arg Thr Asn Ala Phe Phe
        115                 120                 125

Leu Gly Gly Gly Lys Ala Leu Val Asn Ala Tyr Tyr Ala Thr Ala Glu
    130                 135                 140

Arg Leu Gly Val Asp Ile Leu Tyr Asp Ser Glu Val Thr Glu Ile Val
145                 150                 155                 160

Leu Glu Gly Gly Arg Val Arg Arg Leu Val Val Arg Ser Gln Gly Phe
                165                 170                 175

Pro Ile Glu Val Glu Ala Arg Ala Val Ile Ala Ser Ser Gly Gly Phe
            180                 185                 190

Gln Ala Asn Leu Gln Trp Leu Ala Asn Ala Trp Gly Pro Ala Ala Ser
        195                 200                 205

Asn Phe Ile Val Arg Gly Thr Pro Tyr Ala Thr Gly Thr Val Leu Arg
    210                 215                 220

Asn Leu Leu Asp Gln Gly Val Ala Ser Val Gly Asp Pro Thr Gln Cys
225                 230                 235                 240

His Ala Val Ala Ile Asp Gly Arg Ala Pro Lys Tyr Asp Gly Gly Ile
                245                 250                 255

Val Thr Arg Leu Asp Cys Val Pro Phe Ser Ile Val Val Asn Arg Asp
            260                 265                 270
```

-continued

```
Gly Gln Arg Phe Tyr Asp Glu Gly Glu Asp Ile Trp Pro Lys Arg Tyr
        275                 280                 285

Ala Ile Trp Gly Arg Leu Thr Ala Gln Gln Pro Asp Gln Ile Ala Tyr
    290                 295                 300

Ser Ile Ile Asp Ser Arg Ser Glu Arg Leu Phe Met Pro Ser Val Phe
305                 310                 315                 320

Pro Pro Ile Lys Ala Asp Ser Ile Ser Glu Leu Ala Ala Lys Leu Gly
                325                 330                 335

Leu Glu Pro Ala Thr Leu Ala Gln Thr Ile Glu Thr Phe Asn Arg Ala
            340                 345                 350

Cys Gln Pro Gly Arg Phe Asp Pro Gln Asp Leu Asp Gly Val Arg Thr
        355                 360                 365

Glu Gly Ile Thr Pro Cys Lys Ser Asn Trp Ala Arg Pro Ile Thr Glu
    370                 375                 380

Pro Pro Phe Ser Ala Tyr Pro Leu Arg Pro Gly Ile Thr Phe Thr Tyr
385                 390                 395                 400

Leu Gly Val Lys Val Asp Glu Arg Ala Arg Val Ile Leu Ala Ser Gly
                405                 410                 415

Gln Pro Thr Glu Asn Leu Phe Ala Ser Gly Glu Ile Met Ala Gly Ser
            420                 425                 430

Ile Leu Gly Arg Gly Tyr Leu Ala Gly Phe Gly Met Ala Ile Gly Thr
        435                 440                 445

Val Phe Gly Arg Ile Ala Gly Arg Glu Ala Ala Tyr His Ala Ala
    450                 455                 460


<210> SEQ ID NO 24
<211> LENGTH: 2403
<212> TYPE: DNA
<213> ORGANISM: Bacterium 2412.1
<220> FEATURE:
<223> OTHER INFORMATION: fccL TonB-dependent Receptor
<221> NAME/KEY: CDS
<222> LOCATION: ()..(2403)

<400> SEQUENCE: 24

atg cct agg gat acg aca ccg aat ttc gct ccg gtc acc acg gca aaa        48
Met Pro Arg Asp Thr Thr Pro Asn Phe Ala Pro Val Thr Thr Ala Lys
  1               5                  10                  15

gag ggc cgc cga cac cga ggc agc acc gcc tta cga agg ctc atg ctg        96
Glu Gly Arg Arg His Arg Gly Ser Thr Ala Leu Arg Arg Leu Met Leu
             20                  25                  30

acg gcg gcc ggc agc gcc ctg gtg ctg ggt ctt gcg ccc aag gcg ctc       144
Thr Ala Ala Gly Ser Ala Leu Val Leu Gly Leu Ala Pro Lys Ala Leu
         35                  40                  45

gcg cag gtg gcg gtt ccg ccg gct ggt cac gag gcg tcg cag gag gtg       192
Ala Gln Val Ala Val Pro Pro Ala Gly His Glu Ala Ser Gln Glu Val
     50                  55                  60

cag gag atc gtc gtc acc gcg cag cgc cgc agc gag aac att cag aat       240
Gln Glu Ile Val Val Thr Ala Gln Arg Arg Ser Glu Asn Ile Gln Asn
 65                  70                  75                  80

gtg ccg gtc tcg gtg cag gcg ctg tcg gca gcg cag ctc gag cgc gaa       288
Val Pro Val Ser Val Gln Ala Leu Ser Ala Ala Gln Leu Glu Arg Glu
                 85                  90                  95

ggg atc aaa cag acc agc gat atc gcc cga gtg acg ccc aac gtc acc       336
Gly Ile Lys Gln Thr Ser Asp Ile Ala Arg Val Thr Pro Asn Val Thr
            100                 105                 110

atc gcc atg ccc aac ggc gaa ggc aac cag ccg gcg gtg acg atc cgc       384
Ile Ala Met Pro Asn Gly Glu Gly Asn Gln Pro Ala Val Thr Ile Arg
```

-continued

```
        115                 120                 125

ggc atc ggc ctc aac gac ttc aat tcc aac aac gcc ggc ccg aac gcg      432
Gly Ile Gly Leu Asn Asp Phe Asn Ser Asn Asn Ala Gly Pro Asn Ala
    130                 135                 140

atc tat gtc gac gat gtc tat atc agc gcc ccg tcg gcc cag acc ttc      480
Ile Tyr Val Asp Asp Val Tyr Ile Ser Ala Pro Ser Ala Gln Thr Phe
145                 150                 155                 160

gga atc ttc gac atc aac cag atc cag gtt ctc aaa gga ccg caa ggt      528
Gly Ile Phe Asp Ile Asn Gln Ile Gln Val Leu Lys Gly Pro Gln Gly
                165                 170                 175

acg ctc tat ggg cgc aac tcc agc ggt ggg gcc ttg gtg ttc acg tcc      576
Thr Leu Tyr Gly Arg Asn Ser Ser Gly Gly Ala Leu Val Phe Thr Ser
            180                 185                 190

aga gcg ccg agc caa gac ttc gcc gcg gac gcc cat ttc gat tac ggc      624
Arg Ala Pro Ser Gln Asp Phe Ala Ala Asp Ala His Phe Asp Tyr Gly
        195                 200                 205

agc tac aac acc tat caa ctg caa gcc ggc gtc ggc ggc cct ctg agc      672
Ser Tyr Asn Thr Tyr Gln Leu Gln Ala Gly Val Gly Gly Pro Leu Ser
    210                 215                 220

gat cag cta agc gcc cgc ctg gcc ttc gtc gtc aac cac tcc gac ggg      720
Asp Gln Leu Ser Ala Arg Leu Ala Phe Val Val Asn His Ser Asp Gly
225                 230                 235                 240

ttc atg cac aac acg ctg acg ggc ggt tcg gcg tcg ggc acg gac aat      768
Phe Met His Asn Thr Leu Thr Gly Gly Ser Ala Ser Gly Thr Asp Asn
                245                 250                 255

cag gcc gtc agg ctg caa ctg ctc tac cga cct aat gac agg ctg aaa      816
Gln Ala Val Arg Leu Gln Leu Leu Tyr Arg Pro Asn Asp Arg Leu Lys
            260                 265                 270

gta ctt ctc agt tcg gcc tat ggt cat gtc aac tcg ccg atc gtc cag      864
Val Leu Leu Ser Ser Ala Tyr Gly His Val Asn Ser Pro Ile Val Gln
        275                 280                 285

tac cga cac ttg ggc gcc ttc gcg gca gga acc caa tcc agc gcc agc      912
Tyr Arg His Leu Gly Ala Phe Ala Ala Gly Thr Gln Ser Ser Ala Ser
    290                 295                 300

ccg act ctc tgc agc ccc gag cag gtc cgc gcc gga ggt tgc gtc aac      960
Pro Thr Leu Cys Ser Pro Glu Gln Val Arg Ala Gly Gly Cys Val Asn
305                 310                 315                 320

gtg ttc ggc gca ggc acg ccg agc ggc ttc tac gac ggt tcc agc gat     1008
Val Phe Gly Ala Gly Thr Pro Ser Gly Phe Tyr Asp Gly Ser Ser Asp
                325                 330                 335

cgc ggt gaa cgc ttg cgc gtg gaa aac ttc ctg cag cag gcc cgc gcc     1056
Arg Gly Glu Arg Leu Arg Val Glu Asn Phe Leu Gln Gln Ala Arg Ala
            340                 345                 350

gac tat gag gtc ggt ccg gtg acc ctg aca tcg atc agc gcc ttc acg     1104
Asp Tyr Glu Val Gly Pro Val Thr Leu Thr Ser Ile Ser Ala Phe Thr
        355                 360                 365

cac agc aaa aag agc ggc ccc gac gac gcc gac ggg acg tct gac agt     1152
His Ser Lys Lys Ser Gly Pro Asp Asp Ala Asp Gly Thr Ser Asp Ser
    370                 375                 380

ctg ctc cac gcg acc tac ggc gtt cgc tcc gac acc tgg acc caa gag     1200
Leu Leu His Ala Thr Tyr Gly Val Arg Ser Asp Thr Trp Thr Gln Glu
385                 390                 395                 400

ttc cgc gcc gcc tat tcc ggc cag cgc ctg cat tgg gtg gcg ggc gcc     1248
Phe Arg Ala Ala Tyr Ser Gly Gln Arg Leu His Trp Val Ala Gly Ala
                405                 410                 415

tac tat ctc gac gag acc ctc aag caa aat cag cca ctt agc atc ttc     1296
Tyr Tyr Leu Asp Glu Thr Leu Lys Gln Asn Gln Pro Leu Ser Ile Phe
            420                 425                 430

tac gat gga gat cgc ttc ggc ggc ctg ggc atc ccg gcc agg gcg gga     1344
```

-continued

```
Tyr Asp Gly Asp Arg Phe Gly Gly Leu Gly Ile Pro Ala Arg Ala Gly
        435                 440                 445

gcc ttc gac ggc atc gcg caa aag agc tta agc caa aac act cag aaa      1392
Ala Phe Asp Gly Ile Ala Gln Lys Ser Leu Ser Gln Asn Thr Gln Lys
    450                 455                 460

aca cgg tcg ata gcc gcc ttc ggc caa gcc gac tat acc ttg gac cgg      1440
Thr Arg Ser Ile Ala Ala Phe Gly Gln Ala Asp Tyr Thr Leu Asp Arg
465                 470                 475                 480

ttc acc ctg acc ttg ggc ggt cgt tac acc cat gaa cgc aag acg ttc      1488
Phe Thr Leu Thr Leu Gly Gly Arg Tyr Thr His Glu Arg Lys Thr Phe
                485                 490                 495

gat cac ttc agc gcg acc cag gtc caa gca gga ggc ctt ggg aaa tac      1536
Asp His Phe Ser Ala Thr Gln Val Gln Ala Gly Gly Leu Gly Lys Tyr
            500                 505                 510

ggt cct ctc ggc aag atc gtc tcg ctg agc gaa gcg ttc aag gct tcc      1584
Gly Pro Leu Gly Lys Ile Val Ser Leu Ser Glu Ala Phe Lys Ala Ser
        515                 520                 525

gat ccg acc tgg cgc gcc gcg ctt tcc tac cgt ccc gcc gag cgt gtt      1632
Asp Pro Thr Trp Arg Ala Ala Leu Ser Tyr Arg Pro Ala Glu Arg Val
    530                 535                 540

atg gtc tac ggc agc gtc gcc acc ggc ttt aag ggc ggc gcc ttc aac      1680
Met Val Tyr Gly Ser Val Ala Thr Gly Phe Lys Gly Gly Ala Phe Asn
545                 550                 555                 560

ggc ggg ttc ctg agc agc aac ccc aac aaa gcc ctc gcc gcg gtc aaa      1728
Gly Gly Phe Leu Ser Ser Asn Pro Asn Lys Ala Leu Ala Ala Val Lys
                565                 570                 575

ccc gtc gca ccg gag aag gtg acc acc tac gaa ctg ggc ttc aag tcg      1776
Pro Val Ala Pro Glu Lys Val Thr Thr Tyr Glu Leu Gly Phe Lys Ser
            580                 585                 590

agc ctg ttc gag cgt cgc ctg gtg gtc aac ggc gcg gct ttc tac aac      1824
Ser Leu Phe Glu Arg Arg Leu Val Val Asn Gly Ala Ala Phe Tyr Asn
        595                 600                 605

agc tac gac aac gag cag atc ctg gcc aac acg gcc gtc gtc gtg gat      1872
Ser Tyr Asp Asn Glu Gln Ile Leu Ala Asn Thr Ala Val Val Val Asp
    610                 615                 620

acc gtg acc ggc cct gtt acc gtg acg acg aac gtc ctg acc aac gcc      1920
Thr Val Thr Gly Pro Val Thr Val Thr Thr Asn Val Leu Thr Asn Ala
625                 630                 635                 640

cga aag gcc cac tcc cag ggc gtg gaa ttg gaa gta aag gcc gtc ccg      1968
Arg Lys Ala His Ser Gln Gly Val Glu Leu Glu Val Lys Ala Val Pro
                645                 650                 655

atc ccg gat ctc gtc ctc agc ctg cag ccg gcc tgg ctg cga acg cgg      2016
Ile Pro Asp Leu Val Leu Ser Leu Gln Pro Ala Trp Leu Arg Thr Arg
            660                 665                 670

ctg gac gag gcg ggc ttc tcc ggg gga acg tcg ctg gaa ggc aag caa      2064
Leu Asp Glu Ala Gly Phe Ser Gly Gly Thr Ser Leu Glu Gly Lys Gln
        675                 680                 685

ctg gcc aat gcg ccg aag ttc tcg ctc tac gcc gcg gcg gac tac acc      2112
Leu Ala Asn Ala Pro Lys Phe Ser Leu Tyr Ala Ala Ala Asp Tyr Thr
    690                 695                 700

ttc cat ctt gcc gac gac gac agc gtc aac gtc gcc ttc acc tcg gcc      2160
Phe His Leu Ala Asp Asp Asp Ser Val Asn Val Ala Phe Thr Ser Ala
705                 710                 715                 720

tac aag tcg cac cag ttc ttc gat tcg acg aac gcc ccc tat acc cag      2208
Tyr Lys Ser His Gln Phe Phe Asp Ser Thr Asn Ala Pro Tyr Thr Gln
                725                 730                 735

cag gag ggc tac tgg gtg cac aac gcc agc ctg acc ttc aac tcc aga      2256
Gln Glu Gly Tyr Trp Val His Asn Ala Ser Leu Thr Phe Asn Ser Arg
            740                 745                 750
```

-continued

```
aac cac tgg gat gtc ggg ttc aat gtc cga aac ctg acg ggc acg aag      2304
Asn His Trp Asp Val Gly Phe Asn Val Arg Asn Leu Thr Gly Thr Lys
        755                 760                 765

tac tac aac tat ctg ttc gac gag ggg gcg acg ttc ggc ttc atc aac      2352
Tyr Tyr Asn Tyr Leu Phe Asp Glu Gly Ala Thr Phe Gly Phe Ile Asn
    770                 775                 780

ggc gtc gtg gcc gcg ccg cgg acc tac agc gtg caa ttc aac ctg cat      2400
Gly Val Val Ala Ala Pro Arg Thr Tyr Ser Val Gln Phe Asn Leu His
785                 790                 795                 800

ctc                                                                  2403
Leu


<210> SEQ ID NO 25
<211> LENGTH: 801
<212> TYPE: PRT
<213> ORGANISM: Bacterium 2412.1

<400> SEQUENCE: 25

Met Pro Arg Asp Thr Thr Pro Asn Phe Ala Pro Val Thr Thr Ala Lys
  1               5                  10                  15

Glu Gly Arg Arg His Arg Gly Ser Thr Ala Leu Arg Arg Leu Met Leu
             20                  25                  30

Thr Ala Ala Gly Ser Ala Leu Val Leu Gly Leu Ala Pro Lys Ala Leu
         35                  40                  45

Ala Gln Val Ala Val Pro Pro Ala Gly His Glu Ala Ser Gln Glu Val
     50                  55                  60

Gln Glu Ile Val Val Thr Ala Gln Arg Arg Ser Glu Asn Ile Gln Asn
 65                  70                  75                  80

Val Pro Val Ser Val Gln Ala Leu Ser Ala Ala Gln Leu Glu Arg Glu
                 85                  90                  95

Gly Ile Lys Gln Thr Ser Asp Ile Ala Arg Val Thr Pro Asn Val Thr
            100                 105                 110

Ile Ala Met Pro Asn Gly Glu Gly Asn Gln Pro Ala Val Thr Ile Arg
        115                 120                 125

Gly Ile Gly Leu Asn Asp Phe Asn Ser Asn Asn Ala Gly Pro Asn Ala
    130                 135                 140

Ile Tyr Val Asp Asp Val Tyr Ile Ser Ala Pro Ser Ala Gln Thr Phe
145                 150                 155                 160

Gly Ile Phe Asp Ile Asn Gln Ile Gln Val Leu Lys Gly Pro Gln Gly
                165                 170                 175

Thr Leu Tyr Gly Arg Asn Ser Ser Gly Gly Ala Leu Val Phe Thr Ser
            180                 185                 190

Arg Ala Pro Ser Gln Asp Phe Ala Ala Asp Ala His Phe Asp Tyr Gly
        195                 200                 205

Ser Tyr Asn Thr Tyr Gln Leu Gln Ala Gly Val Gly Gly Pro Leu Ser
    210                 215                 220

Asp Gln Leu Ser Ala Arg Leu Ala Phe Val Val Asn His Ser Asp Gly
225                 230                 235                 240

Phe Met His Asn Thr Leu Thr Gly Gly Ser Ala Ser Gly Thr Asp Asn
                245                 250                 255

Gln Ala Val Arg Leu Gln Leu Leu Tyr Arg Pro Asn Asp Arg Leu Lys
            260                 265                 270

Val Leu Leu Ser Ser Ala Tyr Gly His Val Asn Ser Pro Ile Val Gln
        275                 280                 285

Tyr Arg His Leu Gly Ala Phe Ala Ala Gly Thr Gln Ser Ser Ala Ser
    290                 295                 300
```

-continued

```
Pro Thr Leu Cys Ser Pro Glu Gln Val Arg Ala Gly Gly Cys Val Asn
305                 310                 315                 320

Val Phe Gly Ala Gly Thr Pro Ser Gly Phe Tyr Asp Gly Ser Ser Asp
                325                 330                 335

Arg Gly Glu Arg Leu Arg Val Glu Asn Phe Leu Gln Gln Ala Arg Ala
            340                 345                 350

Asp Tyr Glu Val Gly Pro Val Thr Leu Thr Ser Ile Ser Ala Phe Thr
        355                 360                 365

His Ser Lys Lys Ser Gly Pro Asp Asp Ala Asp Gly Thr Ser Asp Ser
    370                 375                 380

Leu Leu His Ala Thr Tyr Gly Val Arg Ser Asp Thr Trp Thr Gln Glu
385                 390                 395                 400

Phe Arg Ala Ala Tyr Ser Gly Gln Arg Leu His Trp Val Ala Gly Ala
                405                 410                 415

Tyr Tyr Leu Asp Glu Thr Leu Lys Gln Asn Gln Pro Leu Ser Ile Phe
            420                 425                 430

Tyr Asp Gly Asp Arg Phe Gly Gly Leu Gly Ile Pro Ala Arg Ala Gly
        435                 440                 445

Ala Phe Asp Gly Ile Ala Gln Lys Ser Leu Ser Gln Asn Thr Gln Lys
    450                 455                 460

Thr Arg Ser Ile Ala Ala Phe Gly Gln Ala Asp Tyr Thr Leu Asp Arg
465                 470                 475                 480

Phe Thr Leu Thr Leu Gly Gly Arg Tyr Thr His Glu Arg Lys Thr Phe
                485                 490                 495

Asp His Phe Ser Ala Thr Gln Val Gln Ala Gly Gly Leu Gly Lys Tyr
            500                 505                 510

Gly Pro Leu Gly Lys Ile Val Ser Leu Ser Glu Ala Phe Lys Ala Ser
        515                 520                 525

Asp Pro Thr Trp Arg Ala Ala Leu Ser Tyr Arg Pro Ala Glu Arg Val
    530                 535                 540

Met Val Tyr Gly Ser Val Ala Thr Gly Phe Lys Gly Gly Ala Phe Asn
545                 550                 555                 560

Gly Gly Phe Leu Ser Ser Asn Pro Asn Lys Ala Leu Ala Ala Val Lys
                565                 570                 575

Pro Val Ala Pro Glu Lys Val Thr Thr Tyr Glu Leu Gly Phe Lys Ser
            580                 585                 590

Ser Leu Phe Glu Arg Arg Leu Val Val Asn Gly Ala Ala Phe Tyr Asn
        595                 600                 605

Ser Tyr Asp Asn Glu Gln Ile Leu Ala Asn Thr Ala Val Val Val Asp
    610                 615                 620

Thr Val Thr Gly Pro Val Thr Val Thr Thr Asn Val Leu Thr Asn Ala
625                 630                 635                 640

Arg Lys Ala His Ser Gln Gly Val Glu Leu Glu Val Lys Ala Val Pro
                645                 650                 655

Ile Pro Asp Leu Val Leu Ser Leu Gln Pro Ala Trp Leu Arg Thr Arg
            660                 665                 670

Leu Asp Glu Ala Gly Phe Ser Gly Gly Thr Ser Leu Glu Gly Lys Gln
        675                 680                 685

Leu Ala Asn Ala Pro Lys Phe Ser Leu Tyr Ala Ala Ala Asp Tyr Thr
    690                 695                 700

Phe His Leu Ala Asp Asp Asp Ser Val Asn Val Ala Phe Thr Ser Ala
705                 710                 715                 720
```

-continued

```
Tyr Lys Ser His Gln Phe Phe Asp Ser Thr Asn Ala Pro Tyr Thr Gln
                725                 730                 735

Gln Glu Gly Tyr Trp Val His Asn Ala Ser Leu Thr Phe Asn Ser Arg
            740                 745                 750

Asn His Trp Asp Val Gly Phe Asn Val Arg Asn Leu Thr Gly Thr Lys
        755                 760                 765

Tyr Tyr Asn Tyr Leu Phe Asp Glu Gly Ala Thr Phe Gly Phe Ile Asn
    770                 775                 780

Gly Val Val Ala Ala Pro Arg Thr Tyr Ser Val Gln Phe Asn Leu His
785                 790                 795                 800

Leu


<210> SEQ ID NO 26
<211> LENGTH: 1173
<212> TYPE: DNA
<213> ORGANISM: Bacterium 2412.1
<220> FEATURE:
<223> OTHER INFORMATION: fccM
<221> NAME/KEY: CDS
<222> LOCATION: ()..(1173)

<400> SEQUENCE: 26

atg gct cgc atc ggc ttc tct ttc gtc cca ccg ccg aca gct cgg ctc       48
Met Ala Arg Ile Gly Phe Ser Phe Val Pro Pro Pro Thr Ala Arg Leu
  1               5                  10                  15

ggg aaa gtg act gtg tgg atg gaa ctg ggg cgt tcg tct gag cgc cgg       96
Gly Lys Val Thr Val Trp Met Glu Leu Gly Arg Ser Ser Glu Arg Arg
             20                  25                  30

aga cga cgc aaa tcg agg cgg cgc gga ctc cag atc gag aac atc gcc      144
Arg Arg Arg Lys Ser Arg Arg Arg Gly Leu Gln Ile Glu Asn Ile Ala
         35                  40                  45

tcg acc gtc gtc acg cca tcg tcg acg gcg tca ccc cgc ctt ggc gcc      192
Ser Thr Val Val Thr Pro Ser Ser Thr Ala Ser Pro Arg Leu Gly Ala
     50                  55                  60

atc cgc gca agg ggg gat gga agg tcc ggg cga cac cac cgc cgc gcg      240
Ile Arg Ala Arg Gly Asp Gly Arg Ser Gly Arg His His Arg Arg Ala
 65                  70                  75                  80

gcc ctc ggg acc gaa tgt cat ggt cga ctt gcc cgt aga ata ggc agg      288
Ala Leu Gly Thr Glu Cys His Gly Arg Leu Ala Arg Arg Ile Gly Arg
                 85                  90                  95

cca ggt aag ggc gtc ccc ggc ggg gtc gcc att ctt ggc gaa ccg gac      336
Pro Gly Lys Gly Val Pro Gly Gly Val Ala Ile Leu Gly Glu Pro Asp
            100                 105                 110

cca ggc gga gga cat cag ttg gcc cag cgc acg gtc ggc ggg cgt ggg      384
Pro Gly Gly Gly His Gln Leu Ala Gln Arg Thr Val Gly Gly Arg Gly
        115                 120                 125

ccc ctc ggg cgg cca atc gaa cag acc caa ctc gtc gag ctt gaa cac      432
Pro Leu Gly Arg Pro Ile Glu Gln Thr Gln Leu Val Glu Leu Glu His
    130                 135                 140

ccc gaa aac gta ggg aat ttc ggc tcc gtg ggt agc cgg cgc tct tcc      480
Pro Glu Asn Val Gly Asn Phe Gly Ser Val Gly Ser Arg Arg Ser Ser
145                 150                 155                 160

acc ctc ggt att acc gtt gaa ctg ata acg cca cac ggg cgc gcc ctg      528
Thr Leu Gly Ile Thr Val Glu Leu Ile Thr Pro His Gly Arg Ala Leu
                165                 170                 175

gcg cac aag cgc ttc cga gaa ggc cga gac ccc ccg att gaa ctg att      576
Ala His Lys Arg Phe Arg Glu Gly Arg Asp Pro Pro Ile Glu Leu Ile
            180                 185                 190

gtc gcc gaa gat gcg cgc gac cat ttc ctt ggg cgt ggc ccg gcc gtc      624
Val Ala Glu Asp Ala Arg Asp His Phe Leu Gly Arg Gly Pro Ala Val
```

-continued

```
        195                 200                 205

gag ggg ata gca cgc cgc cac ggc ggc ggc ttg gtc gcc aaa ctg cgc      672
Glu Gly Ile Ala Arg Arg His Gly Gly Gly Leu Val Ala Lys Leu Arg
    210                 215                 220

ctc cag ata ggc ttg gta gtc cgc tgg cgt ctc cat cgg cgc gcg ccc      720
Leu Gln Ile Gly Leu Val Val Arg Trp Arg Leu His Arg Arg Ala Pro
225                 230                 235                 240

gag gaa ggc gcg gcc ttc gtc ggc att ggt tcc gat cag gac ccg aac      768
Glu Glu Gly Ala Ala Phe Val Gly Ile Gly Ser Asp Gln Asp Pro Asn
                245                 250                 255

cgg cgc cag ctg ccc cgc cgc gat cgc cgc gct gtc ggt ctg cgg cag      816
Arg Arg Gln Leu Pro Arg Arg Asp Arg Arg Ala Val Gly Leu Arg Gln
            260                 265                 270

cac atg gcc atc gac gat cgg tcc ggt cgg acg cgg cct gcg cag gtc      864
His Met Ala Ile Asp Asp Arg Ser Gly Arg Thr Arg Pro Ala Gln Val
        275                 280                 285

ccg cga tgc cgg gcg ggc cgc gtc ggc gcg cgc cat cag ggt ggc tgg      912
Pro Arg Cys Arg Ala Gly Arg Val Gly Ala Arg His Gln Gly Gly Trp
    290                 295                 300

gtc ggt cga gcg cag tcg cga aag atc ggc gtc gag gcg ctc gcc cga      960
Val Gly Arg Ala Gln Ser Arg Lys Ile Gly Val Glu Ala Leu Ala Arg
305                 310                 315                 320

ggc ggc gct gtc ggc gag cgt cgc gag cgg tcg cgt cag ccc tgg act     1008
Gly Gly Ala Val Gly Glu Arg Arg Glu Arg Ser Arg Gln Pro Trp Thr
                325                 330                 335

ttc gag gat agc gcc acg gaa gag acc ctt gct cag cgg cga ggt gag     1056
Phe Glu Asp Ser Ala Thr Glu Glu Thr Leu Ala Gln Arg Arg Gly Glu
            340                 345                 350

cag aag tcc gat cgc gct cgc tcc ggc cga ttc acc aaa gac cgt cac     1104
Gln Lys Ser Asp Arg Ala Arg Ser Gly Arg Phe Thr Lys Asp Arg His
        355                 360                 365

tcg gcc ggg gtc ccc tcc gaa ggc gcg ggc gtt gct ctg cac cca ccg     1152
Ser Ala Gly Val Pro Ser Glu Gly Ala Gly Val Ala Leu His Pro Pro
    370                 375                 380

aag agc ggc gag aat gtc gag                                         1173
Lys Ser Gly Glu Asn Val Glu
385                 390


<210> SEQ ID NO 27
<211> LENGTH: 391
<212> TYPE: PRT
<213> ORGANISM: Bacterium 2412.1

<400> SEQUENCE: 27

Met Ala Arg Ile Gly Phe Ser Phe Val Pro Pro Pro Thr Ala Arg Leu
  1               5                  10                  15

Gly Lys Val Thr Val Trp Met Glu Leu Gly Arg Ser Ser Glu Arg Arg
            20                  25                  30

Arg Arg Arg Lys Ser Arg Arg Arg Gly Leu Gln Ile Glu Asn Ile Ala
        35                  40                  45

Ser Thr Val Val Thr Pro Ser Ser Thr Ala Ser Pro Arg Leu Gly Ala
    50                  55                  60

Ile Arg Ala Arg Gly Asp Gly Arg Ser Gly Arg His His Arg Arg Ala
 65                  70                  75                  80

Ala Leu Gly Thr Glu Cys His Gly Arg Leu Ala Arg Arg Ile Gly Arg
                85                  90                  95

Pro Gly Lys Gly Val Pro Gly Gly Val Ala Ile Leu Gly Glu Pro Asp
            100                 105                 110
```

-continued

```
Pro Gly Gly Gly His Gln Leu Ala Gln Arg Thr Val Gly Gly Arg Gly
        115                 120                 125

Pro Leu Gly Arg Pro Ile Glu Gln Thr Gln Leu Val Glu Leu Glu His
    130                 135                 140

Pro Glu Asn Val Gly Asn Phe Gly Ser Val Gly Ser Arg Arg Ser Ser
145                 150                 155                 160

Thr Leu Gly Ile Thr Val Glu Leu Ile Thr Pro His Gly Arg Ala Leu
                165                 170                 175

Ala His Lys Arg Phe Arg Glu Gly Arg Asp Pro Pro Ile Glu Leu Ile
            180                 185                 190

Val Ala Glu Asp Ala Arg Asp His Phe Leu Gly Arg Gly Pro Ala Val
        195                 200                 205

Glu Gly Ile Ala Arg Arg His Gly Gly Gly Leu Val Ala Lys Leu Arg
    210                 215                 220

Leu Gln Ile Gly Leu Val Val Arg Trp Arg Leu His Arg Arg Ala Pro
225                 230                 235                 240

Glu Glu Gly Ala Ala Phe Val Gly Ile Gly Ser Asp Gln Asp Pro Asn
                245                 250                 255

Arg Arg Gln Leu Pro Arg Arg Asp Arg Arg Ala Val Gly Leu Arg Gln
            260                 265                 270

His Met Ala Ile Asp Asp Arg Ser Gly Arg Thr Arg Pro Ala Gln Val
        275                 280                 285

Pro Arg Cys Arg Ala Gly Arg Val Gly Ala Arg His Gln Gly Gly Trp
    290                 295                 300

Val Gly Arg Ala Gln Ser Arg Lys Ile Gly Val Glu Ala Leu Ala Arg
305                 310                 315                 320

Gly Gly Ala Val Gly Glu Arg Arg Glu Arg Ser Arg Gln Pro Trp Thr
                325                 330                 335

Phe Glu Asp Ser Ala Thr Glu Glu Thr Leu Ala Gln Arg Arg Gly Glu
            340                 345                 350

Gln Lys Ser Asp Arg Ala Arg Ser Gly Arg Phe Thr Lys Asp Arg His
        355                 360                 365

Ser Ala Gly Val Pro Ser Glu Gly Ala Gly Val Ala Leu His Pro Pro
    370                 375                 380

Lys Ser Gly Glu Asn Val Glu
385                 390


<210> SEQ ID NO 28
<211> LENGTH: 1179
<212> TYPE: DNA
<213> ORGANISM: Bacterium 2412.1
<220> FEATURE:
<223> OTHER INFORMATION: fccN  Citrate Utilization B
<221> NAME/KEY: CDS
<222> LOCATION: ()..(1179)

<400> SEQUENCE: 28

atg cag cat aat gtc ctg gat ttc gtg acc aag acg cgc acg ggc gag       48
Met Gln His Asn Val Leu Asp Phe Val Thr Lys Thr Arg Thr Gly Glu
  1               5                  10                  15

ccg cgc ccg gcc gaa acg ccc gcg atc atc gaa gcg cgc cgg acc atg       96
Pro Arg Pro Ala Glu Thr Pro Ala Ile Ile Glu Ala Arg Arg Thr Met
            20                  25                  30

gag gtt tgc aac gcc tgt cgc tat tgc gaa ggc tac tgc gcg gtc ttt      144
Glu Val Cys Asn Ala Cys Arg Tyr Cys Glu Gly Tyr Cys Ala Val Phe
        35                  40                  45

ccg gcc atg acc ctc aag cgg gag ttc gag gaa gcc gat ctc acc tac      192
```

-continued

```
Pro Ala Met Thr Leu Lys Arg Glu Phe Glu Glu Ala Asp Leu Thr Tyr
     50                  55                  60

ctg gcc aat ctc tgt cac tcg tgc cgc ggc tgt tac tac gct tgc caa      240
Leu Ala Asn Leu Cys His Ser Cys Arg Gly Cys Tyr Tyr Ala Cys Gln
 65                  70                  75                  80

tac gcg ccg ccc cat gag ttc ggg atc aac gtg ccc aag gtg ctg gcc      288
Tyr Ala Pro Pro His Glu Phe Gly Ile Asn Val Pro Lys Val Leu Ala
                 85                  90                  95

gag gtc cgc acc gaa agc tac cag gcc cat gcc tgg ccg cag gcc gtc      336
Glu Val Arg Thr Glu Ser Tyr Gln Ala His Ala Trp Pro Gln Ala Val
            100                 105                 110

gcc gtc gcc ttc gag cgt aac ggt ctg gtg gtg tcc ctg agc gct gca      384
Ala Val Ala Phe Glu Arg Asn Gly Leu Val Val Ser Leu Ser Ala Ala
        115                 120                 125

ctc gcg atc gtt gtc gtg ctg ctg gga acg gcc ttc ttc aat gga tcg      432
Leu Ala Ile Val Val Val Leu Leu Gly Thr Ala Phe Phe Asn Gly Ser
    130                 135                 140

gcg atg ttc cag gcg cac gcc tcg acg ccc ggc gca ggc ttc tac aag      480
Ala Met Phe Gln Ala His Ala Ser Thr Pro Gly Ala Gly Phe Tyr Lys
145                 150                 155                 160

gcc gtg ccc tat gcg gtc atg gtg agc gtc gcc ggc gcg atc ttc gcc      528
Ala Val Pro Tyr Ala Val Met Val Ser Val Ala Gly Ala Ile Phe Ala
                165                 170                 175

tat gcc gcc ttg gcg atg ttc atc ggc ctt atc cgg ttt tgg aag acc      576
Tyr Ala Ala Leu Ala Met Phe Ile Gly Leu Ile Arg Phe Trp Lys Thr
            180                 185                 190

gtg ggc ctt ggc ttg cgc gac gcc gtc gaa ccg cga acc ttg ttc cag      624
Val Gly Leu Gly Leu Arg Asp Ala Val Glu Pro Arg Thr Leu Phe Gln
        195                 200                 205

gcg ctg aag gat gcg gcg acc ctg cgc tat ctc ggc ggg ggc ggc gat      672
Ala Leu Lys Asp Ala Ala Thr Leu Arg Tyr Leu Gly Gly Gly Gly Asp
    210                 215                 220

ggc tgc aac gac gtc gac gct agc ttc tcg acc tca cgc cga cgt ttc      720
Gly Cys Asn Asp Val Asp Ala Ser Phe Ser Thr Ser Arg Arg Arg Phe
225                 230                 235                 240

cat cac gcc atg gcc tac ggc ttc ctg ctc tgt ttt gcc tcc acc tcc      768
His His Ala Met Ala Tyr Gly Phe Leu Leu Cys Phe Ala Ser Thr Ser
                245                 250                 255

acc ggt acg gtc tac gac cac ctc ctg ggc tgg ccc gcg ccc tat ccc      816
Thr Gly Thr Val Tyr Asp His Leu Leu Gly Trp Pro Ala Pro Tyr Pro
            260                 265                 270

ttc ttc agc ctg ccg gtg ctg ctg gga acg gtc ggc gga att ggg atc      864
Phe Phe Ser Leu Pro Val Leu Leu Gly Thr Val Gly Gly Ile Gly Ile
        275                 280                 285

gtc atc ggc acg ctc gga ctg ctc tgg ctg aag ctg gtc ggc gac cag      912
Val Ile Gly Thr Leu Gly Leu Leu Trp Leu Lys Leu Val Gly Asp Gln
    290                 295                 300

gag cct agg tcg aag gcg caa ttg ggc gcc gac acc gcg ctg ctg gtg      960
Glu Pro Arg Ser Lys Ala Gln Leu Gly Ala Asp Thr Ala Leu Leu Val
305                 310                 315                 320

ctg ctg ttc ctg atc agc gtg acg ggg ctg ttg ctg ctg gcg ctt cgg     1008
Leu Leu Phe Leu Ile Ser Val Thr Gly Leu Leu Leu Leu Ala Leu Arg
                325                 330                 335

acg acg gcg gcc atg ggc gtg atc ctg acc gtg cac ctt gga ctg gtc     1056
Thr Thr Ala Ala Met Gly Val Ile Leu Thr Val His Leu Gly Leu Val
            340                 345                 350

ttc tcg ttc ttc gcg acg atg ccg tac agc aag ttc gtg cac gga ctc     1104
Phe Ser Phe Phe Ala Thr Met Pro Tyr Ser Lys Phe Val His Gly Leu
        355                 360                 365
```

-continued

```
tat cga acc gtc gcc ttg gtt cgt tac gcc gtc gag cgc aag gcg ctg      1152
Tyr Arg Thr Val Ala Leu Val Arg Tyr Ala Val Glu Arg Lys Ala Leu
    370                 375                 380

gcc tcc ggg acg acg gag gaa gcg tct                                  1179
Ala Ser Gly Thr Thr Glu Glu Ala Ser
385                 390


<210> SEQ ID NO 29
<211> LENGTH: 393
<212> TYPE: PRT
<213> ORGANISM: Bacterium 2412.1

<400> SEQUENCE: 29

Met Gln His Asn Val Leu Asp Phe Val Thr Lys Thr Arg Thr Gly Glu
  1               5                  10                  15

Pro Arg Pro Ala Glu Thr Pro Ala Ile Ile Glu Ala Arg Arg Thr Met
             20                  25                  30

Glu Val Cys Asn Ala Cys Arg Tyr Cys Glu Gly Tyr Cys Ala Val Phe
         35                  40                  45

Pro Ala Met Thr Leu Lys Arg Glu Phe Glu Glu Ala Asp Leu Thr Tyr
     50                  55                  60

Leu Ala Asn Leu Cys His Ser Cys Arg Gly Cys Tyr Tyr Ala Cys Gln
 65                  70                  75                  80

Tyr Ala Pro Pro His Glu Phe Gly Ile Asn Val Pro Lys Val Leu Ala
                 85                  90                  95

Glu Val Arg Thr Glu Ser Tyr Gln Ala His Ala Trp Pro Gln Ala Val
            100                 105                 110

Ala Val Ala Phe Glu Arg Asn Gly Leu Val Val Ser Leu Ser Ala Ala
        115                 120                 125

Leu Ala Ile Val Val Val Leu Leu Gly Thr Ala Phe Phe Asn Gly Ser
    130                 135                 140

Ala Met Phe Gln Ala His Ala Ser Thr Pro Gly Ala Gly Phe Tyr Lys
145                 150                 155                 160

Ala Val Pro Tyr Ala Val Met Val Ser Val Ala Gly Ala Ile Phe Ala
                165                 170                 175

Tyr Ala Ala Leu Ala Met Phe Ile Gly Leu Ile Arg Phe Trp Lys Thr
            180                 185                 190

Val Gly Leu Gly Leu Arg Asp Ala Val Glu Pro Arg Thr Leu Phe Gln
        195                 200                 205

Ala Leu Lys Asp Ala Ala Thr Leu Arg Tyr Leu Gly Gly Gly Gly Asp
    210                 215                 220

Gly Cys Asn Asp Val Asp Ala Ser Phe Ser Thr Ser Arg Arg Arg Phe
225                 230                 235                 240

His His Ala Met Ala Tyr Gly Phe Leu Leu Cys Phe Ala Ser Thr Ser
                245                 250                 255

Thr Gly Thr Val Tyr Asp His Leu Leu Gly Trp Pro Ala Pro Tyr Pro
            260                 265                 270

Phe Phe Ser Leu Pro Val Leu Leu Gly Thr Val Gly Gly Ile Gly Ile
        275                 280                 285

Val Ile Gly Thr Leu Gly Leu Leu Trp Leu Lys Leu Val Gly Asp Gln
    290                 295                 300

Glu Pro Arg Ser Lys Ala Gln Leu Gly Ala Asp Thr Ala Leu Leu Val
305                 310                 315                 320

Leu Leu Phe Leu Ile Ser Val Thr Gly Leu Leu Leu Leu Ala Leu Arg
                325                 330                 335
```

-continued

```
Thr Thr Ala Ala Met Gly Val Ile Leu Thr Val His Leu Gly Leu Val
            340                 345                 350

Phe Ser Phe Phe Ala Thr Met Pro Tyr Ser Lys Phe Val His Gly Leu
        355                 360                 365

Tyr Arg Thr Val Ala Leu Val Arg Tyr Ala Val Glu Arg Lys Ala Leu
    370                 375                 380

Ala Ser Gly Thr Thr Glu Glu Ala Ser
385                 390


<210> SEQ ID NO 30
<211> LENGTH: 477
<212> TYPE: DNA
<213> ORGANISM: Bacterium 2412.1
<220> FEATURE:
<223> OTHER INFORMATION: fccO Regulatory protein
<221> NAME/KEY: CDS
<222> LOCATION: ()..(477)

<400> SEQUENCE: 30

atg gcc gcg gcg aac acc ctg gga gcg act tcc ttg ggg tcg acg tca       48
Met Ala Ala Ala Asn Thr Leu Gly Ala Thr Ser Leu Gly Ser Thr Ser
  1               5                  10                  15

tcc agg acg atc aga gcg tcg ttt ccg ccc aac tca agc gat ata cgt       96
Ser Arg Thr Ile Arg Ala Ser Phe Pro Pro Asn Ser Ser Asp Ile Arg
             20                  25                  30

ttg agg cct tcg gcc gcg ccg gcc atg acc ttt ttt ccg gtc tgg gtc      144
Leu Arg Pro Ser Ala Ala Pro Ala Met Thr Phe Phe Pro Val Trp Val
         35                  40                  45

gat ccg gtg aag ctg att ttg cga atg cca gga tgg cgg gtc att tcc      192
Asp Pro Val Lys Leu Ile Leu Arg Met Pro Gly Trp Arg Val Ile Ser
     50                  55                  60

gcg ccg aga tcg tcg gcg tcg gtg atg atg tta atg acg ccc ggt ggg      240
Ala Pro Arg Ser Ser Ala Ser Val Met Met Leu Met Thr Pro Gly Gly
 65                  70                  75                  80

acg ata tcc ttg acc aag gcg cca aac cga agc gcc gtc aga ggc gtc      288
Thr Ile Ser Leu Thr Lys Ala Pro Asn Arg Ser Ala Val Arg Gly Val
                 85                  90                  95

gtc gcc gcc ggc ttg agg atg acc gtg ttg ccg gcc agc agg gcc gcc      336
Val Ala Ala Gly Leu Arg Met Thr Val Leu Pro Ala Ser Arg Ala Ala
            100                 105                 110

ggg atc ttg aac gcc atc aac agc atc ggg aaa ttc cag ggg acg atg      384
Gly Ile Leu Asn Ala Ile Asn Ser Ile Gly Lys Phe Gln Gly Thr Met
        115                 120                 125

cag ccc acc acg cct agg ggg cgt cta tgc acc tct acg cgg ccc gtc      432
Gln Pro Thr Thr Pro Arg Gly Arg Leu Cys Thr Ser Thr Arg Pro Val
    130                 135                 140

gcg tcg tct ctg acc acg cga ggc ggc aga tcg agc gag gtg aag          477
Ala Ser Ser Leu Thr Thr Arg Gly Gly Arg Ser Ser Glu Val Lys
145                 150                 155


<210> SEQ ID NO 31
<211> LENGTH: 159
<212> TYPE: PRT
<213> ORGANISM: Bacterium 2412.1

<400> SEQUENCE: 31

Met Ala Ala Ala Asn Thr Leu Gly Ala Thr Ser Leu Gly Ser Thr Ser
  1               5                  10                  15

Ser Arg Thr Ile Arg Ala Ser Phe Pro Pro Asn Ser Ser Asp Ile Arg
             20                  25                  30

Leu Arg Pro Ser Ala Ala Pro Ala Met Thr Phe Phe Pro Val Trp Val
```

-continued

```
        35                  40                  45

Asp Pro Val Lys Leu Ile Leu Arg Met Pro Gly Trp Arg Val Ile Ser
     50                  55                  60

Ala Pro Arg Ser Ser Ala Ser Val Met Met Leu Met Thr Pro Gly Gly
 65                  70                  75                  80

Thr Ile Ser Leu Thr Lys Ala Pro Asn Arg Ser Ala Val Arg Gly Val
                 85                  90                  95

Val Ala Ala Gly Leu Arg Met Thr Val Leu Pro Ala Ser Arg Ala Ala
            100                 105                 110

Gly Ile Leu Asn Ala Ile Asn Ser Ile Gly Lys Phe Gln Gly Thr Met
        115                 120                 125

Gln Pro Thr Thr Pro Arg Gly Arg Leu Cys Thr Ser Thr Arg Pro Val
    130                 135                 140

Ala Ser Ser Leu Thr Thr Arg Gly Gly Arg Ser Ser Glu Val Lys
145                 150                 155


<210> SEQ ID NO 32
<211> LENGTH: 1056
<212> TYPE: DNA
<213> ORGANISM: Bacterium 2412.1
<220> FEATURE:
<223> OTHER INFORMATION: fccP
<221> NAME/KEY: CDS
<222> LOCATION: ()..(1056)

<400> SEQUENCE: 32

atg gcg gcg cct cct tct gcg cgc cta gag atg cag gtt gaa ttg cac       48
Met Ala Ala Pro Pro Ser Ala Arg Leu Glu Met Gln Val Glu Leu His
  1               5                  10                  15

gct gta ggt ccg cgg cgc ggc cac gac gcc gtt gat gaa gcc gaa cgt       96
Ala Val Gly Pro Arg Arg Gly His Asp Ala Val Asp Glu Ala Glu Arg
             20                  25                  30

cgc ccc ctc gtc gaa cag ata gtt gta gta ctt cgt gcc cgt cag gtt      144
Arg Pro Leu Val Glu Gln Ile Val Val Val Leu Arg Ala Arg Gln Val
         35                  40                  45

tcg gac att gaa ccc gac atc cca gtg gtt tct gga gtt gaa ggt cag      192
Ser Asp Ile Glu Pro Asp Ile Pro Val Val Ser Gly Val Glu Gly Gln
     50                  55                  60

gct ggc gtt gtg cac cca gta gcc ctc ctg ctg ggt ata ggg ggc gtt      240
Ala Gly Val Val His Pro Val Ala Leu Leu Leu Gly Ile Gly Gly Val
 65                  70                  75                  80

cgt cga atc gaa gaa ctg gtg cga ctt gta ggc cga ggt gaa ggc gac      288
Arg Arg Ile Glu Glu Leu Val Arg Leu Val Gly Arg Gly Glu Gly Asp
                 85                  90                  95

gtt gac gct gtc gtc gtc ggc aag atg gaa ggt gta gtc cgc cgc ggc      336
Val Asp Ala Val Val Val Gly Lys Met Glu Gly Val Val Arg Arg Gly
            100                 105                 110

gta gag cga gaa ctt cgg cgc att ggc cag ttg ctt gcc ttc cag cga      384
Val Glu Arg Glu Leu Arg Arg Ile Gly Gln Leu Leu Ala Phe Gln Arg
        115                 120                 125

cgt tcc ccc gga gaa gcc cgc ctc gtc cag ccg cgt tcg cag cca ggc      432
Arg Ser Pro Gly Glu Ala Arg Leu Val Gln Pro Arg Ser Gln Pro Gly
    130                 135                 140

cgg ctg cag gct gag gac gag atc cgg gat cgg gac ggc ctt tac ttc      480
Arg Leu Gln Ala Glu Asp Glu Ile Arg Asp Arg Asp Gly Leu Tyr Phe
145                 150                 155                 160

caa ttc cac gcc ctg gga gtg ggc ctt tcg ggc gtt ggt cag gac gtt      528
Gln Phe His Ala Leu Gly Val Gly Leu Ser Gly Val Gly Gln Asp Val
                165                 170                 175
```

-continued

```
cgt cgt cac ggt aac agg gcc ggt cac ggt atc cac gac gac ggc cgt      576
Arg Arg His Gly Asn Arg Ala Gly His Gly Ile His Asp Asp Gly Arg
            180                 185                 190

gtt ggc cag gat ctg ctc gtt gtc gta gct gtt gta gaa agc cgc gcc      624
Val Gly Gln Asp Leu Leu Val Val Val Ala Val Val Glu Ser Arg Ala
        195                 200                 205

gtt gac cac cag gcg acg ctc gaa cag gct cga ctt gaa gcc cag ttc      672
Val Asp His Gln Ala Thr Leu Glu Gln Ala Arg Leu Glu Ala Gln Phe
    210                 215                 220

gta ggt ggt cac ctt ctc cgg tgc gac ggg ttt gac cgc ggc gag ggc      720
Val Gly Gly His Leu Leu Arg Cys Asp Gly Phe Asp Arg Gly Glu Gly
225                 230                 235                 240

ttt gtt ggg gtt gct gct cag gaa ccc gcc gtt gaa ggc gcc gcc ctt      768
Phe Val Gly Val Ala Ala Gln Glu Pro Ala Val Glu Gly Ala Ala Leu
                245                 250                 255

aaa gcc ggt ggc gac gct gcc gta gac cat aac acg ctc ggc ggg acg      816
Lys Ala Gly Gly Asp Ala Ala Val Asp His Asn Thr Leu Gly Gly Thr
            260                 265                 270

gta gga aag cgc ggc gcg cca ggt cgg atc gga agc ctt gaa cgc ttc      864
Val Gly Lys Arg Gly Ala Pro Gly Arg Ile Gly Ser Leu Glu Arg Phe
        275                 280                 285

gct cag cga gac gat ctt gcc gag agg acc gta ttt ccc aag gcc tcc      912
Ala Gln Arg Asp Asp Leu Ala Glu Arg Thr Val Phe Pro Lys Ala Ser
    290                 295                 300

tgc ttg gac ctg ggt cgc gct gaa gtg atc gaa cgt ctt gcg ttc atg      960
Cys Leu Asp Leu Gly Arg Ala Glu Val Ile Glu Arg Leu Ala Phe Met
305                 310                 315                 320

ggt gta acg acc gcc caa ggt cag ggt gaa ccg gtc caa ggt ata gtc     1008
Gly Val Thr Thr Ala Gln Gly Gln Gly Glu Pro Val Gln Gly Ile Val
                325                 330                 335

ggc ttg gcc gaa ggc ggc tat cga ccg tgt ttt ctg agt gtt ttg gct     1056
Gly Leu Ala Glu Gly Gly Tyr Arg Pro Cys Phe Leu Ser Val Leu Ala
            340                 345                 350


<210> SEQ ID NO 33
<211> LENGTH: 352
<212> TYPE: PRT
<213> ORGANISM: Bacterium 2412.1

<400> SEQUENCE: 33

Met Ala Ala Pro Pro Ser Ala Arg Leu Glu Met Gln Val Glu Leu His
  1               5                  10                  15

Ala Val Gly Pro Arg Arg Gly His Asp Ala Val Asp Glu Ala Glu Arg
             20                  25                  30

Arg Pro Leu Val Glu Gln Ile Val Val Val Leu Arg Ala Arg Gln Val
         35                  40                  45

Ser Asp Ile Glu Pro Asp Ile Pro Val Val Ser Gly Val Glu Gly Gln
     50                  55                  60

Ala Gly Val Val His Pro Val Ala Leu Leu Leu Gly Ile Gly Gly Val
 65                  70                  75                  80

Arg Arg Ile Glu Glu Leu Val Arg Leu Val Gly Arg Gly Glu Gly Asp
                 85                  90                  95

Val Asp Ala Val Val Val Gly Lys Met Glu Gly Val Val Arg Arg Gly
            100                 105                 110

Val Glu Arg Glu Leu Arg Arg Ile Gly Gln Leu Leu Ala Phe Gln Arg
        115                 120                 125

Arg Ser Pro Gly Glu Ala Arg Leu Val Gln Pro Arg Ser Gln Pro Gly
    130                 135                 140
```

-continued

```
Arg Leu Gln Ala Glu Asp Glu Ile Arg Asp Arg Asp Gly Leu Tyr Phe
145                 150                 155                 160

Gln Phe His Ala Leu Gly Val Gly Leu Ser Gly Val Gly Gln Asp Val
                165                 170                 175

Arg Arg His Gly Asn Arg Ala Gly His Gly Ile His Asp Asp Gly Arg
            180                 185                 190

Val Gly Gln Asp Leu Leu Val Val Val Ala Val Val Glu Ser Arg Ala
        195                 200                 205

Val Asp His Gln Ala Thr Leu Glu Gln Ala Arg Leu Glu Ala Gln Phe
    210                 215                 220

Val Gly Gly His Leu Leu Arg Cys Asp Gly Phe Asp Arg Gly Glu Gly
225                 230                 235                 240

Phe Val Gly Val Ala Ala Gln Glu Pro Ala Val Glu Gly Ala Ala Leu
                245                 250                 255

Lys Ala Gly Gly Asp Ala Ala Val Asp His Asn Thr Leu Gly Gly Thr
            260                 265                 270

Val Gly Lys Arg Gly Ala Pro Gly Arg Ile Gly Ser Leu Glu Arg Phe
        275                 280                 285

Ala Gln Arg Asp Asp Leu Ala Glu Arg Thr Val Phe Pro Lys Ala Ser
    290                 295                 300

Cys Leu Asp Leu Gly Arg Ala Glu Val Ile Glu Arg Leu Ala Phe Met
305                 310                 315                 320

Gly Val Thr Thr Ala Gln Gly Gln Gly Glu Pro Val Gln Gly Ile Val
                325                 330                 335

Gly Leu Ala Glu Gly Gly Tyr Arg Pro Cys Phe Leu Ser Val Leu Ala
            340                 345                 350


<210> SEQ ID NO 34
<211> LENGTH: 477
<212> TYPE: DNA
<213> ORGANISM: Bacterium 2412.1
<220> FEATURE:
<223> OTHER INFORMATION: fccQ Leucine Regulatory Protein Homolog
<221> NAME/KEY: CDS
<222> LOCATION: ()..(477)

<400> SEQUENCE: 34

atg ctg agg tta cgc cac atg atg cca gcg ctg gac gcg atc gac cgc       48
Met Leu Arg Leu Arg His Met Met Pro Ala Leu Asp Ala Ile Asp Arg
  1               5                  10                  15

aag atc att ggc ctg ctt cgg gtc aat ggc cgc atg ccc aac aat gag       96
Lys Ile Ile Gly Leu Leu Arg Val Asn Gly Arg Met Pro Asn Asn Glu
             20                  25                  30

ttg gcg cag aag gta ggg ctt tcg cct tcc gcc tgt ctg cga cgc gtc      144
Leu Ala Gln Lys Val Gly Leu Ser Pro Ser Ala Cys Leu Arg Arg Val
         35                  40                  45

aag ttg ctc gag tcg aac ggg gtg atc cga ggg tat tgt gca ttg gtt      192
Lys Leu Leu Glu Ser Asn Gly Val Ile Arg Gly Tyr Cys Ala Leu Val
     50                  55                  60

gcc gag cag tcg ttg gac gcc agc gtg gtg gcg atc gtc cgg ata acc      240
Ala Glu Gln Ser Leu Asp Ala Ser Val Val Ala Ile Val Arg Ile Thr
 65                  70                  75                  80

ttg gac aag cag acc gag gac tat ctg aat cgg ttc gag gag gcc gtt      288
Leu Asp Lys Gln Thr Glu Asp Tyr Leu Asn Arg Phe Glu Glu Ala Val
                 85                  90                  95

cgg cgg cat ccc gag atc gct gag tgc ttt ctg atg acc ggc gac gca      336
Arg Arg His Pro Glu Ile Ala Glu Cys Phe Leu Met Thr Gly Asp Ala
            100                 105                 110
```

-continued

```
gac tac atc ctt cgg gct acc gcg ccg agc acg gcc gcc tac gag caa      384
Asp Tyr Ile Leu Arg Ala Thr Ala Pro Ser Thr Ala Ala Tyr Glu Gln
        115                 120                 125

atc cac aag gaa gtc ctt tct cgg ctt ccc ggg gtg gcg cgc atc cat      432
Ile His Lys Glu Val Leu Ser Arg Leu Pro Gly Val Ala Arg Ile His
    130                 135                 140

tcg agc ttc gcc atc cgc agc gtg ctg tcg tcg gtc gca agg ccc          477
Ser Ser Phe Ala Ile Arg Ser Val Leu Ser Ser Val Ala Arg Pro
145                 150                 155


<210> SEQ ID NO 35
<211> LENGTH: 159
<212> TYPE: PRT
<213> ORGANISM: Bacterium 2412.1

<400> SEQUENCE: 35

Met Leu Arg Leu Arg His Met Met Pro Ala Leu Asp Ala Ile Asp Arg
  1               5                  10                  15

Lys Ile Ile Gly Leu Leu Arg Val Asn Gly Arg Met Pro Asn Asn Glu
             20                  25                  30

Leu Ala Gln Lys Val Gly Leu Ser Pro Ser Ala Cys Leu Arg Arg Val
        35                  40                  45

Lys Leu Leu Glu Ser Asn Gly Val Ile Arg Gly Tyr Cys Ala Leu Val
     50                  55                  60

Ala Glu Gln Ser Leu Asp Ala Ser Val Val Ala Ile Val Arg Ile Thr
 65                  70                  75                  80

Leu Asp Lys Gln Thr Glu Asp Tyr Leu Asn Arg Phe Glu Glu Ala Val
                 85                  90                  95

Arg Arg His Pro Glu Ile Ala Glu Cys Phe Leu Met Thr Gly Asp Ala
            100                 105                 110

Asp Tyr Ile Leu Arg Ala Thr Ala Pro Ser Thr Ala Ala Tyr Glu Gln
        115                 120                 125

Ile His Lys Glu Val Leu Ser Arg Leu Pro Gly Val Ala Arg Ile His
    130                 135                 140

Ser Ser Phe Ala Ile Arg Ser Val Leu Ser Ser Val Ala Arg Pro
145                 150                 155


<210> SEQ ID NO 36
<211> LENGTH: 1074
<212> TYPE: DNA
<213> ORGANISM: Bacterium 2412.1
<220> FEATURE:
<223> OTHER INFORMATION: fccR
<221> NAME/KEY: CDS
<222> LOCATION: (1)..(1074)

<400> SEQUENCE: 36

atg gcg gct gac gag atc tcc cag ctc agg aga acc cat ccc cac cgt       48
Met Ala Ala Asp Glu Ile Ser Gln Leu Arg Arg Thr His Pro His Arg
  1               5                  10                  15

ctt gat gac tcc ctg gag gcg gtc gct gat ctg cag gta gcc ctc cgc       96
Leu Asp Asp Ser Leu Glu Ala Val Ala Asp Leu Gln Val Ala Leu Arg
             20                  25                  30

gtc aat ccg gcc gaa atc ctg cgt atg aag gct tcc tcc gcg cca aag      144
Val Asn Pro Ala Glu Ile Leu Arg Met Lys Ala Ser Ser Ala Pro Lys
        35                  40                  45

ctc gcg cga ggc ggc cag atc gcg atg gta ccc agc cgt cag cca agg      192
Leu Ala Arg Gly Gly Gln Ile Ala Met Val Pro Ser Arg Gln Pro Arg
     50                  55                  60

cgc acg caa cac gat ctc gcc cgc gga gag gcc gtc gcg ggg cac atc      240
```

-continued

```
Arg Thr Gln His Asp Leu Ala Arg Gly Glu Ala Val Ala Gly His Ile
 65                  70                  75                  80

cgc cat gga ctc atc cac gac ccg gag gtc gac cag cgc gat agc ttg      288
Arg His Gly Leu Ile His Asp Pro Glu Val Asp Gln Arg Asp Ser Leu
                 85                  90                  95

tcc gac ctt ggt gcg aat ggc gac ctc ctc ctg agc tgg agc cat tgc      336
Ser Asp Leu Gly Ala Asn Gly Asp Leu Leu Leu Ser Trp Ser His Cys
            100                 105                 110

ttc ggt cct aat gcg cgt gaa gct gac cag cgg ccc ggt ttc gga cat      384
Phe Gly Pro Asn Ala Arg Glu Ala Asp Gln Arg Pro Gly Phe Gly His
        115                 120                 125

tcc gta tcc ggt ggt cag gac gat gcc gcg ccc cgc ggc ctg aag agc      432
Ser Val Ser Gly Gly Gln Asp Asp Ala Ala Pro Arg Gly Leu Lys Ser
    130                 135                 140

cag gcc gcg ggg cag cgc cgc tcc gcc gac gag cac ctg cca tcc ggt      480
Gln Ala Ala Gly Gln Arg Arg Ser Ala Asp Glu His Leu Pro Ser Gly
145                 150                 155                 160

gaa atc cgc cgt ctg gcc cga agg cga att gag cat cat ctg caa aag      528
Glu Ile Arg Arg Leu Ala Arg Arg Arg Ile Glu His His Leu Gln Lys
                165                 170                 175

tgt ggg cac gca atg aga gaa ggt cac ctt ctc cgc gcg ctg aag ctc      576
Cys Gly His Ala Met Arg Glu Gly His Leu Leu Arg Ala Leu Lys Leu
            180                 185                 190

cac cag ttg ctc ggg aac ata gcg ccc tgg gta gac ttg ctt gca gcc      624
His Gln Leu Leu Gly Asn Ile Ala Pro Trp Val Asp Leu Leu Ala Ala
        195                 200                 205

gac cat cgt cgc cac gaa ggg cat tcc cca cgc atg agc atg gaa cat      672
Asp His Arg Arg His Glu Gly His Ser Pro Arg Met Ser Met Glu His
    210                 215                 220

cgg ggt gat cgg cat gta gac cgt atc gcg ccc cag cct ggc gta acc      720
Arg Gly Asp Arg His Val Asp Arg Ile Ala Pro Gln Pro Gly Val Thr
225                 230                 235                 240

gtc tcc aag ggc cag cgt cgc cat cac cgc cag ggt gtg cag cac cag      768
Val Ser Lys Gly Gln Arg Arg His His Arg Gln Gly Val Gln His Gln
                245                 250                 255

ctg acg atg cga ata gta gac gcc ctt cgg acg ccc ggt cgt gcc gct      816
Leu Thr Met Arg Ile Val Asp Ala Leu Arg Thr Pro Gly Arg Ala Ala
            260                 265                 270

ggt gta gaa ggt cgt cgc ccg cgt gtt ctc gtc gaa gtc cgg gaa gtc      864
Gly Val Glu Gly Arg Arg Pro Arg Val Leu Val Glu Val Arg Glu Val
        275                 280                 285

gaa ccg agg gcg cgc ggc cgc cat cag ggc ctc ata ctc ccc cag cac      912
Glu Pro Arg Ala Arg Gly Arg His Gln Gly Leu Ile Leu Pro Gln His
    290                 295                 300

cca ggg atg ggc ggc ttc cgc ctc gtc gtc ctt cag atg gac gac ccc      960
Pro Gly Met Gly Gly Phe Arg Leu Val Val Leu Gln Met Asp Asp Pro
305                 310                 315                 320

gcg cag gct ggg caa ttg gtc gat cac ctc ctc gag gat cgg cag gaa     1008
Ala Gln Ala Gly Gln Leu Val Asp His Leu Leu Glu Asp Arg Gln Glu
                325                 330                 335

atc ggt gtg gct cag cgc cag ggt ggc gcc cgc atg ctc gag cgt gta     1056
Ile Gly Val Ala Gln Arg Gln Gly Gly Ala Arg Met Leu Glu Arg Val
            340                 345                 350

gcg cag gtc gtc tcg ggc                                             1074
Ala Gln Val Val Ser Gly
        355
```

<210> SEQ ID NO 37
<211> LENGTH: 358
<212> TYPE: PRT

-continued

<213> ORGANISM: Bacterium 2412.1

<400> SEQUENCE: 37

```
Met Ala Ala Asp Glu Ile Ser Gln Leu Arg Arg Thr His Pro His Arg
  1               5                  10                  15

Leu Asp Asp Ser Leu Glu Ala Val Ala Asp Leu Gln Val Ala Leu Arg
             20                  25                  30

Val Asn Pro Ala Glu Ile Leu Arg Met Lys Ala Ser Ser Ala Pro Lys
         35                  40                  45

Leu Ala Arg Gly Gly Gln Ile Ala Met Val Pro Ser Arg Gln Pro Arg
     50                  55                  60

Arg Thr Gln His Asp Leu Ala Arg Gly Glu Ala Val Ala Gly His Ile
 65                  70                  75                  80

Arg His Gly Leu Ile His Asp Pro Glu Val Asp Gln Arg Asp Ser Leu
                 85                  90                  95

Ser Asp Leu Gly Ala Asn Gly Asp Leu Leu Leu Ser Trp Ser His Cys
            100                 105                 110

Phe Gly Pro Asn Ala Arg Glu Ala Asp Gln Arg Pro Gly Phe Gly His
        115                 120                 125

Ser Val Ser Gly Gly Gln Asp Asp Ala Ala Pro Arg Gly Leu Lys Ser
    130                 135                 140

Gln Ala Ala Gly Gln Arg Arg Ser Ala Asp Glu His Leu Pro Ser Gly
145                 150                 155                 160

Glu Ile Arg Arg Leu Ala Arg Arg Arg Ile Glu His His Leu Gln Lys
                165                 170                 175

Cys Gly His Ala Met Arg Glu Gly His Leu Leu Arg Ala Leu Lys Leu
            180                 185                 190

His Gln Leu Leu Gly Asn Ile Ala Pro Trp Val Asp Leu Leu Ala Ala
        195                 200                 205

Asp His Arg Arg His Glu Gly His Ser Pro Arg Met Ser Met Glu His
    210                 215                 220

Arg Gly Asp Arg His Val Asp Arg Ile Ala Pro Gln Pro Gly Val Thr
225                 230                 235                 240

Val Ser Lys Gly Gln Arg Arg His His Arg Gln Gly Val Gln His Gln
                245                 250                 255

Leu Thr Met Arg Ile Val Asp Ala Leu Arg Thr Pro Gly Arg Ala Ala
            260                 265                 270

Gly Val Glu Gly Arg Arg Pro Arg Val Leu Val Glu Val Arg Glu Val
        275                 280                 285

Glu Pro Arg Ala Arg Gly Arg His Gln Gly Leu Ile Leu Pro Gln His
    290                 295                 300

Pro Gly Met Gly Gly Phe Arg Leu Val Val Leu Gln Met Asp Asp Pro
305                 310                 315                 320

Ala Gln Ala Gly Gln Leu Val Asp His Leu Leu Glu Asp Arg Gln Glu
                325                 330                 335

Ile Gly Val Ala Gln Arg Gln Gly Gly Ala Arg Met Leu Glu Arg Val
            340                 345                 350

Ala Gln Val Val Ser Gly
        355
```

<210> SEQ ID NO 38
<211> LENGTH: 552
<212> TYPE: DNA
<213> ORGANISM: Bacterium 2412.1
<220> FEATURE:

-continued

<223> OTHER INFORMATION: fccS
<221> NAME/KEY: CDS
<222> LOCATION: (1)..(552)

<400> SEQUENCE: 38

```
atg cag gcg ctg gcc gga ata ggc ggc gcg gaa ctc ttg ggt cca ggt       48
Met Gln Ala Leu Ala Gly Ile Gly Gly Ala Glu Leu Leu Gly Pro Gly
  1               5                  10                  15

gtc gga gcg aac gcc gta ggt cgc gtg gag cag act gtc aga cgt ccc       96
Val Gly Ala Asn Ala Val Gly Arg Val Glu Gln Thr Val Arg Arg Pro
             20                  25                  30

gtc ggc gtc gtc ggg gcc gct ctt ttt gct gtg cgt gaa ggc gct gat      144
Val Gly Val Val Gly Ala Ala Leu Phe Ala Val Arg Glu Gly Ala Asp
         35                  40                  45

cga tgt cag ggt cac cgg acc gac ctc ata gtc ggc gcg ggc ctg ctg      192
Arg Cys Gln Gly His Arg Thr Asp Leu Ile Val Gly Ala Gly Leu Leu
     50                  55                  60

cag gaa gtt ttc cac gcg caa gcg ttc acc gcg atc gct gga acc gtc      240
Gln Glu Val Phe His Ala Gln Ala Phe Thr Ala Ile Ala Gly Thr Val
 65                  70                  75                  80

gta gaa gcc gct cgg cgt gcc tgc gcc gaa cac gtt gac gca acc tcc      288
Val Glu Ala Ala Arg Arg Ala Cys Ala Glu His Val Asp Ala Thr Ser
                 85                  90                  95

ggc gcg gac ctg ctc ggg gct gca gag agt cgg gct ggc gct gga ttg      336
Gly Ala Asp Leu Leu Gly Ala Ala Glu Ser Arg Ala Gly Ala Gly Leu
            100                 105                 110

ggt tcc tgc cgc gaa ggc gcc caa gtg tcg gta ctg gac gat cgg cga      384
Gly Ser Cys Arg Glu Gly Ala Gln Val Ser Val Leu Asp Asp Arg Arg
        115                 120                 125

gtt gac atg acc ata ggc cga act gag aag tac ttt cag cct gtc att      432
Val Asp Met Thr Ile Gly Arg Thr Glu Lys Tyr Phe Gln Pro Val Ile
    130                 135                 140

agg tcg gta gag cag ttg cag cct gac ggc ctg att gtc cgt gcc cga      480
Arg Ser Val Glu Gln Leu Gln Pro Asp Gly Leu Ile Val Arg Ala Arg
145                 150                 155                 160

cgc cga acc gcc cgt cag cgt gtt gtg cat gaa ccc gtc gga gtg gtt      528
Arg Arg Thr Ala Arg Gln Arg Val Val His Glu Pro Val Gly Val Val
                165                 170                 175

gac gac gaa ggc cag gcg ggc gct                                      552
Asp Asp Glu Gly Gln Ala Gly Ala
            180
```

<210> SEQ ID NO 39
<211> LENGTH: 184
<212> TYPE: PRT
<213> ORGANISM: Bacterium 2412.1

<400> SEQUENCE: 39

```
Met Gln Ala Leu Ala Gly Ile Gly Gly Ala Glu Leu Leu Gly Pro Gly
  1               5                  10                  15

Val Gly Ala Asn Ala Val Gly Arg Val Glu Gln Thr Val Arg Arg Pro
             20                  25                  30

Val Gly Val Val Gly Ala Ala Leu Phe Ala Val Arg Glu Gly Ala Asp
         35                  40                  45

Arg Cys Gln Gly His Arg Thr Asp Leu Ile Val Gly Ala Gly Leu Leu
     50                  55                  60

Gln Glu Val Phe His Ala Gln Ala Phe Thr Ala Ile Ala Gly Thr Val
 65                  70                  75                  80

Val Glu Ala Ala Arg Arg Ala Cys Ala Glu His Val Asp Ala Thr Ser
                 85                  90                  95
```

-continued

```
Gly Ala Asp Leu Leu Gly Ala Ala Glu Ser Arg Ala Gly Ala Gly Leu
            100                 105                 110

Gly Ser Cys Arg Glu Gly Ala Gln Val Ser Val Leu Asp Asp Arg Arg
        115                 120                 125

Val Asp Met Thr Ile Gly Arg Thr Glu Lys Tyr Phe Gln Pro Val Ile
    130                 135                 140

Arg Ser Val Glu Gln Leu Gln Pro Asp Gly Leu Ile Val Arg Ala Arg
145                 150                 155                 160

Arg Arg Thr Ala Arg Gln Arg Val Val His Glu Pro Val Gly Val Val
                165                 170                 175

Asp Asp Glu Gly Gln Ala Gly Ala
            180


<210> SEQ ID NO 40
<211> LENGTH: 531
<212> TYPE: DNA
<213> ORGANISM: Bacterium 2412.1
<220> FEATURE:
<223> OTHER INFORMATION: fccT
<221> NAME/KEY: CDS
<222> LOCATION: ()..(531)

<400> SEQUENCE: 40

atg ggc gtc cgc ggc gaa gtc ttg gct cgg cgc tct gga cgt gaa cac       48
Met Gly Val Arg Gly Glu Val Leu Ala Arg Arg Ser Gly Arg Glu His
  1               5                  10                  15

caa ggc ccc acc gct gga gtt gcg ccc ata gag cgt acc ttg cgg tcc       96
Gln Gly Pro Thr Ala Gly Val Ala Pro Ile Glu Arg Thr Leu Arg Ser
             20                  25                  30

ttt gag aac ctg gat ctg gtt gat gtc gaa gat tcc gaa ggt ctg ggc      144
Phe Glu Asn Leu Asp Leu Val Asp Val Glu Asp Ser Glu Gly Leu Gly
         35                  40                  45

cga cgg ggc gct gat ata gac atc gtc gac ata gat cgc gtt cgg gcc      192
Arg Arg Gly Ala Asp Ile Asp Ile Val Asp Ile Asp Arg Val Arg Ala
     50                  55                  60

ggc gtt gtt gga att gaa gtc gtt gag gcc gat gcc gcg gat cgt cac      240
Gly Val Val Gly Ile Glu Val Val Glu Ala Asp Ala Ala Asp Arg His
 65                  70                  75                  80

cgc cgg ctg gtt gcc ttc gcc gtt ggg cat ggc gat ggt gac gtt ggg      288
Arg Arg Leu Val Ala Phe Ala Val Gly His Gly Asp Gly Asp Val Gly
                 85                  90                  95

cgt cac tcg ggc gat atc gct ggt ctg ttt gat ccc ttc gcg ctc gag      336
Arg His Ser Gly Asp Ile Ala Gly Leu Phe Asp Pro Phe Ala Leu Glu
            100                 105                 110

ctg cgc tgc cga cag cgc ctg cac cga gac cgg cac att ctg aat gtt      384
Leu Arg Cys Arg Gln Arg Leu His Arg Asp Arg His Ile Leu Asn Val
        115                 120                 125

ctc gct gcg gcg ctg cgc ggt gac gac gat ctc ctg cac ctc ctg cga      432
Leu Ala Ala Ala Leu Arg Gly Asp Asp Asp Leu Leu His Leu Leu Arg
    130                 135                 140

cgc ctc gtg acc agc cgg cgg aac cgc cac ctg cgc gag cgc ctt ggg      480
Arg Leu Val Thr Ser Arg Arg Asn Arg His Leu Arg Glu Arg Leu Gly
145                 150                 155                 160

cgc aag acc cag cac cag ggc gct gcc ggc cgc cgt cag cat gag cct      528
Arg Lys Thr Gln His Gln Gly Ala Ala Gly Arg Arg Gln His Glu Pro
                165                 170                 175

tcg                                                                  531
Ser
```

-continued

<210> SEQ ID NO 41
<211> LENGTH: 177
<212> TYPE: PRT
<213> ORGANISM: Bacterium 2412.1

<400> SEQUENCE: 41

```
Met Gly Val Arg Gly Glu Val Leu Ala Arg Arg Ser Gly Arg Glu His
  1               5                  10                  15

Gln Gly Pro Thr Ala Gly Val Ala Pro Ile Glu Arg Thr Leu Arg Ser
             20                  25                  30

Phe Glu Asn Leu Asp Leu Val Asp Val Glu Asp Ser Glu Gly Leu Gly
         35                  40                  45

Arg Arg Gly Ala Asp Ile Asp Ile Val Asp Ile Asp Arg Val Arg Ala
     50                  55                  60

Gly Val Val Gly Ile Glu Val Val Glu Ala Asp Ala Ala Asp Arg His
 65                  70                  75                  80

Arg Arg Leu Val Ala Phe Ala Val Gly His Gly Asp Gly Asp Val Gly
                 85                  90                  95

Arg His Ser Gly Asp Ile Ala Gly Leu Phe Asp Pro Phe Ala Leu Glu
            100                 105                 110

Leu Arg Cys Arg Gln Arg Leu His Arg Asp Arg His Ile Leu Asn Val
        115                 120                 125

Leu Ala Ala Ala Leu Arg Gly Asp Asp Asp Leu Leu His Leu Leu Arg
    130                 135                 140

Arg Leu Val Thr Ser Arg Arg Asn Arg His Leu Arg Glu Arg Leu Gly
145                 150                 155                 160

Arg Lys Thr Gln His Gln Gly Ala Ala Gly Arg Arg Gln His Glu Pro
                165                 170                 175

Ser
```

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 42
gttgcgatgg tcgcgagaat aagcgt 26

<210> SEQ ID NO 43
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 43
agtaggccgt agttgcccga agttc 25

<210> SEQ ID NO 44
<211> LENGTH: 28
<212> TYPE: DNA
<213> ORGANISM: Artificial Sequence
<220> FEATURE:
<223> OTHER INFORMATION: Description of Artificial Sequence: synthetic nucleotide

<400> SEQUENCE: 44

-continued acccgattat cgtcaatgac gaacgagg 28

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 45
accatggtcg cgtagtcgtc tctc 24

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 46
gatccaacgc ttggagggac tgg 23

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 47
gaccattcga tgacgtcgct ttgcg 25

<210> SEQ ID NO 48
<211> LENGTH: 26
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 48
aattgttcga tccgatcacg gccacg 26

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 49
tgagacccac cgtcgtgcta tcgt 24

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 50
acgcgaccat atcccgctcg tgat 24

-continued

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 51
cctggtcaac gacgttgagc agacatt 27

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 52
gacgaggatt tcgagggcct aaagg 25

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: synthetic oligonucleotide

<400> SEQUENCE: 53
tcgatctcga ccagcgggaa ctc 23

<210> SEQ ID NO 54
<211> LENGTH: 640
<212> TYPE: DNA
<213> ORGANISM: Bacterium 2412.1

<400> SEQUENCE: 54
gttgcgatgg tcgcgagaat aagcgtgcga agtgggagga tgtgaagatg ggggccagga 60
gtatgtgtgc gggacggttc ggacgcttct gcattggctt ggcttcatcg gttgccgtga 120
ctctaggggg agcctccgcc gccggcgcgg caaccgcgac ggattttccg gtccgcagga 180
ccgatctggg ccaggttcag ggactggccg gggacgtgat gagctttcgc ggaataccct 240
atgcagcgcc gccggtgggc gggctgcgtt ggaagccgcc ccaacacgcc cggccctggg 300
cgggcgttcg ccccgccacc caatttggct ccgactgctt cggcgcggcc tatcttcgca 360
aaggcagcct cgcccccggc gtgagcgagg actgtcttta cctcaacgta tgggcgccgt 420
caggcgctaa acccggccag taccccgtca tggtctgggt ctacggcggc ggcttcgccg 480
gcggcacggc cgccatgccc tactacgacg gcgaggcgct tgcgcgacag ggcgtcgtcg 540
tggtgacgtt taactatcgg acgaacatcc tgggcttttt cgcccatcct ggtctctcgc 600
gcgagagccc caccggaact tcgggcaact acggcctact 640

<210> SEQ ID NO 55
<211> LENGTH: 475
<212> TYPE: DNA
<213> ORGANISM: Bacterium 2412.1

<400> SEQUENCE: 55
acccgattat cgtcaatgac gaacgaggcc gccaacggac cggcgctgaa gcccaccaac 60

-continued

```
gcgagagggg cgagcagtac ggcggcggtc ctgctgggct ccaaggcgat cacgtccgcc    120

accagaaacg gctgcagcgc cagccagaac aggccaaagc cacaagcgct tgcgatgagc    180

gcgacgggcg tgccggcgtg aagcaggccg atgacaagac cggcctgcag cactgcgccg    240

gcggccagaa ccgtacgggc gtgcacgcgc gcaccgagcc aggatgctgc aagagcaccc    300

gccacctgga aggccaggct gcccgcgatc gcggcgccga ccgtggccgg ggcgaaatgg    360

tgttgcgcgg ccaggcgctc caggtagttc catgccgccc cgatgccggc gttttgaaga    420

aacgccgcga gcgccacgac catcagggcc ggagagacga ctacgcgacc atggt         475
```

<210> SEQ ID NO 56
<211> LENGTH: 447
<212> TYPE: DNA
<213> ORGANISM: Bacterium 2412.1

<400> SEQUENCE: 56

```
gatccaacgc ttggagggac tggtcggcgg cgctctcttc gaccgaacca gccggaccat     60

gaccgagacc gcgcttggca aggagctgct gccggtggcc cgccgaacgc ttgagtttct    120

ggacaattcg ctgttcgcct cgcccaagct gcgcgaaccg cgctggaccg acatcagcat    180

tttttgcgtg cagaccgccg cgttccgcgt tctgccgcgc gcggcccggc gcttcatgga    240

tgaaaatccc cgactgcgcc tgaggatcat cgatgttccg gctgtcgaag gcgcggaact    300

ggtggcgcga ggggaagcgg agttcggtat cagcatcgag agcctgcttc cgtccggcct    360

gcgtttcgag gctcttcacg aggacccgtt tggcttggcg tgccatcgga gccatcgcct    420

ggcgcaaagc gacgtcatcg aatggtc                                        447
```

<210> SEQ ID NO 57
<211> LENGTH: 536
<212> TYPE: DNA
<213> ORGANISM: Bacterium 2412.1

<400> SEQUENCE: 57

```
tgagacccag ccgttcgtgc ttatcgtcgg cggcggtcaa ggcggtctag cgcttggcgc     60

gcgcctccgt cagctccagg tcccgactct gatcgtcgat cagcacccac gggtggggga    120

ccaatggcga tcgcggtacg catcgctctg cctgcacgat ccagtctggt acgaccacct    180

tccttacctg ccgtttcccg atacttggcc ggtttatacg cccaaggaca agatcggcga    240

ttggctcgaa gcttatgcgc aggcgatgga gctgctggtc tggtgttcga ccagatgcgt    300

gtccgccgtc tatgacgccg aagccgggcg atggaccgtc accctgcgcc gaggcgagga    360

gaccagcgtc atccgccccg cgcatctggt cctggcgacg ggcaacgccg gcaagccgcg    420

cgttccgcgc ttcaagggcc aagcgcagtt cgaaggtccg atcctgcact cgagcgccta    480

tcggagcggg gctgatttca aaggacggcg cgtggccgtg atcggatcga acaatt        536
```

<210> SEQ ID NO 58
<211> LENGTH: 715
<212> TYPE: DNA
<213> ORGANISM: Bacterium 2412.1

<400> SEQUENCE: 58

```
acgcgaccat atcccgctcg tgatcggctg cgggcccgtg ggcatggcgg tcatcgccgc     60

gctccggggt ctgggcgtcg gaccgatcat cgcggccgac ttcaatccgg cgcgtcggag    120

cctggcggcg cgcatgggcg ccgatattgt catcgacccg gcggagcggt cccccctacga    180
```

-continued

```
cgaatggcgg gataccgcgg cggcgtcagg cctggccgga ctggcggggg cgccagcgtc    240
gctgcggacc tgtctggtct tcgagtgtgt cggcctgcca ggaatgctgc gtcagatcat    300
ggaaggcgcc ccggcggagt cggagatcat cgtcgtcggg gcctgcatgg agcccgatag    360
cctcgagccg atgatggcga tgcataaggc tctgacgctg aattttcgcg aacctacacg    420
atcgaggagt tcgccgaggt ccttcggatg atcggtgagg gcgagctcca cgtcgagccg    480
ttgctcagcc aacccatcgg cctggaagac cttccggggg tcttcgacaa agcgcccggg    540
agggccgggg gcgccaaggt cctcgtcgac ccctggcgct gacgccgccg aaaaccaacg    600
acagaaaaca acgggcggga ggaacaattg ggtagcgatg agcaagacga tcctctcgtc    660
ggcggcggtc gtcagttgct tctcaagcaa tgtctgctca acgtcgttga ccagg         715

<210> SEQ ID NO 59
<211> LENGTH: 686
<212> TYPE: DNA
<213> ORGANISM: Bacterium 2412.1

<400> SEQUENCE: 59

tcgatctcga ccagcgggaa ctcgccggcg aaccggccga cggaaaccga cgtcagccgg     60
ttggtgtcca tcagtgcgcc gagtgcggtc gggaggaacg cgttgtcgcg gaagatcgtg    120
aaggcgttcg cgctgccgac aaactggttg acgaaggcgc cgaggttggt gtggctatag    180
gcataggtgc cttccgcata gagcttgacg cgttctgagg cctcgaactc gccgcggagg    240
aagccattgt agcgccgctg gtccggagcg aagccgagat tgacgcgcgg accgtcgccg    300
ccgctctgga aggaactgct ggtaaagctt ccgtagttaa aggtcgcaag cgtaccgccg    360
ggaagaaagg tgacgccctt cagcggaccc gatgtgatca ggccgccgta ggcgccgcgc    420
gagcttcgga tgtcgggaac caccgtgacg cccgtcgggg cgccgggcac gggatattgc    480
cccgccgcgc gatcatacca cgcccgatcg gtggcctgat cggcgcgaat gccgtcctcg    540
tgatagtatt cgaccgcggc aaggagatgt gcgcgccctt gggcaaacga cttgccggcc    600
gccagcgatc cgcccaccga ggccagatcg ttgcggctcg agacgccggt ctggacgttc    660
gcctttaggc cctcgaaatc ctcgtc                                         686
```